(12) United States Patent
Wernerehl et al.

(10) Patent No.: US 11,305,276 B2
(45) Date of Patent: Apr. 19, 2022

(54) SYSTEMS AND METHODS FOR POINT OF USE EVACUATION OF AN ARRAY

(71) Applicants: BioFire Defense, LLC, Salt Lake City, UT (US); Biomerieux, Inc., Durham, NC (US)

(72) Inventors: Aaron Wernerehl, Salt Lake City, UT (US); David E. Jones, Layton, UT (US); Taylor Zimmerman, Herriman, UT (US); Kirk M. Ririe, Salt Lake City, UT (US)

(73) Assignees: BIOFIRE DEFENSE, LLC, Salt Lake City, UT (US); BIOMERIEUX, INC., Durham, NC (US)

(*) Notice: Subject to any disclaimer, the term of this patent is extended or adjusted under 35 U.S.C. 154(b) by 0 days.

(21) Appl. No.: 16/606,618

(22) PCT Filed: May 23, 2018

(86) PCT No.: PCT/US2018/034194
§ 371 (c)(1),
(2) Date: Oct. 18, 2019

(87) PCT Pub. No.: WO2018/217929
PCT Pub. Date: Nov. 29, 2018

(65) Prior Publication Data
US 2021/0031183 A1    Feb. 4, 2021

Related U.S. Application Data

(60) Provisional application No. 62/510,682, filed on May 24, 2017.

(51) Int. Cl.
*B01L 3/00* (2006.01)
*B01L 7/00* (2006.01)
*C12Q 1/686* (2018.01)

(52) U.S. Cl.
CPC .............. *B01L 3/5025* (2013.01); *B01L 7/52* (2013.01); *C12Q 1/686* (2013.01);
(Continued)

(58) Field of Classification Search
CPC ....... B01L 2400/0487; B01L 2200/068; B01L 2400/049
(Continued)

(56) References Cited

U.S. PATENT DOCUMENTS 6,303,305 B1   10/2001  Wittwer et al.
6,485,690 B1*  11/2002  Pfost .................... B01J 19/0046
                                                              422/552
(Continued)

FOREIGN PATENT DOCUMENTS

CN     104159559 A    11/2014
JP     2008-539757 A  11/2008
(Continued)

OTHER PUBLICATIONS

International Search Report and Written Opinion issued in PCT/US2018/034194 dated Oct. 1, 2018.

*Primary Examiner* — Natalia Levkovich
(74) *Attorney, Agent, or Firm* — Workman Nydegger

(57) ABSTRACT

Systems, methods, and apparatus are provided for evacuating and for filling an array at the point of use.

8 Claims, 20 Drawing Sheets

(52) U.S. Cl.
CPC .............. *B01L 2200/0642* (2013.01); *B01L 2200/0684* (2013.01); *B01L 2200/0689* (2013.01); *B01L 2200/16* (2013.01); *B01L 2300/0829* (2013.01); *B01L 2400/049* (2013.01)

(58) Field of Classification Search
USPC ........................................ 422/504, 512, 552
See application file for complete search history.

(56) References Cited

U.S. PATENT DOCUMENTS

| | | | |
|---|---|---|---|
| 6,645,758 | B1 | 11/2003 | Schnipelsky et al. |
| 6,780,617 | B2 | 8/2004 | Chen |
| 7,387,887 | B2 | 6/2008 | Wittwer et al. |
| 8,394,608 | B2 | 3/2013 | Ririe et al. |
| 8,895,295 | B2 | 11/2014 | Ririe et al. |
| 9,586,208 | B2 | 3/2017 | Ririe |
| 2007/0166199 | A1 | 7/2007 | Zhou et al. |
| 2009/0226900 | A1 | 9/2009 | Babcock et al. |
| 2010/0056383 | A1 | 3/2010 | Ririe et al. |
| 2010/0105029 | A1* | 4/2010 | Ririe .................... C12Q 1/6806 435/6.12 |
| 2012/0088263 | A1 | 4/2012 | Bruno et al. |
| 2013/0171045 | A1 | 7/2013 | Ririe et al. |
| 2014/0283945 | A1 | 9/2014 | Jones et al. |
| 2015/0283531 | A1 | 10/2015 | Jones et al. |
| 2015/0321194 | A1 | 11/2015 | Weibel et al. |
| 2017/0122851 | A1 | 5/2017 | Thatcher et al. |

FOREIGN PATENT DOCUMENTS

| | | |
|---|---|---|
| JP | 2010-509918 A | 4/2010 |
| JP | 2014-533176 A | 12/2014 |
| WO | 2008/140568 A2 | 11/2008 |
| WO | 2017/147085 | 8/2017 |

* cited by examiner

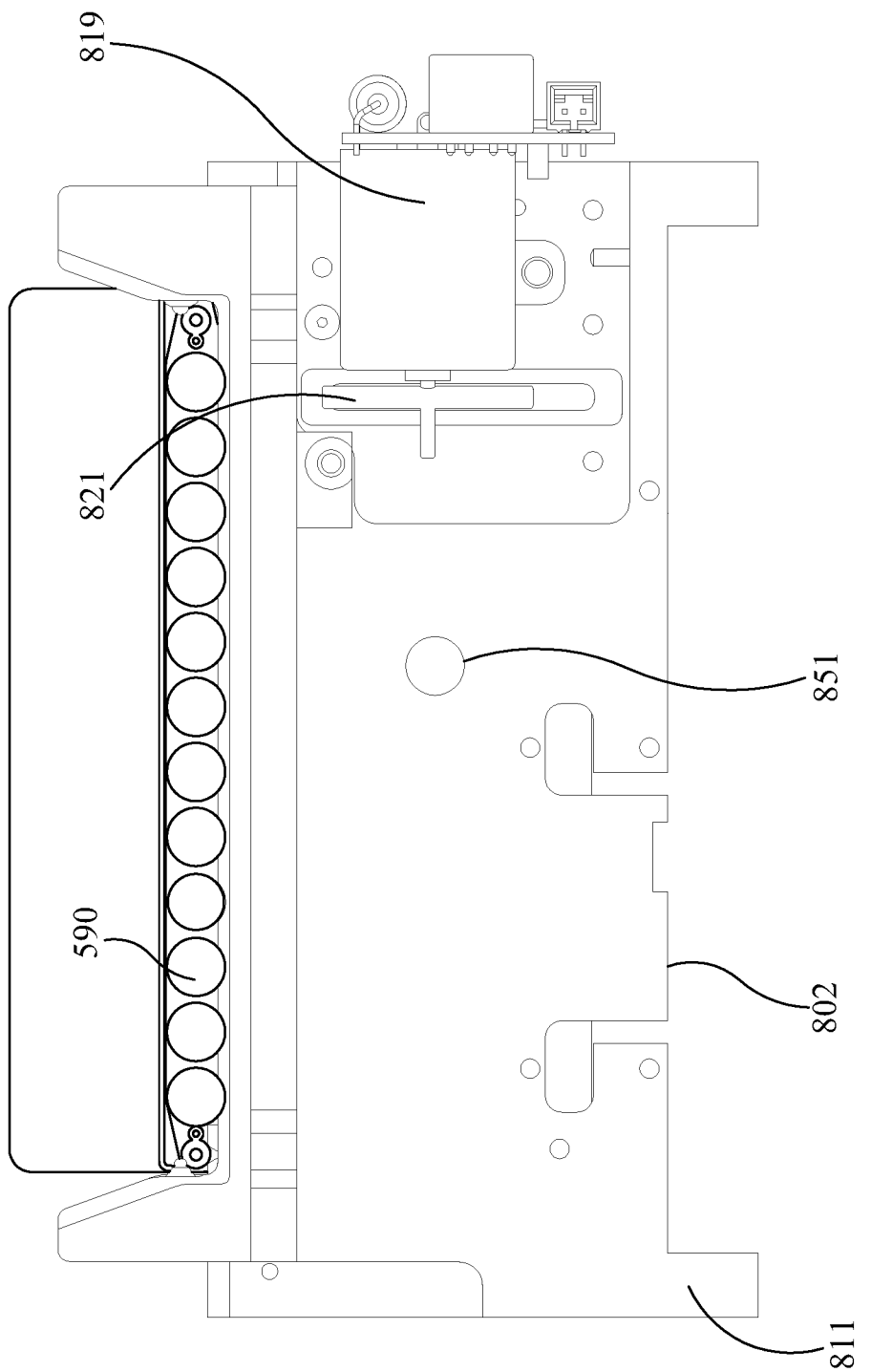

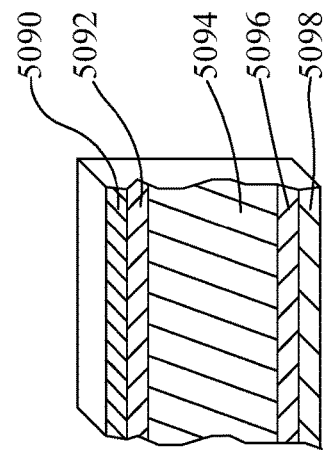
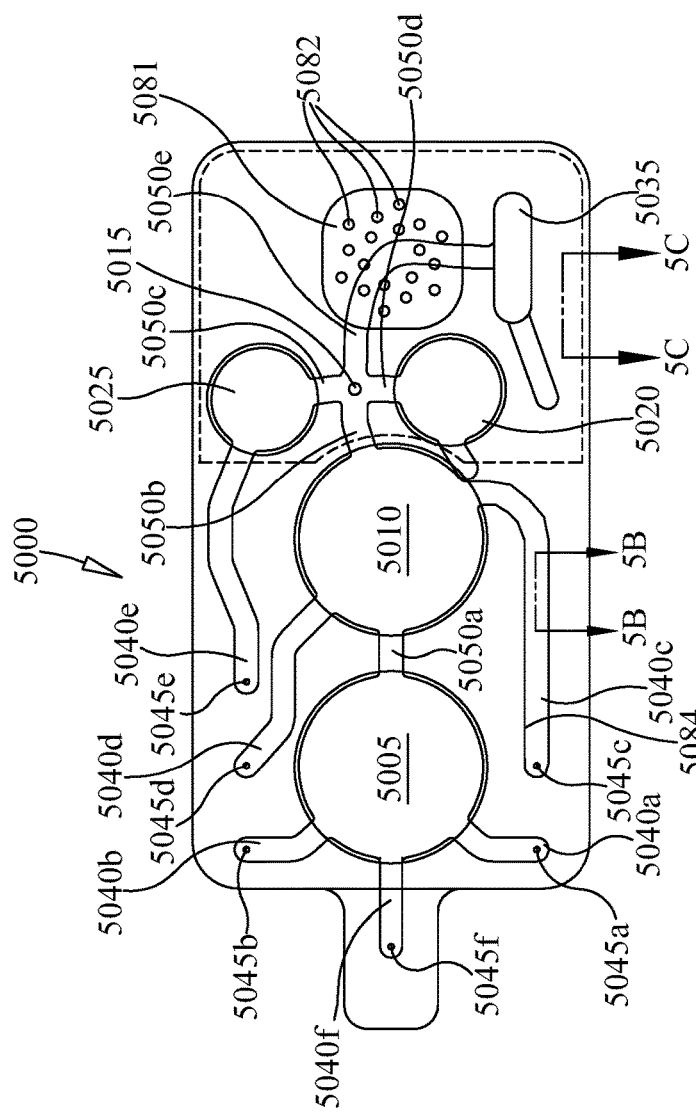
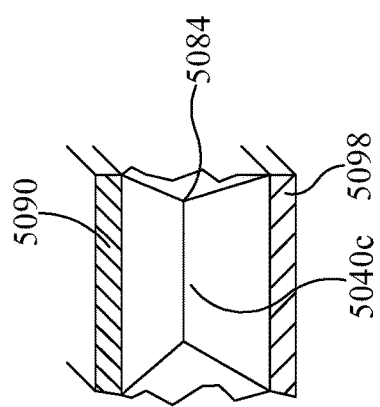

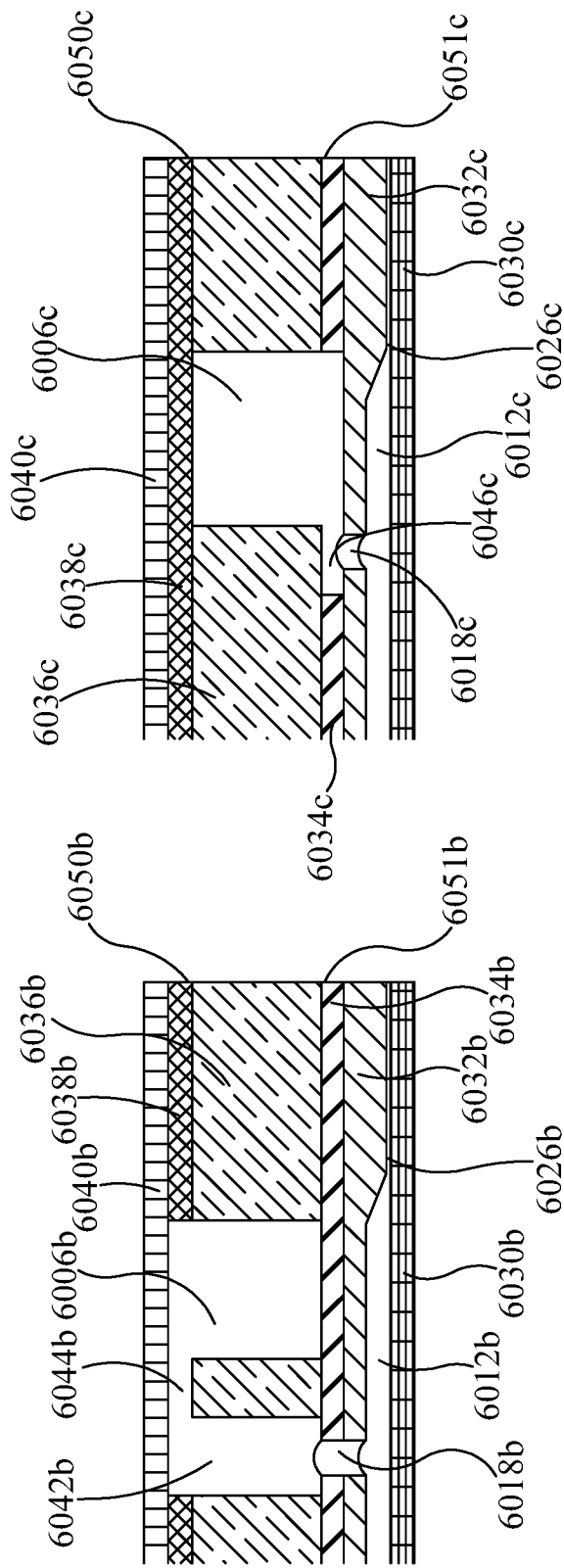

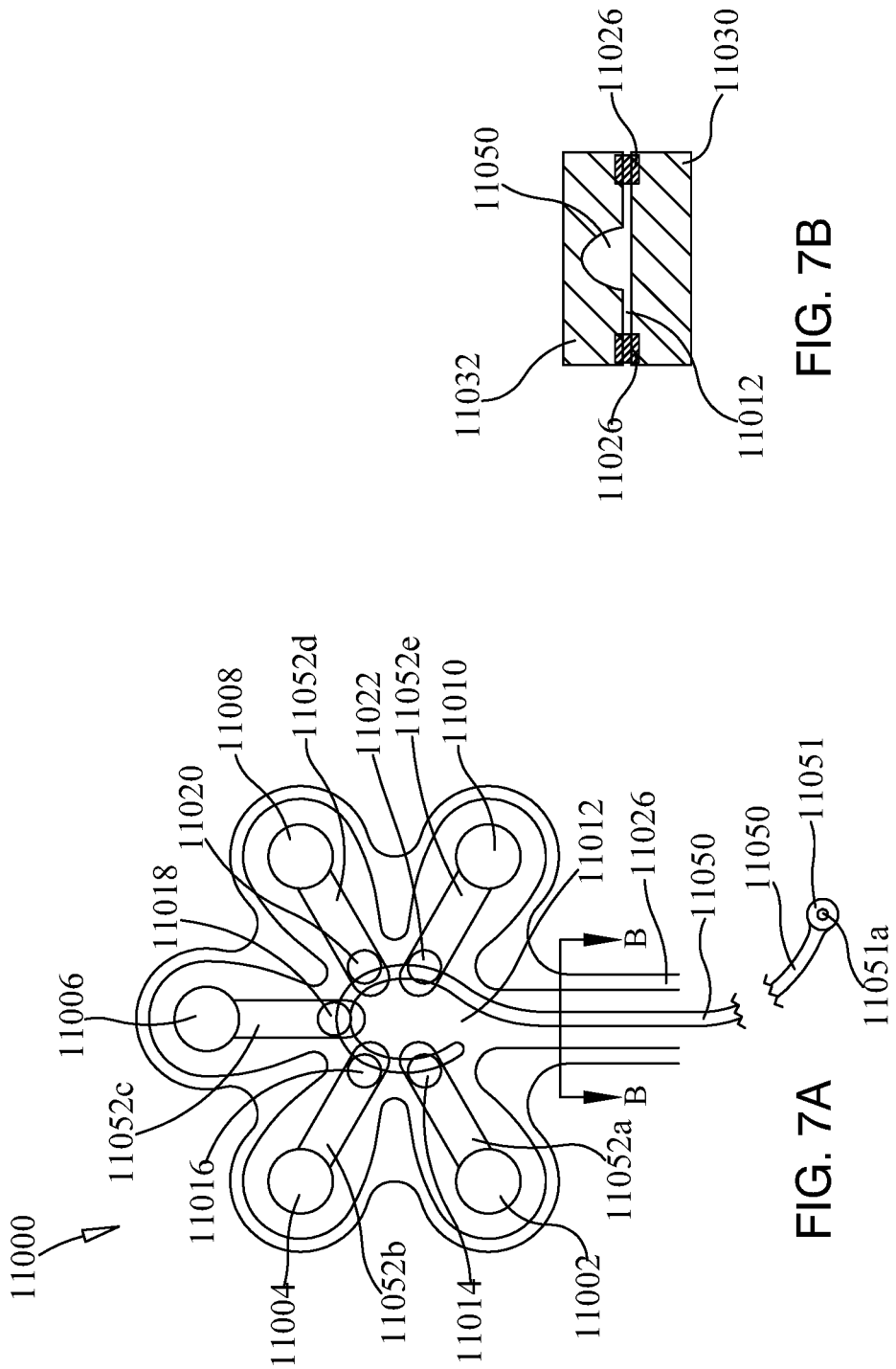

SYSTEMS AND METHODS FOR POINT OF USE EVACUATION OF AN ARRAY

RELATED APPLICATIONS

This Application is a U.S. National Stage Application of PCT/US2018/034194 filed May 23, 2018, and titled "Systems and Methods for Point of Use Evacuation of an Array", which claims the benefit of and priority to U.S. Provisional Application Ser. No. 62/510,682 filed on 24 May 2017, and titled "Systems and Methods for Point of Use Evacuation of an Array", the entireties of which are incorporated by reference herein.

BACKGROUND

Technical Field

The present disclosure relates generally to apparatus for point of use evacuation and filling of a chamber in a closed system (e.g., an array of reaction wells or a reagent blister) and to methods of manufacturing and using the same.

Related Technology

In the United States, Canada, and Western Europe infectious disease accounts for approximately 7% of human mortality, while in developing regions infectious disease accounts for over 40% of human mortality. Infectious diseases lead to a variety of clinical manifestations. Among common overt manifestations are fever, pneumonia, meningitis, diarrhea, and diarrhea containing blood. While the physical manifestations suggest some pathogens and eliminate others as the etiological agent, a variety of potential causative agents remain, and clear diagnosis often requires a variety of assays be performed. Traditional microbiology techniques for diagnosing pathogens can take days or weeks, often delaying a proper course of treatment.

In recent years, the polymerase chain reaction (PCR) has become a method of choice for rapid diagnosis of infectious agents. PCR can be a rapid, sensitive, and specific tool to diagnose infectious disease. However, a challenge to using PCR as a primary means of diagnosis is the variety of possible causative organisms or viruses and the low levels of organism or virus present in some pathological specimens. It is often impractical to run large panels of PCR assays, one for each possible causative organism or viruses, most of which are expected to be negative. The problem is exacerbated when pathogen nucleic acid is at low concentration and requires a large volume of sample to gather adequate reaction templates. In some cases there is inadequate sample to assay for all possible etiological agents. A solution is to run "multiplex PCR" wherein the sample is concurrently assayed for multiple targets in a single reaction. While multiplex PCR has proved to be valuable in some systems, shortcomings exist concerning robustness of high level multiplex reactions and difficulties for clear analysis of multiple products. To solve these problems, the assay may be subsequently divided into multiple secondary PCRs. Nesting secondary reactions within the primary product increases robustness. Closed systems such as the FilmArray® (BioFire Diagnostics, LLC, Salt Lake City, Utah) reduce handling, thereby diminishing contamination risk.

Technical Problems

A variety of analytical systems and methods incorporate multi-well arrays as a means of performing analysis on numerous samples. Typically, each well in such as sample vessel is intended to provide a stand-alone analysis. Accordingly, the wells and analytical material therein are generally designed to be kept separate one from another, without any substantial cross-talk therebetween. For this reason, loading each well of the array presents a challenge, particularly in closed systems. For example, in some closed array systems, the wells may be loaded individually by separate fluid channels that extend to each of the wells to reduce cross-contamination between the wells. However, filling such channels without bubble formation can be challenging, and the presence of bubbles in the wells can be problematic, as some wells may have diminished sample volume, and the presence of bubbles may lead to detection issues. Additionally, such systems can be costly and cumbersome to manufacture. Moreover, the use of separate fluid channels may create well-to-well variability in material and, therefore, analytical results.

In other systems, all or a part of the array may be flooded with material simultaneously and a restrictive opening into each well may be used to reduce contamination between wells. For example, the array can have a film cover that seals the wells, with a piercing disposed in the film over each well. See, for example U.S. Pat. No. 8,895,295, herein incorporated by reference in its entirety. Fluid material may be dispersed over the surface of the array cover film such that an aliquot of fluid material enters each well through the respective piercings. The piercings can be configured to restrict fluid from exiting the well (e.g., absent a force applied thereto).

In various systems, a pressure differential can be used to load the wells with the fluid. For instance, a positive pressure can be used to force the sample through the fluid pathway, through the piercings, if applicable, and into the wells. However, positive pressure applications may damage the structural features associated with the array if pressure in the system builds up. Accordingly, some existing systems that employ positive pressure and separate fluid channels to fill each well use a vent or overflow system (e.g. an "out" channel, out of the well), which allows overfill. However, this method requires a precise measurement of the amount of fluid forced into the system and often results in well-to-well and sample vessel-to-sample vessel variability in filling. In addition, the venting channel may inadvertently introduce contaminants into the array system, which can damage the apparatus and generate erroneous results. Moreover, while some of the air disposed in the fluid pathway is expelled by the incoming fluid, air bubbles can become trapped in the pathways, which may affect analysis of the sample and may enhance cross-talk during analytical methods involving thermocycling, as the air bubble expands during heating.

As an alternative, negative pressure (or vacuum) can be used to draw the fluid material into each well. Existing systems that employ separate fluid channels to fill each well may evacuate air from the wells and fluid channels by drawing a vacuum through the fluid sample. Accordingly, when the vacuum is released, the fluid material is drawn through the fluid channels into each of the wells. However, the level of vacuum (or pressure differential) is limited to the partial pressure of the fluid sample. For example, the partial vapor pressure of water is about 25-32 millibar at room-temperature (i.e., 20-25° C.) and at 1 atmosphere of pressure, and the partial vapor pressure of water rises as a vacuum is drawn. Accordingly, only a limited amount of air can be removed from each well in the presence of water or other fluid.

In existing array flooding systems, the vacuum may be applied or drawn at the time of manufacture. For example, an array can be sealed in an evacuation chamber such that the array is assembled under vacuum (or negative pressure) conditions. The array system is then packaged, stored, and transported under conditions that maintain the vacuum applied during manufacture. However, such a system requires materials and/or packaging that can maintain an appropriate level of vacuum until use, which can add considerable expense to the product.

Accordingly, there exists a need in the art for products, methods, and systems for in situ evacuation and filling of chambers in a closed system (e.g., an array of reaction wells or a reagent blister), a need for instruments configured for in situ evacuation of the chambers in a closed system, a need for methods of use for reaction chambers that employ in situ evacuation, and a need for methods for manufacturing reaction containers configured for in situ evacuation.

BRIEF SUMMARY

Solutions to the Problems

Embodiments of the present disclosure solve one or more of the foregoing or other problems in the art with novel systems and methods for point-of-use evacuation and, preferably, subsequent filling of one or more types of chambers, especially in a closed environment. For example, some embodiments include an array assembly that can be evacuated on demand, at the point-of-use, and/or in real-time (i.e., during performance of steps of an analytical method). Accordingly, in preferred embodiments, the vacuum need only be held for a few seconds to a few minutes (i.e., long enough to draw the vacuum, reseal the system, and, preferably, open a fill seal to fill the evacuated chamber (e.g., an array of wells) with a liquid). Thus, a near fully drawn vacuum can be used to draw fluid into the array assembly upon opening the fill seal.

Because, in one illustrative example, the vacuum is not drawn through a liquid sample, the vacuum is not limited to the vapor pressure of the liquid (e.g., water). The negative pressure level of the strong vacuum may thoroughly evacuate air from the array assembly so that residual air is minimized in the array assembly. Illustratively, the strong vacuum also effectively draws a full, consistent amount of fluid into each of the wells upon releasing the vacuum. Because air in the array assembly has been thoroughly evacuated, air bubbles in the drawn fluid may be reduced, as compared to existing systems, minimized, or, preferably, eliminated. Moreover, the array assembly can be configured (e.g., sized and structured) so that an evacuation chamber is not required to apply the vacuum. Instead, in illustrative embodiments, a piston pump or other vacuum device can be used to apply closer to a true vacuum in the array assembly.

In some embodiments, the array assembly can have a plurality of wells configured in an array, a vacuum channel in fluid communication with the plurality of wells and with a vacuum port, and an array fill channel in fluid communication with the plurality of wells and with a fluid reservoir. The fluid channel and the vacuum channel may be co-aligned and may be co-extensive, and, in some embodiment, may be the same. An openable fill seal can be disposed in the fill channel or a fluid channel disposed between the fill channel and the fluid reservoir. In some embodiments, the fill seal can be or comprise an openable seal (e.g., a frangible seal or a peelable seal), such as a seal formed by the collapsing the fill channel or fluid channel. A vacuum device can be coupled with the vacuum port and a vacuum can be applied to the array assembly (i.e., vacuum channel, plurality of wells, and fill channel.

A vacuum seal can be preferably placed over the vacuum channel (e.g., between the vacuum port and the plurality of wells) to maintain the vacuum in the wells. The openable fill seal, which may be preferably placed between the array and another blister (e.g., a fluid reservoir), can prevent evacuation of the fluid reservoir while the array assembly is under vacuum. When the fill seal is opened, fluid in the reservoir can be drawn through the fluid channel and array fill channel, into the plurality of wells. In the plurality of wells, the fluid can mix with one or more reagents.

In some embodiments, the well seal can be formed between at least some of the plurality of wells. For instance, segments of the array fill channel can extend through a row of wells in the array. Accordingly, the fill channel segment can communicate with wells in the row, but not directly with wells in an adjacent or different row. By forming a well seal, such as a heat weld between the card layer and the second film layer, crossways of the row of wells and the fill channel segments, each well can be sealed off or isolated from all other wells. In this way, cross-talk between wells of the array can be minimized or eliminated.

In some embodiments, an openable fill seal can also be formed in the fluid channel in fluid communication with the fluid reservoir and the fill channel. Because the array assembly need not be assembled under vacuum, such as in a vacuum chamber, the array assembly need not be packaged, stored, and shipped in a vacuum-sealed container. This advantage of the present disclosure can produce significant labor and material cost savings, making analytical techniques performed with the array assembly more affordable for consumers. Moreover, embodiments of the present disclosure can have a smaller material footprint, as robust, vacuum-sealable packaging containers need not be used.

In some embodiments, the array assembly can include a card layer having the plurality of wells formed therein, a first film layer bonded to a first side of the card layer, and/or a second film layer bonded to a second side of the card layer. The first film layer can seal a first end of each of the plurality of wells. The second film layer can at least partially seal a second end of the plurality of wells. The first film layer and second film layer can form a pouch in which the card layer is disposed. For instance, the card layer can be laminated by adhesive or thermoforming between the first film layer and second film layer.

In certain embodiments, the card layer, first film layer, and/or second film layer can be configured to and/or cooperate to form the vacuum channel and/or the array fill channel. For instance, in at least one embodiment, the vacuum channel and/or the fill channel can be formed in the card layer or can, for example, be impressed into a surface portion thereof. In some embodiments, the vacuum channel and/or the fill channel can be formed in the second film layer or surface portion thereof. The second film layer can be bonded to a third film layer such that the vacuum channel and/or the fill channel are formed between the second film layer and the third film layer. The third film layer can have a plurality of piercings. The piercings can be aligned and/or in fluid communication with the plurality of wells, the vacuum channel, and/or the fill channel.

The array assembly can be manufactured by bonding the first film layer to the first side of a card layer and bonding the second film layer to a second side of the card layer so as to form the vacuum channel and the array fill channel. In some embodiments, the first film layer and the second film layer can be bonded together forming a card layer pouch. Bonding the film layers together can form the fluid channel, liquid reservoir, and/or other component(s) of a sample vessel. The card layer (e.g., with recessed conduit formed therein) can optionally be prepared with reagents in the plurality of wells and inserted into the pouch through an opening formed by separation of the first and second film layers. The first and second film layers can be bonded to opposing sides of the card, and the pouch can be sealed with the card layer therein, such as by heat welding the opening in the pouch.

Described herein are:

1. An array assembly, comprising:
a first layer and at least a second layer;
a third layer having a plurality of wells formed therein, the third layer being disposed between the first and second layers;
a vacuum channel in fluid communication with the plurality of wells and with a vacuum port; and
an array fill channel in fluid communication with the plurality of wells and with a fluid source.

2. The array assembly of clause 1, wherein the first and second layers are film layers.

3. The array assembly of clauses 1 or 2, wherein the third layer comprises a card layer having the plurality of wells formed therein.

4. The array assembly of clause 3, wherein the first layer is bonded to a first side of the card layer and seals a first end of each of the plurality of wells, and the second layer is bonded to a second side of the card layer and seals a second end of each of the plurality of wells.

5. The array assembly of clauses 1-4, wherein the vacuum port comprises an opening in one or more of the first layer or the second layer.

6. The array assembly of clauses 3-5, further comprising a recessed conduit in the card layer, wherein at least a portion of one or more of the vacuum channel and the array fill channel is formed between the second film layer and the recessed conduit in the card layer, and wherein the recessed conduit in the card layer has a manifold configuration that fluidically connects the plurality of wells to the vacuum port by at least two paths and fluidically connects each well to the fluid source by at least two paths.

7. The array assembly of clauses 1-6, wherein at least a portion of the vacuum channel is disposed in and/or co-localized with at least a portion of the array fill channel.

8. The array assembly of clauses 1-7, further comprising an openable seal in the array fill channel between the plurality of wells and the fluid source.

9. The array assembly of clauses 1-8, wherein the plurality of wells are disposed in a respective plurality of rows, the array fill channel comprises an access channel in fluid communication with the fluid source and with a manifold channel assembly, the manifold channel assembly comprising:
a plurality of branch channels extending along the respective plurality of rows, the plurality of branch channels respectively being in fluid communication with the plurality of wells; and
a first main channel extending along a first end of the plurality of rows, the plurality of branch channels extending from the first main channel, the array fill channel in communication with the first main channel.

10. The array assembly of clauses 1-9, wherein the manifold channel assembly further comprises a second main channel in fluid communication with the plurality of branch channels, the second main channel extending along a second end of the plurality of rows, the vacuum port in communication with the second main channel, wherein each well is in fluid communication with the vacuum port and the fluid source by at least two different paths.

11. The array assembly of clauses 1-10, wherein the manifold channel assembly further comprises a plurality of connection channels extending respectively from each of the plurality of branch channels to the plurality of wells, the plurality of connection channels respectively being in fluid communication with the plurality of wells.

12. A method of manufacturing an array assembly, the method comprising:
providing a card layer having a plurality of wells disposed therein;
disposing the card layer between a first film layer and at least a second film layer;
bonding the first film layer to a first side of a card layer; and
bonding the second film layer to a second side of the card layer,
wherein the card layer and at least one of the first or second film layers form:
(i) a vacuum channel extending between and/or in fluid communication with the plurality of wells and a vacuum port; and
(ii) an array fill channel extending between and/or in fluid communication with the plurality of wells and a fluid source.

13. The method of clause 12, wherein the recessed conduit in the card layer has a manifold configuration.

14. A method of using an array assembly on a sample, comprising
(a) providing a sample container comprising a reaction zone in fluid communication with the array assembly, the array assembly comprising
a plurality of wells configured in an array,
an access opening between the reaction zone and array,
a vacuum port,
a plurality of channels such that each well in the array is fluidly connected to the access opening and the vacuum port;
(b) performing an analytical method on the sample in the reaction zone to produce a reaction mixture;
(c) opening the vacuum port and drawing a vacuum on the array assembly such that air is evacuated from the plurality of wells and the plurality of channels;
(d) sealing vacuum port such that the plurality of wells are maintained under the vacuum, thereby forming an evacuated array; and
(e) opening the access opening such that the reaction mixture is drawn into the plurality of wells via the array fill channel.

15. The method of clause 14, further comprising mixing the reaction mixture with one or more reagents disposed in each of the plurality of wells to form a second mixture, and performing a second analytical method on the second reaction mixture.

16. The method of clause 14 or 15, wherein the second mixture is a PCR mixture.

17. The method of clauses 14-16, further comprising thermocycling the second reaction mixture.

18. The method of clauses 14-17, further comprising detecting an amplification product in at least one of the plurality of wells.

19. The method of clauses 14-18, wherein the sample comprises a microorganism and one or more reagents comprises an antibiotic.

20. The method of clause 19, wherein the antibiotic is present in a first of the plurality of wells at a first concentration and is present in a second of the plurality of wells at a second concentration, wherein the second concentration is lower than the first concentration.

21. The method of clauses 14-20, wherein step (c) provides a vacuum in the plurality of wells of between about 2 millibar and about 150 millibar.

22. The method of clauses 14-21, wherein steps (c) and (d) are performed before step (b) is completed.

23. A method for performing a multi-step biological reaction in a sealed sample container, comprising:
    (a) providing a sealed container comprising a first reaction zone, a second reaction zone, and dried components in the second reaction zone,
    (b) performing a first reaction in the first reaction zone, to generate a reaction mixture,
    (c) hydrating the dried components in the second reaction zone with a hydration fluid to generate hydrated components, wherein step (c) is performed before or during step (b),
    (d) adding a portion of the reaction mixture to the hydrated components, and
    (e) performing a second reaction in the second reaction zone.

24. The method of clause 23, wherein the second reaction zone is an array of wells, wherein each well is provided with dried components, and wherein at least a plurality of wells has components that are different from other wells in the plurality of wells.

25. The method of clauses 23 or 24, wherein each individual well in the array of wells is provided with a barrier layer that retards entry of the hydration fluid into the wells.

26. The method of clauses 23-25, wherein the hydrating step comprises filling the plurality of wells with the hydration fluid, followed by removing from the array of wells of any excess hydration fluid.

27. The method of clauses 23-26, wherein the adding step comprises moving the reaction mixture to the array, allowing a portion of the reaction mixture to cross the barrier layer and enter each well, and removing from the array any excess reaction mixture.

28. The method of clauses 23-26, wherein the adding step comprises moving the reaction mixture to the array, and sealing a portion of the reaction mixture adjacent each well outside the barrier layer, so that the reaction mixture and hydrated components may mix through the barrier layer.

29. The method of clauses 23-28, wherein the barrier layer is a pierced layer having one or more openings per well, wherein the openings are sized such that absent some force, fluid does not readily flow through the openings.

30. The method of clauses 23-29, wherein the first reaction is first-stage PCR and the second reaction is second-PCR.

31. The method of clauses 23-30, wherein the second reaction zone is maintained at a cool temperature prior to step (d).

32. The method of clauses 23-31, further comprising evacuating at least the second reaction zone with a partial vacuum prior to step (c).

33. An array assembly, comprising:
    a card having a plurality of wells arranged in an array;
    an access opening in a first side of the card;
    a channel system in fluid communication with the access opening and with the plurality of wells; and
    a vacuum port in fluid communication with the channel system.

34. The array assembly of clause 33, wherein the array comprises a plurality of rows, each of the plurality of rows comprising one or more wells, the channel system comprising a manifold channel assembly comprising:
    a plurality of branch channels extending along the plurality of rows, the plurality of branch channels respectively being in fluid communication with the plurality of wells; and
    a first main channel in fluid communication with the access opening extending along a first end of the plurality of rows, the plurality of branch channels extending from the first main channel,
    a second main channel in fluid communication with the plurality of branch channels, the second main channel extending along a second end of the plurality of rows, the vacuum port in communication with the second main channel,
    wherein each well is in fluid communication with the vacuum port and the access opening by at least two different paths.

35. The array assembly of one of clauses 33 or 34, further comprising a first film layer and a second film layer, wherein first and second film layers form a pouch, the card layer being at least partially sealed inside the pouch.

36. A reaction container, comprising:
    a plurality of fluidly connected reaction chambers,
    an array comprising
    an access opening in fluid communication with at least one of the fluidly connected reaction chambers;
    a plurality of reaction wells;
    a vacuum port;
    a channel system in fluid communication with the access opening, with the plurality of wells and with the vacuum port, the channel system providing paths such that each reaction well in the array is fluidly connected to the vacuum port by at least two paths and each reaction well is also connected to the fluid source by at least two paths.

37. The array assembly of clause 36, wherein the vacuum port is reversibly sealable and the access opening is reversibly sealable.

38. An array assembly, comprising:
    a plurality of wells arranged in an array;
    a vacuum channel in fluid communication with the plurality of wells and with a vacuum port; and
    an array fill channel in fluid communication with the plurality of wells and with a fluid source.

39. The array assembly of clause 38, further comprising
    a card layer having the plurality of wells formed therein,
    a first film layer bonded to a first side of the card layer, wherein the first film layer seals a first end of each of the plurality of wells,
    a second film layer bonded to a second side of the card layer, wherein the vacuum port comprises an opening in one or more of the first film layer and the second film layer.

40. The array assembly of clause 38 or 39, wherein at least a portion of one or more of the vacuum channel and the array fill channel is formed (i) in the card layer, (ii) in the second film layer, or (iii) between the card layer and the second film layer.

41. The array assembly of clauses 38-40, wherein at least a portion of one or more of the vacuum channel and the array fill channel is formed between the first film layer and the second film layer.

42. The array assembly of clauses 38-41, wherein a portion of the array fill channel is formed between the first film layer and the second film layer and is disposed about at least a portion of a perimeter of the card layer.

43. The array assembly of clauses 38-42, further comprising a recessed conduit in the card layer, wherein the recessed conduit in the card layer has a manifold configuration wherein each well in the array is fluidly connected to the vacuum port by at least two paths and each well is also connected to the fluid source by at least two paths.

44. The array assembly of clauses 38-43, wherein the second film layer has a recessed conduit formed therein, further comprising a third film layer disposed between the second film layer and the card layer, wherein the third film layer has a plurality of piercings extending therethrough, and wherein the plurality of piercings are in fluid communication with the recessed conduit in the second film layer.

45. The array assembly of clauses 38-44, wherein at least a portion of the array fill channel is disposed between the recessed conduit in the second film layer and the bond between the third film layer and the second film layer between two or more portions of the recessed conduit in the second film layer.

46. The array assembly of clauses 38-45, wherein at least a portion of the vacuum channel is provided as a portion of the array fill channel and is configured to maintain the array fill channel in an open position.

47. The array assembly of clauses 38-46, further comprising an openable seal in the array fill channel between the plurality of wells and the fluid source.

48. The array assembly of clauses 38-47, further comprising one or more reagents disposed in each of the plurality of wells.

49. The array assembly of clauses 38-48, wherein the plurality of wells are disposed in a respective plurality of rows, the array fill channel comprising an access channel in fluid communication with the fluid source and with a manifold channel assembly, the manifold channel assembly comprising:
a plurality of branch channels extending along the respective plurality of row, the plurality of branch channels respectively being in fluid communication with the plurality of wells; and
a first main channel extending along a first end of the plurality of rows, the plurality of branch channels extending from the first main channel, the array fill channel extending from the first main channel.

50. The array assembly of clauses 38-49, wherein the manifold channel assembly further comprises a second main channel in fluid communication with the plurality of branch channels, the second main channel extending along a second end of the plurality of rows, the vacuum port in communication with the second main channel, wherein each well is in fluid communication with the vacuum port and the fluid source by at least two different paths.

51. The array assembly of clauses 38-50, wherein the manifold channel assembly further comprises a plurality of connection channels extending respectively from each of the plurality of branch channels to the plurality of wells, the plurality of connection channels respectively being in fluid communication with the plurality of wells.

52. A method of drawing a vacuum on a reaction container in situ while performing an analytical method, the method comprising:
providing a reaction container that includes a sample introduction zone, at least a first reaction zone in fluid communication with the sample introduction zone, and a second reaction zone in fluid communication with the first reaction zone, wherein the second reaction zone comprises a plurality of wells, a vacuum channel in fluid communication with the plurality of wells and a vacuum port, an array fill channel extending between and/or in fluid communication with the plurality of wells and the first reaction zone, and an openable seal disposed between the first reaction zone and the second reaction zone;
performing at least one step of the analytical method with the reaction container;
drawing a partial vacuum on the plurality of wells such that the plurality of wells, the vacuum channel, and at least a portion of the array fill channel are under reduced pressure relative to atmospheric pressure;
sealing a portion of the vacuum channel such that the plurality of wells and at least the portion of the array fill channel are maintained under the vacuum, thereby forming an evacuated array; and
applying a fluid to the evacuated array by opening the openable seal disposed between the first reaction zone and the second reaction zone such that the fluid is drawn into the plurality of wells via the array fill channel.

53. The method of clause 52, wherein the at least one step of the analytical method includes removing the reaction container from an ambient pressure package, introducing a sample into the sample introduction zone, inserting the reaction container into an instrument configured for performing the analytical method and configured for drawing a partial vacuum to form the evacuated array, performing one or more reactions in the first reaction zone, or preparing for applying the fluid to the evacuated array.

54. The method of clauses 52 or 53, wherein performing one or more reactions in the first reaction zone comprises one or more of performing a sample lysis to generate a lysate, isolating lysis particles from the lysate, mixing silica magnetic beads with the lysate, moving a residual lysate after nucleic acid capture with the silica magnetic beads to a waste chamber, performing at least one wash of the magnetic beads and moving the wash liquid to the waste chamber, eluting nucleic acids from the silica magnetic beads, performing a first singleplex or multiplex PCR reaction, or diluting a product of the first PCR reaction in preparation for performing a second PCR reaction in the plurality of wells of the second reaction zone.

55. The method of clauses 52-54, wherein the reaction container further includes one or more reagent blisters fluidically connected to one or more of the sample introduction zone, the first reaction zone, or the second reaction zone.

56. The method of clauses 52-55, wherein at least one of the one or more reagent blisters includes a dried reagent, and the method further comprising drawing a partial vacuum on the one or more reagent blisters including the dried reagent.

57. The method of clauses 52-56, further comprising mixing a fluid with the dried reagent to form a first mixture.

58. The method of clauses 52-57, wherein the one or more reagent blisters comprise reagents for sample preparation, nucleic acid recovery, a first-stage PCR, and a second-stage PCR.

59. A system, comprising:
a reaction container that includes a sample introduction zone, at least a first reaction zone in fluid communication with the sample introduction zone, and a second reaction zone in fluid communication with the first reaction zone, wherein the second reaction zone comprises a plurality of wells, a vacuum channel extending between and/or in fluid communication with the plurality of wells and a vacuum port, an array fill channel extending between and/or in fluid communication with the plurality of wells and the first reaction zone, and an openable seal disposed between the first reaction zone and the second reaction zone;

an instrument configured to perform an analytical method using the reaction container, wherein the instrument includes a vacuum system to draw a partial vacuum in one or more portions of the reaction container while performing one or more steps of the analytical method.

60. The system of clause 59, wherein the one or more portions of the reaction container configured to have a partial vacuum drawn thereon are substantially dry such that the partial vacuum is not being drawn against a partial pressure of water.

61. The system of clauses 59 or 60, wherein the partial vacuum in the one or more portions of the reaction container configured to have a partial vacuum drawn thereon is in a range between about 2 millibar and about 150 millibar.

62. The system of clauses 59-61, wherein the one or more portions of the reaction container configured to have a partial vacuum drawn thereon include the plurality of wells, the vacuum channel, and at least a portion of the array fill channel.

63. The system of clauses 59-62, wherein the instrument includes a seal device apply a seal to preserve the partial vacuum drawn one or more portions of the reaction container.

64. The system of clauses 59-63, wherein the reaction container further includes one or more reagent blisters fluidically connected to one or more of the sample introduction zone, the first reaction zone, or the second reaction zone.

65. The system of clauses 59-64, wherein at least one of the one or more reagent blisters includes a dried reagent, and wherein the one or more portions of the reaction container configured to have a partial vacuum drawn thereon include the one or more reagent blisters that include the dried reagent.

66. The system of clauses 59-65, wherein the instrument is a PCR instrument that includes at least one heater positioned and arranged for thermocycling at least one portion of the reaction container.

67. The system of clauses 59-66, wherein the instrument includes at least one heater positioned and arranged for controlling the temperature in at least one portion of the reaction container for performing an isothermal reaction.

68. The system of clauses 59-67, wherein the instrument includes at least one heater positioned and arranged for controlling the temperature in at least one portion of the reaction container, one or more actuators for moving fluid in the reaction container, and one or more seals for controlling the movement of fluids within one or more portions of the reaction container.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description that follows, and in part will be obvious from the description, or may be learned by the practice of the invention. The features and advantages may be realized and obtained by means of the instruments and combinations particularly pointed out in the appended claims. These and other features will become more fully apparent from the following description and appended claims, or may be learned by the practice of the invention as set forth hereinafter.

BRIEF DESCRIPTION OF THE DRAWINGS

FIG. 4 shows a motor used in one illustrative embodiment of the instrument of FIG. 2.

FIG. 5A shows another embodiment of a flexible pouch.

FIG. 5B illustrates a cross-sectional view of a portion of the pouch of FIG. 5A along the line B-B.

FIG. 5C illustrates a cross-sectional view of a portion of the pouch of FIG. 5A along the line C-C.

FIG. 6B is a cross-sectional view illustrated along the line B-B of FIG. 6A showing one embodiment of a well filling system.

FIG. 6C is an alternative embodiment showing a different embodiment of a well filling system.

FIG. 7A illustrates a second-stage array showing one embodiment of a point-of-use array evacuation system.

FIG. 7B is a cross-sectional view of a portion of FIG. 7A along the line B-B.

DETAILED DESCRIPTION

Figure 1:
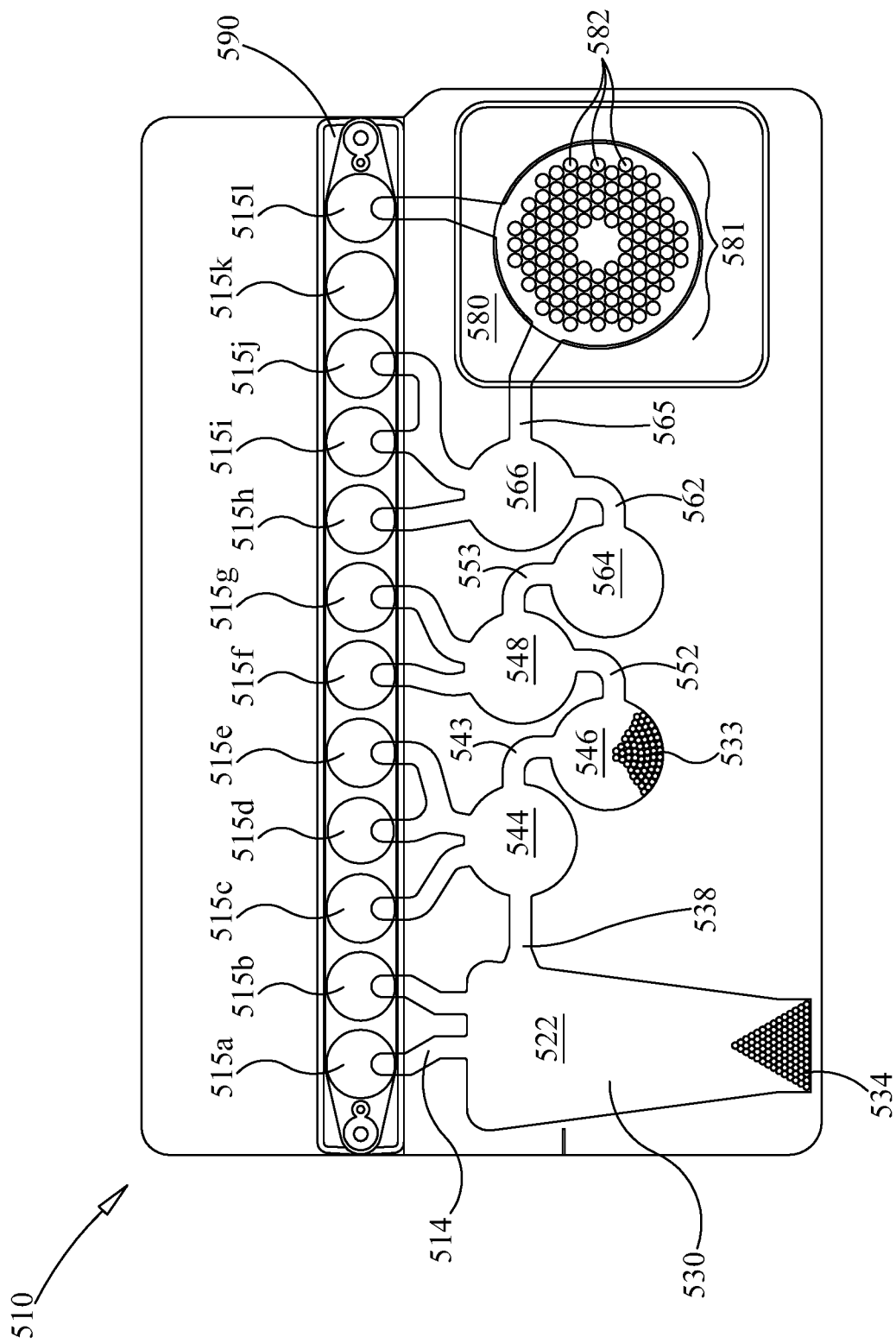
FIG. 1 shows a flexible pouch useful for self-contained PCR.

Example embodiments are described below with reference to the accompanying drawings. Many different forms and embodiments are possible without deviating from the spirit and teachings of this disclosure and so the disclosure should not be construed as limited to the example embodiments set forth herein. Rather, these example embodiments are provided so that this disclosure will be thorough and complete, and will convey the scope of the disclosure to those skilled in the art. In the drawings, the sizes and relative sizes of layers and regions may be exaggerated for clarity. Like reference numbers refer to like elements throughout the description.

Unless defined otherwise, all terms (including technical and scientific terms) used herein have the same meaning as commonly understood by one of ordinary skill in the art to which the present disclosure pertains. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. While a number of methods and materials similar or equivalent to those described herein can be used in the practice of the present disclosure, only certain exemplary materials and methods are described herein.

All publications, patent applications, patents or other references mentioned herein are incorporated by reference for in their entirety. In case of a conflict in terminology, the present specification is controlling.

Various aspects of the present disclosure, including devices, systems, methods, etc., may be illustrated with reference to one or more exemplary implementations. As used herein, the terms "exemplary" and "illustrative" mean "serving as an example, instance, or illustration," and should not necessarily be construed as preferred or advantageous over other implementations disclosed herein. In addition, reference to an "implementation" or "embodiment" of the present disclosure or invention includes a specific reference to one or more embodiments thereof, and vice versa, and is intended to provide illustrative examples without limiting the scope of the invention, which is indicated by the appended claims rather than by the following description.

It will be noted that, as used in this specification and the appended claims, the singular forms "a," "an," and "the" include plural referents unless the content clearly dictates otherwise. Thus, for example, reference to "a tile" includes one, two, or more tiles. Similarly, reference to a plurality of referents should be interpreted as comprising a single referent and/or a plurality of referents unless the content and/or context clearly dictate otherwise. Thus, reference to "tiles" does not necessarily require a plurality of such tiles. Instead, it will be appreciated that independent of conjugation; one or more tiles are contemplated herein.

As used throughout this application the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, directional and/or arbitrary terms, such as "top," "bottom," "left," "right," "up," "down," "upper," "lower," "inner," "outer," "internal," "external," "interior," "exterior," "proximal," "distal," "forward," "reverse," and the like can be used solely to indicate relative directions and/or orientations and may not be otherwise intended to limit the scope of the disclosure, including the specification, invention, and/or claims.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present.

Example embodiments of the present inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the present inventive concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

It is also understood that various implementations described herein can be utilized in combination with any other implementation described or disclosed, without departing from the scope of the present disclosure. Therefore, products, members, elements, devices, apparatuses, systems, methods, processes, compositions, and/or kits according to certain implementations of the present disclosure can include, incorporate, or otherwise comprise properties, features, components, members, elements, steps, and/or the like described in other implementations (including systems, methods, apparatus, and/or the like) disclosed herein without departing from the scope of the present disclosure. Some embodiments, or aspects thereof, may be described as alternatives. It will be appreciated, however, that such alternatives may not always be mutually exclusive. Accordingly, the terms "alternative," "alternatively," and the like can be replaced with "additional," "additionally," and the like. Thus, reference to a specific feature in relation to one implementation should not be construed as being limited to applications only within that implementation.

The headings used herein are for organizational purposes only and are not meant to be used to limit the scope of the description or the claims. To facilitate understanding, like reference numerals have been used, where possible, to designate like elements common to the figures. Furthermore, where possible, like numbering of elements have been used in various figures. Furthermore, alternative configurations of a particular element may each include separate letters appended to the element number.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 5%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The word "or" as used herein means any one member of a particular list and also includes any combination of members of that list.

By "sample" is meant an animal; a tissue or organ from an animal; a cell (either within a subject, taken directly from a subject, or a cell maintained in culture or from a cultured cell line); a cell lysate (or lysate fraction) or cell extract; a solution containing one or more molecules derived from a cell, cellular material, or viral material (e.g. a polypeptide or nucleic acid); or a solution containing a non-naturally occurring nucleic acid, which is assayed as described herein. A sample may also be any body fluid or excretion (for example, but not limited to, blood, urine, stool, saliva, tears, bile, or cerebrospinal fluid) that may or may not contain host or pathogen cells, cell components, or nucleic acids. Samples may also include environmental samples such as, but not limited to, soil, water (fresh water, waste water, etc.), air monitoring system samples (e.g., material captured in an air filter medium), surface swabs, and vectors (e.g., mosquitos, ticks, fleas, etc.).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, mRNA, rRNA, cDNA, gDNA, ssDNA, dsDNA, or any combination thereof.

By "probe," "primer," or "oligonucleotide" is meant a single-stranded nucleic acid molecule of defined sequence that can base-pair to a second nucleic acid molecule that contains a complementary sequence (the "target"). The stability of the resulting hybrid depends upon the length, GC content, and the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes, primers, and oligonucleotides may be detectably-labeled, either radioactively, fluorescently, or non-radioactively, by methods well-known to those skilled in the art. dsDNA binding dyes may be used to detect dsDNA. It is understood that a "primer" is specifically configured to be extended by a polymerase, whereas a "probe" or "oligonucleotide" may or may not be so configured.

By "dsDNA binding dyes" is meant dyes that fluoresce differentially when bound to double-stranded DNA than when bound to single-stranded DNA or free in solution, usually by fluorescing more strongly. While reference is made to dsDNA binding dyes, it is understood that any suitable dye may be used herein, with some non-limiting illustrative dyes described in U.S. Pat. No. 7,387,887, herein incorporated by reference. Other signal producing substances may be used for detecting nucleic acid amplification and melting, illustratively enzymes, antibodies, etc., as are known in the art.

By "specifically hybridizes" is meant that a probe, primer, or oligonucleotide recognizes and physically interacts (that is, base-pairs) with a substantially complementary nucleic acid (for example, a sample nucleic acid) under high stringency conditions, and does not substantially base pair with other nucleic acids.

By "high stringency conditions" is meant typically to occur at about a melting temperature (Tm) minus 5° C. (i.e. 5° below the Tm of the probe). Functionally, high stringency conditions are used to identify nucleic acid sequences having at least 80% sequence identity.

While PCR is the amplification method used in the examples herein, it is understood that any amplification method that uses a primer may be suitable. Such suitable procedures include polymerase chain reaction (PCR); strand displacement amplification (SDA); nucleic acid sequence-based amplification (NASBA); cascade rolling circle amplification (CRCA), loop-mediated isothermal amplification of DNA (LAMP); isothermal and chimeric primer-initiated amplification of nucleic acids (ICAN); target based-helicase dependent amplification (HDA); transcription-mediated amplification (TMA), and the like. Therefore, when the term PCR is used, it should be understood to include other alternative amplification methods. For amplification methods without discrete cycles, reaction time may be used where measurements are made in cycles, doubling time, or crossing point (Cp), and additional reaction time may be added where additional PCR cycles are added in the embodiments described herein. It is understood that protocols may need to be adjusted accordingly.

As used herein, the term "crossing point" (Cp) (or, alternatively, cycle threshold (Ct), quantification cycle (Cq), or a synonymous term used in the art) refers to the number of cycles of PCR required to obtain a fluorescence signal above some threshold value for a given PCR product (e.g., target or internal standard(s)), as determined experimentally. The cycle where each reaction rises above the threshold is dependent on the amount of target (i.e., reaction template) present at the beginning of the PCR reaction. The threshold value may typically be set at the point where the product's fluorescence signal is detectable above background fluorescence; however, other threshold values may be employed. As an alternative to setting a somewhat arbitrary threshold value, Cp may be determined by calculating the point for a reaction at which a first, second, or nth order derivative has its maximum value, which determines the cycle at which the curvature of the amplification curve is maximal. An illustrative derivative method was taught in U.S. Pat. No. 6,303,305, herein incorporated by reference in its entirety. Nevertheless, it usually does not matter much where or how the threshold is set, so long as the same threshold is used for all reactions that are being compared. Other points may be used as well, as are known in the art, and any such point may be substituted for Cp, Ct, or Cq in any of the methods discussed herein.

While various examples herein reference human targets and human pathogens, these examples are illustrative only. Methods, kits, and devices described herein may be used to detect and sequence a wide variety of nucleic acid sequences from a wide variety of samples, including, human, veterinary, industrial, and environmental.

Various embodiments disclosed herein use a self-contained nucleic acid analysis pouch to assay a sample for the presence of various biological substances, illustratively antigens and nucleic acid sequences, illustratively in a single closed system. Such systems, including pouches and instruments for use with the pouches, are disclosed in more detail in U.S. Pat. Nos. 8,394,608; and 8,895,295; and U.S. Patent Application No. 2014-0283945, herein incorporated by reference. However, it is understood that such pouches are illustrative only, and the nucleic acid preparation and amplification reactions discussed herein may be performed in any of a variety of open or closed system sample vessels as are known in the art, including 96-well plates, plates of other configurations, arrays, carousels, and the like, using a variety of nucleic acid purification and amplification systems, as are known in the art.

While the terms "sample well", "amplification well", "amplification container", or the like are used herein, these terms are meant to encompass wells, tubes, and various other reaction containers, as are used in these amplification systems. In one embodiment, the pouch is used to assay for multiple pathogens. The pouch may include one or more blisters used as sample wells, illustratively in a closed system. Illustratively, various steps may be performed in the optionally disposable pouch, including nucleic acid preparation, primary large volume multiplex PCR, dilution of primary amplification product, and secondary PCR, culminating with optional real-time detection or post-amplification analysis such as melting-curve analysis. Further, it is understood that while the various steps may be performed in pouches of the present invention, one or more of the steps may be omitted for certain uses, and the pouch configuration may be altered accordingly.

As used herein, the term "point-of-use" refers to a step that is performed by a system on a device or in a method either immediately before or while the system is in use. For instance, drawing a vacuum on one of more chambers of an assay device at the "point-of-use" means that the vacuum is drawn shortly before (e.g., within an hour or less) performing an assay with the assay device or in situ during or after performing one or more steps of an assay with the assay device. This contrasts with performing a step like drawing an appropriate vacuum at the time of manufacture of the assay device and then storing the device under appropriate vacuum until shortly before the time of use.

FIG. 1 shows an illustrative pouch 510 that may be used in various embodiments, or may be reconfigured for various embodiments. Pouch 510 is similar to FIG. 15 of U.S. Pat. No. 8,895,295, with like items numbered the same. Fitment 590 is provided with entry channels 515a through 515l, which also serve as reagent reservoirs or waste reservoirs. Illustratively, reagents may be freeze dried in fitment 590 and rehydrated prior to use. Blisters 522, 544, 546, 548, 564, and 566, with their respective channels 514, 538, 543, 552, 553, 562, and 565 are similar to blisters of the same number of FIG. 15 of U.S. Pat. No. 8,895,295. Second-stage reaction zone 580 of FIG. 1 is similar to that of U.S. Pat. No. 8,895,295, but the second-stage wells 582 of high density array 581 are arranged in a somewhat different pattern. The more circular pattern of high density array 581 of FIG. 1 eliminates wells in corners and may result in more uniform filling of second-stage wells 582. As shown, the high density array 581 is provided with 102 second-stage wells 582. Pouch 510 is suitable for use in the FilmArray® instrument (BioFire Diagnostics, LLC, Salt Lake City, Utah). However, it is understood that the pouch embodiment is illustrative only.

While other containers may be used, illustratively, pouch 510 may be formed of two layers of a flexible plastic film or other flexible material such as polyester, polyethylene terephthalate (PET), polycarbonate, polypropylene, polymethylmethacrylate, mixtures, combinations, and layers thereof that can be made by any process known in the art, including extrusion, plasma deposition, and lamination. For instance, each layer can be composed of one or more layers of material of a single type or more than one type that are laminated together. Metal foils or plastics with aluminum lamination also may be used. Other barrier materials are known in the art that can be sealed together to form the blisters and channels. If plastic film is used, the layers may be bonded together, illustratively by heat sealing. Illustratively, the material has low nucleic acid binding capacity.

For embodiments employing fluorescent monitoring, plastic films that are adequately low in absorbance and auto-fluorescence at the operative wavelengths are preferred. Such material could be identified by testing different plastics, different plasticizers, and composite ratios, as well as different thicknesses of the film. For plastics with aluminum or other foil lamination, the portion of the pouch that is to be read by a fluorescence detection device can be left without the foil. For example, if fluorescence is monitored in second-stage wells 582 of the second-stage reaction zone 580 of pouch 510, then one or both layers at wells 582 would be left without the foil. In the example of PCR, film laminates composed of polyester (Mylar, DuPont, Wilmington Del.) of about 0.0048 inch (0.1219 mm) thick and polypropylene films of 0.001-0.003 inch (0.025-0.076 mm) thick perform well. Illustratively, pouch 510 may be made of a clear material capable of transmitting approximately 80%-90% of incident light.

In the illustrative embodiment, the materials are moved between blisters by the application of pressure, illustratively pneumatic pressure, upon the blisters and channels. Accordingly, in embodiments employing pressure, the pouch material illustratively is flexible enough to allow the pressure to have the desired effect. The term "flexible" is herein used to describe a physical characteristic of the material of the pouch. The term "flexible" is herein defined as readily deformable by the levels of pressure used herein without cracking, breaking, crazing, or the like. For example, thin plastic sheets, such as Saran™ wrap and Ziploc® bags, as well as thin metal foil, such as aluminum foil, are flexible. However, only certain regions of the blisters and channels need be flexible, even in embodiments employing pneumatic pressure. Further, only one side of the blisters and channels need to be flexible, as long as the blisters and channels are readily deformable. Other regions of the pouch 510 may be made of a rigid material or may be reinforced with a rigid material. Thus, it is understood that when the terms "flexible pouch" or "flexible sample container" or the like are used, only portions of the pouch or sample container need be flexible.

Illustratively, a plastic film may be used for pouch 510. A sheet of metal, illustratively aluminum, or other suitable material, may be milled or otherwise cut, to create a die having a pattern of raised surfaces. When fitted into a pneumatic press (illustratively A-5302-PDS, Janesville Tool Inc., Milton Wis.), illustratively regulated at an operating temperature of 195° C., the pneumatic press works like a printing press, melting the sealing surfaces of plastic film only where the die contacts the film. Likewise, the plastic film(s) used for pouch 510 may be cut and welded together using a laser cutting and welding device. Various components, such as PCR primers (illustratively spotted onto the film and dried), antigen binding substrates, magnetic beads, and zirconium silicate beads may be sealed inside various blisters as the pouch 510 is formed. Reagents for sample processing can be spotted onto the film prior to sealing, either collectively or separately. In one embodiment, nucleotide tri-phosphates (NTPs) are spotted onto the film separately from polymerase and primers, essentially eliminating activity of the polymerase until the reaction may be hydrated by an aqueous sample. If the aqueous sample has been heated prior to hydration, this creates the conditions for a true hot-start PCR and reduces or eliminates the need for expensive chemical hot-start components. In another embodiment, components may be provided in powder or pill form and are placed into blisters prior to final sealing.

Pouch 510 may be used in a manner similar to that described in U.S. Pat. No. 8,895,295. In one illustrative embodiment, a 300 µl mixture comprising the sample to be tested (100 µl) and lysis buffer (200 µl) may be injected into an injection port (not shown) in fitment 590 near entry channel 515a, and the sample mixture may be drawn into entry channel 515a. Water may also be injected into a second injection port (not shown) of the fitment 590 adjacent entry channel 515l, and is distributed via a channel (not shown) provided in fitment 590, thereby hydrating up to eleven different reagents, each of which were previously provided in dry form at entry channels 515b through 515l. Illustrative methods and devices for injecting sample and hydration fluid (e.g. water or buffer) are disclosed in U.S. Patent Application No. 2014-0283945, herein incorporated by reference in its entirety, although it is understood that these methods and devices are illustrative only and other ways of introducing sample and hydration fluid into pouch 510 are within the scope of this disclosure. These reagents illustratively may include freeze-dried PCR reagents, DNA extraction reagents, wash solutions, immunoassay reagents, or other chemical entities. Illustratively, the reagents are for nucleic acid extraction, first-stage multiplex PCR, dilution of the multiplex reaction, and preparation of second-stage PCR reagents, as well as control reactions. In the embodiment shown in FIG. 1, all that need be injected is the sample solution in one injection port and water in the other injection port. After injection, the two injection ports may be sealed. For more information on various configurations of pouch 510 and fitment 590, see U.S. Pat. No. 8,895,295, already incorporated by reference.

After injection, the sample may be moved from injection channel 515a to lysis blister 522 via channel 514. Lysis blister 522 is provided with beads or particles 534, such as ceramic beads or other abrasive elements, and is configured for vortexing via impaction using rotating blades or paddles provided within the FilmArray® instrument. Bead-milling, by shaking, vortexing, sonicating, and similar treatment of the sample in the presence of lysing particles such as zirconium silicate (ZS) beads 534, is an effective method to form a lysate. It is understood that, as used herein, terms such as "lyse," "lysing," and "lysate" are not limited to rupturing cells, but that such terms include disruption of non-cellular particles, such as viruses.

Figure 2:
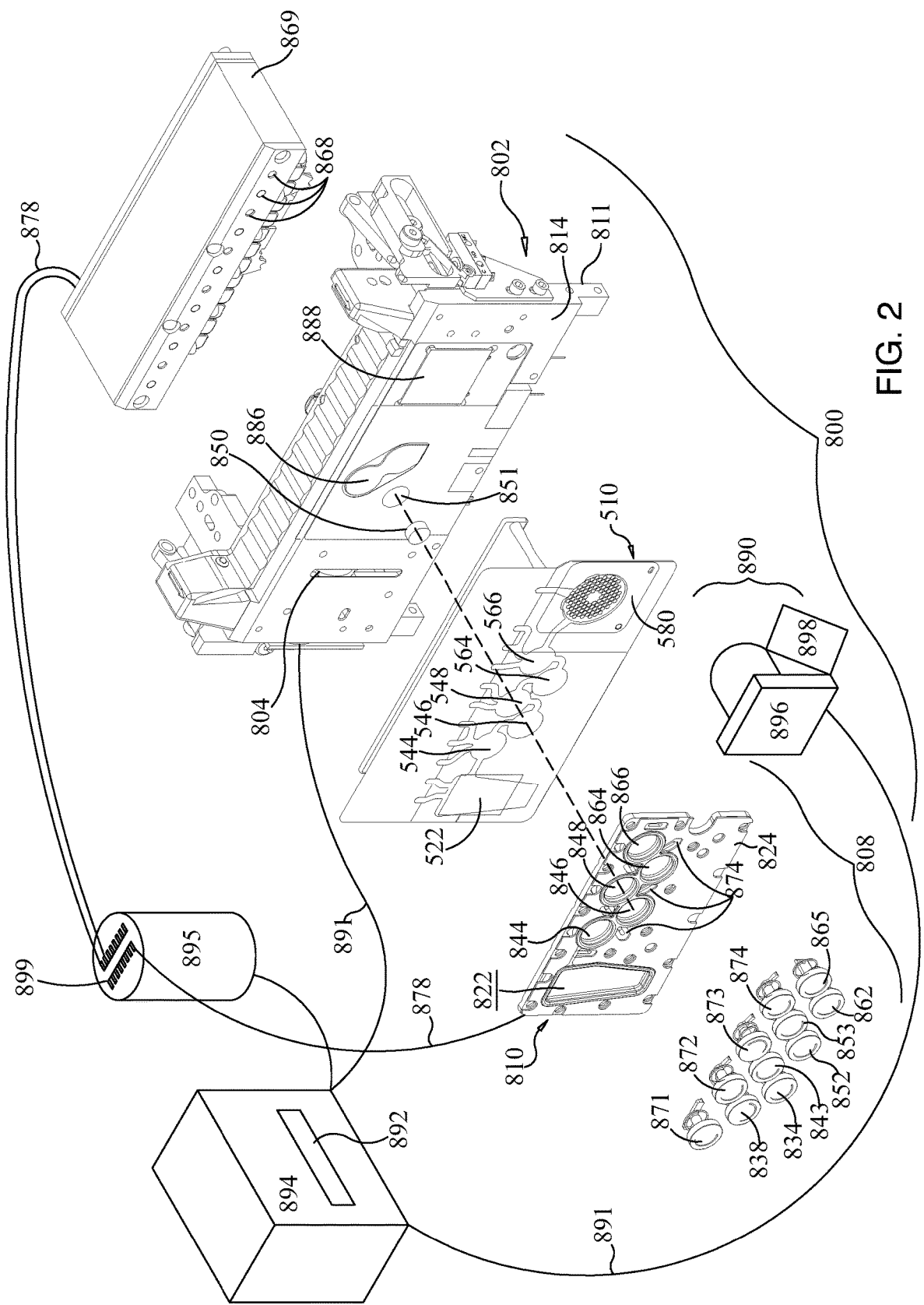
FIG. 2 is an exploded perspective view of an instrument for use with the pouch of FIG. 1, including the pouch of FIG. 1.

FIG. 4 shows a bead beating motor 819, comprising blades 821 that may be mounted on a first side 811 of support member 802, of instrument 800 shown in FIG. 2. Blades may extend through slot 804 to contact pouch 510. It is understood, however, that motor 819 may be mounted on other structures of instrument 800. In one illustrative embodiment, motor 819 is a Mabuchi RC-280SA-2865 DC Motor (Chiba, Japan), mounted on support member 802. In one illustrative embodiment, the motor is turned at 5,000 to 25,000 rpm, more illustratively 10,000 to 20,000 rpm, and still more illustratively approximately 15,000 to 18,000 rpm. For the Mabuchi motor, it has been found that 7.2V provides sufficient rpm for lysis. It is understood, however, that the actual speed may be somewhat slower when the blades 821 are impacting pouch 510. Other voltages and speeds may be used for lysis depending on the motor and paddles used. Optionally, controlled small volumes of air may be provided into the bladder 822 adjacent lysis blister 522. It has been found that in some embodiments, partially filling the adjacent bladder with one or more small volumes of air aids in positioning and supporting lysis blister during the lysis process. Alternatively, other structure, illustratively a rigid or compliant gasket or other retaining structure around lysis blister 522, can be used to restrain pouch 510 during lysis. It is also understood that motor 819 is illustrative only, and other devices may be used for milling, shaking, or vortexing the sample. In some embodiments, chemicals or heat may be used in addition to or instead of mechanical lysis.

Once the sample material has been adequately lysed, the sample is moved to a nucleic acid extraction zone, illustratively through channel 538, blister 544, and channel 543, to blister 546, where the sample is mixed with a nucleic acid-binding substance, such as silica-coated magnetic beads 533. Alternatively, magnetic beads 533 may be rehydrated, illustratively using fluid provided from one of the entry channel 515c-515e, and then moved through channel 543 to blister 544, and then through channel 538 to blister 522. The mixture is allowed to incubate for an appropriate length of time, illustratively approximately 10 seconds to 10 minutes. A retractable magnet located within the instrument adjacent blister 546 captures the magnetic beads 533 from the solution, forming a pellet against the interior surface of blister 546. If incubation takes place in blister 522, multiple portions of the solution may need to be moved to blister 546 for capture. The liquid is then moved out of blister 546 and back through blister 544 and into blister 522, which is now used as a waste receptacle. One or more wash buffers from one or more of injection channels 515c to 515e are provided via blister 544 and channel 543 to blister 546. Optionally, the magnet is retracted and the magnetic beads 533 are washed by moving the beads back and forth from blisters 544 and 546 via channel 543. Once the magnetic beads 533 are washed, the magnetic beads 533 are recaptured in blister 546 by activation of the magnet, and the wash solution is then moved to blister 522. This process may be repeated as necessary to wash the lysis buffer and sample debris from the nucleic acid-binding magnetic beads 533.

After washing, elution buffer stored at injection channel 515f is moved to blister 548, and the magnet is retracted. The solution is cycled between blisters 546 and 548 via channel 552, breaking up the pellet of magnetic beads 533 in blister 546 and allowing the captured nucleic acids to dissociate from the beads and come into solution. The magnet is once again activated, capturing the magnetic beads 533 in blister 546, and the eluted nucleic acid solution is moved into blister 548.

First-stage PCR master mix from injection channel 515g is mixed with the nucleic acid sample in blister 548. Optionally, the mixture is mixed by forcing the mixture between 548 and 564 via channel 553. After several cycles of mixing, the solution is contained in blister 564, where a pellet of first-stage PCR primers is provided, at least one set of primers for each target, and first-stage multiplex PCR is performed. If RNA targets are present, an RT step may be performed prior to or simultaneously with the first-stage multiplex PCR. First-stage multiplex PCR temperature cycling in the FilmArray® instrument is illustratively performed for 15-20 cycles, although other levels of amplification may be desirable, depending on the requirements of the specific application. The first-stage PCR master mix may be any of various master mixes, as are known in the art. In one illustrative example, the first-stage PCR master mix may be any of the chemistries disclosed in U.S. Pat. No. 9,932,634, herein incorporated by reference, for use with PCR protocols taking 20 seconds or less per cycle.

After first-stage PCR has proceeded for the desired number of cycles, the sample may be diluted, illustratively by forcing most of the sample back into blister 548, leaving only a small amount in blister 564, and adding second-stage PCR master mix from injection channel 515i. Alternatively, a dilution buffer from 515i may be moved to blister 566 then mixed with the amplified sample in blister 564 by moving the fluids back and forth between blisters 564 and 566. If desired, dilution may be repeated several times, using dilution buffer from injection channels 515j and 515k, or injection channel 515k may be reserved, illustratively, for sequencing or for other post-PCR analysis, and then adding second-stage PCR master mix from injection channel 515h to some or all of the diluted amplified sample. It is understood that the level of dilution may be adjusted by altering the number of dilution steps or by altering the percentage of the sample discarded prior to mixing with the dilution buffer or second-stage PCR master mix comprising components for amplification, illustratively a polymerase, dNTPs, and a suitable buffer, although other components may be suitable, particularly for non-PCR amplification methods. If desired, this mixture of the sample and second-stage PCR master mix may be pre-heated in blister 564 prior to movement to second-stage wells 582 for second-stage amplification. Such preheating may obviate the need for a hot-start component (antibody, chemical, or otherwise) in the second-stage PCR mixture.

The illustrative second-stage PCR master mix is incomplete, lacking primer pairs, and each of the 102 second-stage wells 582 is pre-loaded with a specific PCR primer pair. If desired, second-stage PCR master mix may lack other reaction components, and these components may be pre-loaded in the second-stage wells 582 as well. Each primer pair may be similar to or identical to a first-stage PCR primer pair or may be nested within the first-stage primer pair. Movement of the sample from blister 564 to the second-stage wells 582 completes the PCR reaction mixture. Once high density array 581 is filled, the individual second-stage reactions are sealed in their respective second-stage blisters by any number of means, as is known in the art. Illustrative ways of filling and sealing the high density array 581 without cross-contamination are discussed in U.S. Pat. No. 8,895,295, already incorporated by reference. Illustratively, the various reactions in wells 582 of high density array 581 are simultaneously or individually thermal cycled, illustratively with one or more Peltier devices, although other means for thermal cycling are known in the art.

In certain embodiments, second-stage PCR master mix contains the dsDNA binding dye LCGreen® Plus (BioFire Diagnostics, LLC) to generate a signal indicative of amplification. However, it is understood that this dye is illustrative only, and that other signals may be used, including other dsDNA binding dyes and probes that are labeled fluorescently, radioactively, chemiluminescently, enzymatically, or the like, as are known in the art. Alternatively, wells 582 of array 581 may be provided without a signal, with results reported through subsequent processing.

Figure 3:
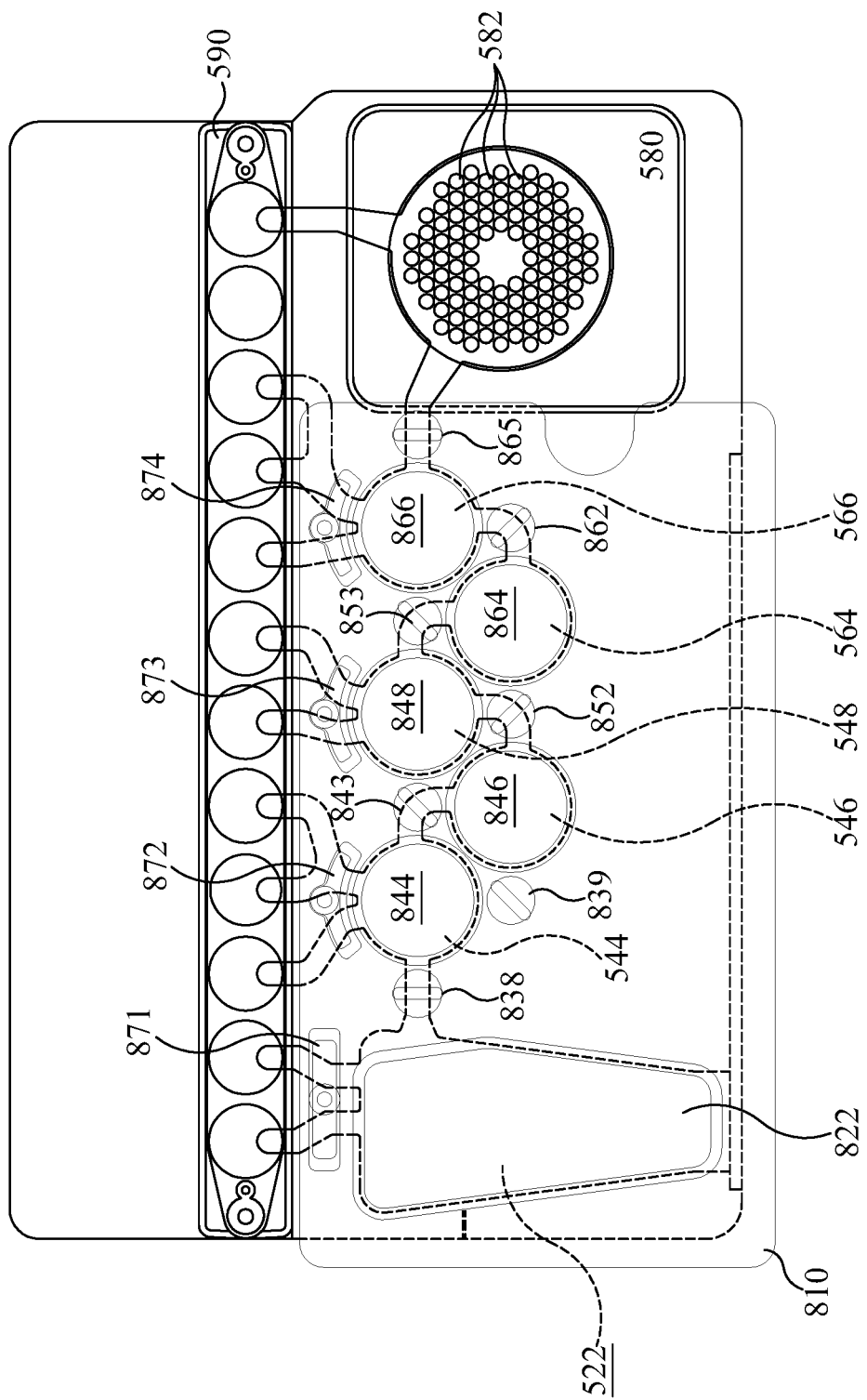
FIG. 3 shows a partial cross-sectional view of the instrument of FIG. 3A, including the bladder components of FIG. 2, with the pouch of FIG. 1.

When pneumatic pressure is used to move materials within pouch 510, in one embodiment, a "bladder" may be employed. The bladder assembly 810, a portion of which is shown in FIGS. 2-3, includes a bladder plate 824 housing a plurality of inflatable bladders 822, 844, 846, 848, 864, and 866, each of which may be individually inflatable, illustratively by a compressed gas source. Because the bladder assembly 810 may be subjected to compressed gas and used multiple times, the bladder assembly 810 may be made from tougher or thicker material than the pouch. Alternatively, bladders 822, 844, 846, 848, 864, and 866 may be formed from a series of plates fastened together with gaskets, seals, valves, and pistons. Other arrangements are within the scope of this invention. Alternatively, an array or mechanical actuators and seals may be used to seal channels and direct movement of fluids between blisters. A system of mechanical seals and actuators that may be adapted for the instruments described herein is described in detail in WO 2018/022971, the entirety of which is incorporated herein by reference.

Success of the secondary PCR reactions is dependent upon template generated by the multiplex first-stage reaction. Typically, PCR is performed using DNA of high purity. Methods such as phenol extraction or commercial DNA extraction kits provide DNA of high purity. Samples processed through the pouch 510 may require accommodations be made to compensate for a less pure preparation. PCR may be inhibited by components of biological samples, which is a potential obstacle. Illustratively, hot-start PCR, higher concentration of Taq polymerase enzyme, adjustments in $MgCl_2$ concentration, adjustments in primer concentration, and addition of adjuvants (such as DMSO, TMSO, or glycerol) optionally may be used to compensate for lower nucleic acid purity. While purity issues are likely to be more of a concern with first-stage amplification, it is understood that similar adjustments may be provided in the second-stage amplification as well.

When pouch 510 is placed within the instrument 800, the bladder assembly 810 is pressed against one face of the pouch 510, so that if a particular bladder is inflated, the pressure will force the liquid out of the corresponding blister in the pouch 510. In addition to bladders corresponding to many of the blisters of pouch 510, the bladder assembly 810 may have additional pneumatic actuators, such as bladders or pneumatically-driven pistons, corresponding to various channels of pouch 510. FIGS. 2-3 show an illustrative plurality of pistons or hard seals 838, 843, 852, 853, and 865 that correspond to channels 538, 543, 553, and 565 of pouch 510, as well as seals 871, 872, 873, 874 that minimize backflow into fitment 590. When activated, hard seals 838, 843, 852, 853, and 865 form pinch valves to pinch off and close the corresponding channels. To confine liquid within a particular blister of pouch 510, the hard seals are activated over the channels leading to and from the blister, such that the actuators function as pinch valves to pinch the channels shut. Illustratively, to mix two volumes of liquid in different blisters, the pinch valve actuator sealing the connecting channel is activated, and the pneumatic bladders over the blisters are alternately pressurized, forcing the liquid back and forth through the channel connecting the blisters to mix the liquid therein. The pinch valve actuators may be of various shapes and sizes and may be configured to pinch off more than one channel at a time. While pneumatic actuators are discussed herein, it is understood that other ways of providing pressure to the pouch are contemplated, including various electromechanical actuators such as linear stepper motors, motor-driven cams, rigid paddles driven by pneumatic, hydraulic or electromagnetic forces, rollers, rocker-arms, and in some cases, cocked springs. In addition, there are a variety of methods of reversibly or irreversibly closing channels in addition to applying pressure normal to the axis of the channel. These include kinking the bag across the channel, heat-sealing, rolling an actuator, and a variety of physical valves sealed into the channel such as butterfly valves and ball valves. Additionally, small Peltier devices or other temperature regulators may be placed adjacent the channels and set at a temperature sufficient to freeze the fluid, effectively forming a seal. Also, while the design of FIG. 1 is adapted for an automated instrument featuring actuator elements positioned over each of the blisters and channels, it is also contemplated that the actuators could remain stationary, and the pouch 510 could be transitioned such that a small number of actuators could be used for several of the processing stations including sample disruption, nucleic-acid capture, first and second-stage PCR, and processing stations for other applications of the pouch 510 such as immuno-assay and immuno-PCR. Rollers acting on channels and blisters could prove particularly useful in a configuration in which the pouch 510 is translated between stations. Thus, while pneumatic actuators are used in the presently disclosed embodiments, when the term "pneumatic actuator" is used herein, it is understood that other actuators and other ways of providing pressure may be used, depending on the configuration of the pouch and the instrument.

Turning back to FIG. 2, each pneumatic actuator is connected to compressed air source 895 via valves 899. While only several hoses 878 are shown in FIG. 2, it is understood that each pneumatic fitting is connected via a hose 878 to the compressed gas source 895. Compressed gas source 895 may be a compressor, or, alternatively, compressed gas source 895 may be a compressed gas cylinder, such as a carbon dioxide cylinder. Compressed gas cylinders are particularly useful if portability is desired. Other sources of compressed gas are within the scope of this invention. Similar pneumatic control may be provided in the embodiments of FIGS. 12-16, for control of fluids in pouch 1400, or other actuators, servos, or the like may be provided.

Several other components of instrument 810 are also connected to compressed gas source 895. A magnet 850, which is mounted on a second side 814 of support member 802, is illustratively deployed and retracted using gas from compressed gas source 895 via hose 878, although other methods of moving magnet 850 are known in the art. Magnet 850 sits in recess 851 in support member 802. It is understood that recess 851 can be a passageway through support member 802, so that magnet 850 can contact blister 546 of pouch 510. However, depending on the material of support member 802, it is understood that recess 851 need not extend all the way through support member 802, as long as when magnet 850 is deployed, magnet 850 is close enough to provide a sufficient magnetic field at blister 546, and when magnet 850 is fully retracted, magnet 850 does not significantly affect any magnetic beads 533 present in blister 546. While reference is made to retracting magnet 850, it is understood that an electromagnet may be used and the electromagnet may be activated and inactivated by controlling flow of electricity through the electromagnet. Thus, while this specification discusses withdrawing or retracting the magnet, it is understood that these terms are broad enough to incorporate other ways of withdrawing the magnetic field. It is understood that the pneumatic connections may be pneumatic hoses or pneumatic air manifolds, thus reducing the number of hoses or valves required. It is understood that similar magnets and methods for activating the magnets may be used in the embodiments of FIGS. 12-16.

The various pneumatic pistons 868 of pneumatic piston array 869 are also connected to compressed gas source 895 via hoses 878. While only two hoses 878 are shown connecting pneumatic pistons 868 to compressed gas source 895, it is understood that each of the pneumatic pistons 868 are connected to compressed gas source 895. Twelve pneumatic pistons 868 are shown.

A pair of temperature control elements are mounted on a second side 814 of support 802. As used herein, the term "temperature control element" refers to a device that adds heat to or removes heat from a sample. Illustrative examples of a temperature control element include, but are not limited to, heaters, coolers, Peltier devices, resistance heaters, induction heaters, electromagnetic heaters, thin film heaters, printed element heaters, positive temperature coefficient heaters, and combinations thereof. A temperature control element may include multiple heaters, coolers, Peltiers, etc. In one aspect, a given temperature control element may include more than one type of heater or cooler. For instance, an illustrative example of a temperature control element may include a Peltier device with a separate resistive heater applied to the top and/or the bottom face of the Peltier. While the term "heater" is used throughout the specification, it is understood that other temperature control elements may be used to adjust the temperature of the sample.

As discussed above, first-stage heater 886 may be positioned to heat and cool the contents of blister 564 for first-stage PCR. As seen in FIG. 2, second-stage heater 888 may be positioned to heat and cool the contents of second-stage blisters 582 of array 581 of pouch 510, for second-stage PCR. It is understood, however, that these heaters could also be used for other heating purposes, and that other heaters may be included, as appropriate for the particular application.

As discussed above, while Peltier devices, which thermo-cycle between two or more temperatures, are effective for PCR, it may be desirable in some embodiments to maintain heaters at a constant temperature. Illustratively, this can be used to reduce run time, by eliminating time needed to transition the heater temperature beyond the time needed to transition the sample temperature. Also, such an arrangement can improve the electrical efficiency of the system as it is only necessary to thermally cycle the smaller sample and sample vessel, not the much larger (more thermal mass) Peltier devices. For instance, an instrument may include multiple heaters (i.e., two or more) at temperatures set for, for example, annealing, elongation, denaturation that are positioned relative to the pouch to accomplish thermal cycling. Two heaters may be sufficient for many applications. In various embodiments, the heaters can be moved, the pouch can be moved, or fluids can be moved relative to the heaters to accomplish thermal cycling. Illustratively, the heaters may be arranged linearly, in a circular arrangement, or the like. Types of suitable heaters have been discussed above, with reference to first-stage PCR.

When fluorescent detection is desired, an optical array 890 may be provided. As shown in FIG. 2, optical array 890 includes a light source 898, illustratively a filtered LED light source, filtered white light, or laser illumination, and a camera 896. Camera 896 illustratively has a plurality of photodetectors each corresponding to a second-stage well 582 in pouch 510. Alternatively, camera 896 may take images that contain all of the second-stage wells 582, and the image may be divided into separate fields corresponding to each of the second-stage wells 582. Depending on the configuration, optical array 890 may be stationary, or optical array 890 may be placed on movers attached to one or more motors and moved to obtain signals from each individual second-stage well 582. It is understood that other arrangements are possible. The embodiment for second-stage heaters shown in FIG. 18 provides the heaters on the opposite side of pouch 510 from that shown in FIG. 2. Such orientation is illustrative only and may be determined by spatial constraints within the instrument. Provided that second-stage reaction zone 580 is provided in an optically transparent material, photodetectors and heaters may be on either side of array 581.

As shown, a computer 894 controls valves 899 of compressed air source 895, and thus controls all of the pneumatics of instrument 800. In addition, many of the pneumatic systems in the instrument may be replaced with mechanical actuators, pressure applying means, and the like in other embodiments. Computer 894 also controls heaters 886 and 888, and optical array 890. Each of these components is connected electrically, illustratively via cables 891, although other physical or wireless connections are within the scope of this invention. It is understood that computer 894 may be housed within instrument 800 or may be external to instrument 800. Further, computer 894 may include built-in circuit boards that control some or all of the components, and may also include an external computer, such as a desktop or laptop PC, to receive and display data from the optical array. An interface, illustratively a keyboard interface, may be provided including keys for inputting information and variables such as temperatures, cycle times, etc. Illustratively, a display 892 is also provided. Display 892 may be an LED, LCD, or other such display, for example.

Other prior art instruments teach PCR within a sealed flexible container. See, e.g., U.S. Pat. Nos. 6,645,758, 6,780,617, and 9,586,208, herein incorporated by reference. However, including the cell lysis within the sealed PCR vessel can improve ease of use and safety, particularly if the sample to be tested may contain a biohazard. In the embodiments illustrated herein, the waste from cell lysis, as well as that from all other steps, remains within the sealed pouch. Still, it is understood that the pouch contents could be removed for further testing.

FIG. 2 shows an illustrative instrument 800 that could be used with pouch 510. Instrument 800 includes a support member 802 that could form a wall of a casing or be mounted within a casing. Instrument 800 may also include a second support member (not shown) that is optionally movable with respect to support member 802, to allow insertion and withdrawal of pouch 510. Illustratively, a lid may cover pouch 510 once pouch 510 has been inserted into instrument 800. In another embodiment, both support members may be fixed, with pouch 510 held into place by other mechanical means or by pneumatic pressure.

In the illustrative example, heaters 886 and 888 are mounted on support member 802. However, it is understood that this arrangement is illustrative only and that other arrangements are possible. Illustrative heaters include Peltiers and other block heaters, resistance heaters, electromagnetic heaters, and thin film heaters, as are known in the art, to thermocycle the contents of blister 864 and second-stage reaction zone 580. Bladder plate 810, with bladders 822, 844, 846, 848, 864, 866, hard seals 838, 843, 852, 853, and seals 871, 872, 873, 874 form bladder assembly 808, which may illustratively be mounted on a moveable support structure that may be moved toward pouch 510, such that the pneumatic actuators are placed in contact with pouch 510. When pouch 510 is inserted into instrument 800 and the movable support member is moved toward support member 802, the various blisters of pouch 510 are in a position adjacent to the various bladders of bladder assembly 810 and the various seals of assembly 808, such that activation of the pneumatic actuators may force liquid from one or more of the blisters of pouch 510 or may form pinch valves with one or more channels of pouch 510. The relationship between the blisters and channels of pouch 510 and the bladders and seals of assembly 808 is illustrated in more detail in FIG. 3.

FIG. 5A shows another illustrative embodiment of a pouch 5000 (also referred to herein as a 'science card') that may be used in various embodiments, or may be reconfigured for various embodiments described herein for PCR, microbial testing, or for a variety of other tests. The pouch 5000 may be configured for use in an instrument described in WO 2017/147085, herein incorporated by reference, or in a variety of other instruments. The illustrative pouch 5000 of FIG. 5A includes a number of zones or blisters where sample preparation, nucleic acid amplification, and detection can occur. The illustrative pouch 5000 may include a sample preparation blister 5005 where a sample containing nucleic acids to be amplified and analyzed may be introduced into the pouch 5000, a first-stage PCR blister 5010, a volumetric dilution well 5015 for measuring a portion of the product from first-stage PCR prior to second-stage PCR, and a second-stage PCR array 5081 that includes a number of individual reaction wells 5082. The volumetric well 5015 may also be fluidly coupled to blisters 5020 and 5025, where reagents for second-stage PCR may be introduced and mixed with the contents of the dilution well 5015. In one example, a sample for second-stage PCR may be prepared by repeatedly mixing the contents of volumetric well 5015 with reagents for second-stage PCR between blisters 5020 and 5025. The second-stage array 5081 may also be fluidly connected to a waste receptacle 5035. Alternatively, blister 5010 may be used for both sample preparation and first-stage PCR and blister 5005 may be used as a waste receptacle for, for example, sample preparation waste(s).

Blisters 5005, 5010, 5020, and 5025, dilution well 5015, and second-stage array 5081 may be fluidly connected by channels 5050*a*-5050*e*. Sample and reagent may be entered into the pouch 5000 via entry channels 5040*a*-5040*f* and entry ports 5045*a*-5045*f*. Alternatively, pouch 5000 may be fitted with a device similar in form to fitment 590 of FIG. 1 for introduction of sample and reagents into the pouch 5000. In addition, the pouch 5000 may include dehydrated (e.g., freeze dried) reagents in a fitment or a similar structure that may be hydrated with a suitable hydration buffer prior to use of the pouch. In yet another embodiment, liquid reagents may be provided in pouch 5000.

In one embodiment, the pouch 5000 may be fabricated from a number of layers of material (layers of the same material or layers of different types of material) that are sealed together to form the pouch 5000. In FIGS. 5B and 5C, cutaway views are shown along the lines B-B and C-C illustrating layers of material that may be used to fabricate different parts of the pouch 5000. In one region of the pouch 5000 illustrated in FIG. 5B, the illustrative pouch 5000 may be fabricated from a first layer of film 5090 that is bonded to a second layer of film 5098. Layers 5090 and 5098 may be bonded together by any conventional means known in the art such as, but not limited to, heat and pressure, sonic welding, or laser welding. FIG. 5B also illustrates that a blister or a channel (e.g., channel 5040c) may be formed in the pouch 5000 by leaving an open area between the film layers 5090 and 5098 and defining the boundaries of the open area with sealed margins along the opening—an illustrative weld is shown at 5084 in FIGS. 5A and 5B. FIG. 5C illustrates another region of the pouch 5000 that includes a thick card material that may be used to form the wells of the second-stage array 5081. This region of the illustrative pouch 5000 may be fabricated from a first film layer 5090, a pressure sensitive adhesive layer 5092, a card layer 5094, a second pressure sensitive adhesive layer 5096, and a second film layer 5098. In one illustrative example, the wells 5082 of the second-stage array 5081 may be formed in the card layer 5094. In an alternative to forming the channels (e.g., channel 5040c) and blisters (e.g., blister 5005) by leaving open space between the film layers (e.g., film layers 5090 and 5098) as illustrated in FIG. 5B, the card 5094 layer could be extended and the blisters and/or the channels could be formed by making appropriate cutouts in the card layer 5094. Likewise, channels 5050a-5050e and entry channels 5040a-5040f may be formed by making appropriate cutouts in the either the first or second pressure sensitive adhesive layers 5092 and 5096. One will appreciate that other configurations are possible. It is understood that while the illustrative blister areas are flexible, the card layer 5094 optionally may be less flexible and may be rigid, and still be part of a flexible sample container. Thus, it is understood that a "flexible pouch" need only be flexible in certain zones. Alternatively or in addition, flow channels between the blister areas can be formed by adding another film layer, tubing, or rigid layer above film layer 5090 or below film layer 5098 and welding the layers together, leaving open blister areas and channels between the layers.

While other materials may be used, illustratively, the film layers of pouch 5000 may be formed from a flexible plastic film or other flexible material similar to the pouch 510 described in FIG. 1. For instance, pouch 5000 may be fabricated from materials such as, but not limited to, such as polyester, polyethylene terephthalate (PET), polycarbonate, polypropylene (PP), polymethylmethacrylate, combinations, mixtures, and laminated layers thereof that can be made by any process known in the art, including extrusion, plasma deposition, and lamination. Similar materials (e.g., polycarbonate) may be used for the card layer 5094. Other materials, including metal foils or plastics with aluminum lamination, may also be used. Other barrier materials are known in the art that can be sealed together to form the blisters and channels. If plastic film is used, the layers may be bonded together, illustratively by heat sealing or laser welding. Illustratively, the material has low nucleic acid binding capacity. If fluorescence detection is used, optically transparent material may be used in the appropriate areas of the pouch (e.g., in the vicinity of the second-stage array).

In addition to or in lieu of the foregoing examples of film materials, a barrier film may be used in one or more of the layers used to form pouch 5000 or any of the other pouches described herein. For instance, barrier films may be desirable for some applications because they have low water vapor and/or oxygen transmission rates that may be lower than conventional plastic films. For example, typical barrier films have water vapor transmission rates (WVTR) in a range of about 0.01 g/m$^2$/24 hrs to about 3 g/m$^2$/24 hrs, preferably in a range of about 0.05 g/m$^2$/24 hrs to about 2 g/m$^2$/24 hrs (e.g., no more than about 1 g/m$^2$/24 hrs) and oxygen transmission rates in a range of about 0.01 cc/m$^2$/24 hrs to about 2 cc/m$^2$/24 hrs, preferably in a range of about 0.05 cc/m$^2$/24 hrs to about 2 cc/m$^2$/24 hrs (e.g., no more than about 1 cc/m$^2$/24 hrs). Examples of barrier films include, but are not limited to, films that can be metallized by vapor deposition of a metal (e.g., aluminum or another metal) or sputter coated with an oxide (e.g., $Al_2O_3$ or $SiO_x$) or another chemical composition. A common example of a metallized film is aluminized Mylar, which is metal coated biaxially oriented PET (BoPET). In some applications, coated barrier films can be laminated with a layer of polyethylene, PP, or a similar thermoplastic, which provides sealability and improves puncture resistance. As with conventional plastic films, barrier films layers used to fabricate a pouch may be bonded together, illustratively by heat sealing. Illustratively, the material has low nucleic acid binding and low protein binding capacity. Other barrier materials are known in the art that can be sealed together to form the blisters and channels.

Pouch 5000 may be used in a manner similar to that described above for pouch 510 and/or in a manner similar to that described in U.S. Pat. No. 8,895,295. Referring again to FIG. 5A, two alternative sequences for filling the pouch, preparing a sample, performing first-stage PCR, and performing second-stage PCR are described. In a first example method, sample preparation and first-stage PCR may be performed in separate blisters. This is referred to herein as the "three zone method," with the three zones being sample preparation, first-stage PCR, and second-stage PCR. In the following examples describing the "three zone method" and the "two-zone method," one will appreciate that pouch 5000 is one embodiment of a pouch and that other pouch configurations may be adapted to the three- and/or two-zone methods.

In a first step, a sample is injected into blister 5005 via fill channel 5040a. In one embodiment, cells, viruses, and the like may be lysed in blister 5005 using the wiping system described in detail elsewhere herein. Alternatively, cell lysis may be accomplished with an alternative lysis device such as, but not limited to, a sonication device or a bead beater or by chemical lysis. Optionally, lysis may be aided by heating the sample (e.g., to about 70-90° C.) with one or more heater elements of the heater assembly described in detail elsewhere herein. Following lysis, the sample may be cooled with a thermoelectric cooler element (i.e., a Peltier element) to a temperature in a range of about 0° C. to about 20° C. (e.g., about 10-15° C.) to aid in nucleic acid recovery with, for example, silica-coated magnetic beads. Other cooler elements include, but are not limited to, fluid or gas heat exchange elements, fan cooled heat sinks, heat pipes, condensation units, and the like.

Magnetic beads may be injected into blister 5005 via fill channel 5040a or 5040b for use in recovering nucleic acids from the lysate. Alternatively, cells to be lysed, lysis beads, magnetic beads, lysis buffer, and the like may be injected together or sequentially into blister 5005 prior to lysis. Illustratively, the magnetic beads and the lysate may be mixed cold (e.g., in a range of about 0-10° C., illustratively by adjusting the temperature of one of the heaters). Once the magnetic beads and the lysate have been thoroughly mixed for a sufficient time, the magnetic beads may be gathered in blister 5005 with a magnet illustratively provided in the instrument and the spent lysate may be sent to liquid waste via channel 5040b. Then wash buffer may be injected via fill channel 5040a. The wash buffer and the magnetic beads may be mixed cold (e.g., in a range of about 0-10° C.). The magnetic beads may be gathered again and the spent wash buffer may be flushed to liquid waste via channel 5040b. The wash cycle may be repeated at least one more time. Following the wash, an elution buffer (optionally including first-stage PCR primers) may be injected into blister 5005 via fill channel 5040a. The elution buffer (plus first-stage PCR primers) and the magnetic beads optionally may be mixed hot (e.g., at about 70-90° C.), illustratively, under control of one or more heaters.

For first-stage PCR, PCR master mix (e.g., a polymerase, dNTPs, and other amplification components known in the art) may be injected into blister 5010 via fill channel 5040c. The PCR master mix may be heated (e.g., to about 57° C.) prior to introduction of the eluate from the magnetic beads. In blister 5005, the magnetic beads may be gathered again and the eluate may be sent to blister 5010 via channel 5050a.

In one embodiment, first-stage PCR may be performed in blister 5010 with rotary movement of a wiper system illustrated in WO 2017/147085, already incorporated by reference, illustratively under temperature control of two heaters. Alternatively, first-stage PCR thermocycling may be performed by translating a heater assembly or the pouch 5000 so that blister 5010 may be under control of one heater and then another of a heater assembly that includes two different heaters at two different temperatures (e.g., at an annealing and at a denaturation temperature). The channels into and out of blister 5010 may be closed, illustratively with seals similar to those described in reference to FIGS. 2 and 3, during first stage PCR. In some embodiments, it may be possible to speed up first-stage PCR in the pouch by employing a volume reduction protocol. For instance, a volume reduction protocol may include performing several cycles (e.g., 1-10) of PCR with an initial volume (e.g., ~100 μL) in blister 5010, purging approximately half the volume of blister 5010, performing several more cycles of PCR (e.g., 5-10), and again purging approximately half the volume of blister 5010. Volume reduction can reduce the cycle time for a PCR reaction because smaller volumes of liquid have less thermal mass and can be thermocycled more quickly than larger volumes.

Following a sufficient number of cycles of first-stage PCR (e.g., 20-30 cycles), a small sample (e.g., ~1-5 μL) of first-stage PCR may be sent to dilution well 5015 via channel 5050b; channels 5050c-5050e may be closed. The sample for second-stage PCR may be prepared by injecting a second-stage PCR master mix into blister 5025 via channel 5040e. Seals channels 5050b and 5050e may be closed, seals 5050c and 5050d may be opened and the sample in well 5015 may be mixed with the master mix by mixing between blisters 5025 and 5020 and well 5015 to dilute first-stage PCR product for second-stage PCR. Blisters 5020 and 5025 and well 5015 may be heated prior to or during mixing for a physical "hot-start." Channel 5050e is then opened and seals 5050c and 5050d may be closed so that the second-stage PCR mix can be transferred into the second-stage PCR array 5081. In another embodiment, the pouch 5000 may include one or more additional dilution wells and sets of mixing blisters downstream from well 5015 and blisters 5025 and 5020 and upstream from array 5081. For example, in some embodiments with concentrated first-stage PCR primers or with highly concentrated product, it may be desirable to dilute the first-stage primers and product to a degree greater than can be achieved with one dilution well. Thermocycling for second-stage PCR in array 5081 may illustratively be accomplished by translating the heater assembly back and forth as described in detail elsewhere herein.

In the second exemplary method, sample preparation and first-stage PCR may be performed in the same blister. This is referred to herein as the "two zone method," wherein sample preparation and first-stage PCR are performed in one zone and second-stage PCR is performed in a second zone.

In a first step, a sample may be injected into blister 5010 via fill channel 5040c. In one embodiment, cells, viruses, and the like are lysed in blister 5010 using the wiping system described in detail elsewhere herein. Alternatively, cell lysis may be accomplished with an alternative lysis device such as, but not limited to, a sonication device or a bead beater or chemical lysis. Lysis may be aided by heating the sample to an elevated temperature (e.g., about 70-90° C.) with one or more heater elements of the heater assembly described in detail elsewhere herein. Following lysis, the sample may optionally be cooled with a thermoelectric cooler element (i.e., a Peltier element) to a reduced temperature (e.g., a temperature below ambient temperature such as, but not limited to, ~0-10° C.).

Magnetic beads may be injected into blister 5010 via fill channel 5040c in order to recover nucleic acids from the lysate. In one embodiment, the magnetic beads and the lysate may be mixed cold (e.g., at a temperature in a range of about 0-10° C.) after lysis. In another embodiment, a combination of cells to be lysed, lysis buffer, magnetic beads, and, optionally, lysis beads may be injected together into blister 5010 such that lysis and nucleic acid capture may occur at substantially the same time. Once the magnetic beads and the lysate have been thoroughly mixed for a sufficient time, the magnetic beads may be gathered in blister 5010 with a magnet and the spent lysate may be sent to blister 5005 (i.e., the liquid waste blister in this example) liquid waste via channel 5050a. Then wash buffer may be injected into blister 5010 via fill channel 5040c. Optionally, the wash buffer and the magnetic beads may be mixed cold (e.g., at a temperature in a range of about 0-10° C.). The magnetic beads are gathered again and the spent wash buffer may be flushed to blister 5005. The wash cycle may be repeated one or more times, if desired. After wash, nucleic acids may be eluted from the beads (optionally at an elevated temperature of, e.g., about 70-90° C.) by injecting an elution buffer (plus first-stage PCR primers) into blister 5010. The magnetic beads and any remaining lysis beads (if present) may be collected into the upstream half of blister 5010, and sent to waste blister 5005 via channel 5050a.

For first-stage PCR, the wiper system may be set and first-stage PCR master mix may be injected into channel 5040d and optionally held at an elevated temperature (e.g., about 57° C.) if a true hot-start may be desired. First-stage PCR master mix may be mixed with primers and template in blister 5010 and first-stage PCR may be performed as described above.

Following first-stage PCR, the protocol may proceed to second-stage PCR as described above for the "three zone method."

When fluorescent detection is desired, an optical array may be provided. An optical array may include a light source, illustratively a filtered LED light source, filtered white light, or illumination, and a camera. The camera illustratively has a plurality of photodetectors each corresponding to a second-stage well in array 5081 of pouch 5000. Alternatively, the camera may take images that contain all of the second-stage wells, and the image may be divided into separate fields corresponding to each of the second-stage wells. Depending on the configuration, the optical array may be stationary, or the optical array may be placed on movers attached to one or more motors and moved to obtain signals from each individual second-stage well. It is understood that other arrangements are possible.

Figure 6A:
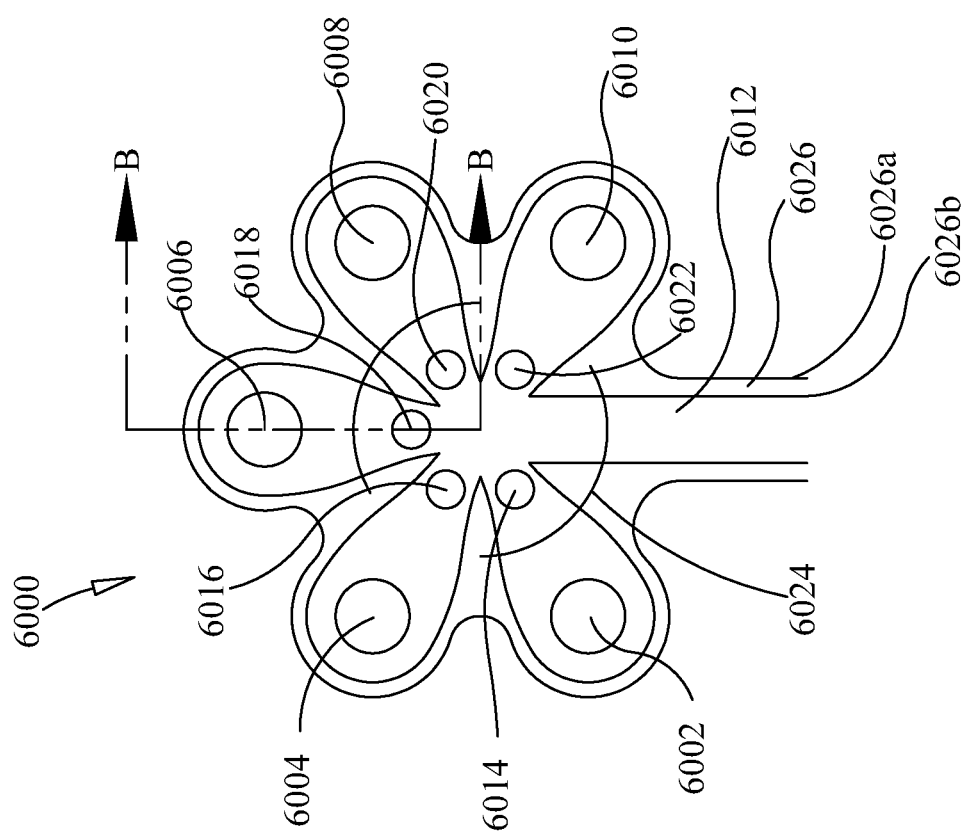
FIG. 6A shows an illustrative second-stage array.

Referring now to FIG. 6A, an array 6000 of wells that may be used for second-stage PCR is illustrated in greater detail. Array 6000 may be a standalone array or it may be included as a group of wells in a larger array, such as part of array 5081. Array 6000 includes individual wells 6002, 6004, 6006, 6008, and 6010. Each of wells 6002, 6004, 6006, 6008, and 6010 may be used for a second-stage PCR reaction. In the illustrated embodiment, the wells 6002, 6004, 6006, 6008, and 6010 are fluidly connected to a fill channel 6012; holes 6014, 6016, 6018, 6020, and 6022 are formed in the fill channel 6012 for filling each of the wells. In one embodiment, wells of a second-stage array (e.g., wells 6002, 6004, 6006, 6008, and 6010) may be under a partial vacuum to facilitate drawing fluid from the fill channel 6012 into the wells. In one embodiment, the wells 6002, 6004, 6006, 6008, and 6010 can be sealed off from the fill channel 6012 and from each other and leakage or mixing of fluid between wells, which may be referred to as "crosstalk," can be minimized or prevented by applying a seal (e.g., a heat seal) or pressure in or around the region illustrated at 6024. Thus, the single seal may be applied in the region indicated at 6024 to close off wells 6002, 6004, 6006, 6008, and 6010 from fill channel 6012 and from each other to prevent well-to-well cross-talk. The cross-sectional structure of the array 6000 and the flow path for filling the wells is illustrated below in FIGS. 6B and 6C. And while array 6000 is illustrated with five wells 6002, 6004, 6006, 6008, and 6010 associated with the fill channel 6012, one will appreciate that more or fewer reaction wells can be associated with a fill channel and that multiple fill channels can be fluidly connected to multiple clusters of wells. Multiple arrays 6000 may be used in combination to create larger arrays.

Referring now to FIGS. 6B and 6C, FIG. 6B is a cross-sectional view illustrated along the line B-B of FIG. 6A, and FIG. 6C is an alternative embodiment showing different embodiments of well filling systems. The portion of the array 6000 illustrated in cross section in FIGS. 6B and 6C is made of layers similar to those shown in FIG. 5C; it should be noted that the array 6000 may be included as part of the pouch 5000 shown in FIG. 5A instead of array 5081. The well 6006*b* shown in FIG. 6B may be defined by a first film layer 6030*b*, a second film layer 6032*b*, an adhesive layer 6034*b*, a card layer 6036*b* in which well 6006*b* may be defined, a second adhesive layer 6038*b*, and a third (outside) film layer 6040*b*. The well 6006*c* shown in FIG. 6C is quite similar and may be defined by a first film layer 6030*c*, a second film layer 6032*c*, an adhesive layer 6034*c*, a card layer 6036*c* in which a well 6006*c* may be formed, a second adhesive layer 6038*c*, and a third (outside) film layer 6040*c*. The key differences between 6B and 6C are in how the wells 6006*b* and 6006*c* are formed in the surrounding layers and in how the wells may be filled.

In FIG. 6B, the fill channel 6012*b* may be formed by leaving a gap between the first and second film layers 6030*b* and 6032*b* where liquid can flow. FIG. 6C shows a similar fill channel 6012*c* formed by leaving a gap between the first and second film layers 6030*c* and 6032*c*. The fill channels may be defined by weld lines 6026*b* or 6026*c* that seal the first and second film layers together around the array. An example of how these welds may be applied is shown in FIG. 6A at weld region 6026 that includes an outer weld 6026*a* and an inner weld 6026*b* defining the fill channel 6012 and the space around the wells. In FIG. 6B, the fill hole 6018*b* may be formed by making selective cutouts in the second film layer 6032*b* and in the first adhesive layer 6034*b*. In FIG. 6C, the fill hole 6018*c* may be formed by making a selective cutout in the second film layer 6032*c* that is adjacent to a corresponding cutout in the first adhesive layer 6034*c*.

In FIG. 6B, a well filling channel that flows around and over the well 6006*b* for filling the well may be formed by making a cutout 6042*b* in the card layer 6036*b* and a cutout 6044*b* in the second adhesive layer 6038*b*, although other ways of forming these channels are possible. The design of the well filling channel of FIG. 6B may, for instance, help to suppress cross-talk between wells because the flow path is convoluted. Likewise, because the fill channel 6012*b* and the fill hole 6018*b* are formed between two film layers 6030*b* and 6032*b*, the fill hole 6018*b* and access to the well 6006*b* can be sealed, illustratively with a heat seal device or by pressure, illustratively by a bladder that inflates in the region adjacent to 6024 of FIG. 6A or against all or part of the array 6000. In FIG. 6C, the well filling channel 6018*c* flows directly into the well 6006*c* and may be formed by making a cutout 6046*c* in the first adhesive layer 6034*c* that fluidly connects the fill hole 6018*c* to the well 6006*c*. It is expected that the filling design of FIG. 6C will also generally suppress cross-talk between wells. However, the design of FIG. 6C may be sealed, illustratively, with a heat seal device, which may provide better sealing than pressure alone.

In some embodiments, the wells of the second-stage array may be under at least a partial vacuum to facilitate filling of the wells with fluid for second stage PCR. Generally, this may mean that the pouch is stored under a partial vacuum from the time of manufacture until packaging surrounding the sample vessel is opened at the time of use. In one illustrative example, FIGS. 7A and 7B illustrate an embodiment of a second-stage array that may be used as an alternative to vacuum storage while still allowing reliable well filling in the second-stage array. As will be discussed in detail below, FIGS. 7A and 7B schematically illustrate an array that includes a vacuum way that may, illustratively, be formed in a liquid filling channel that allows a partial vacuum to be pulled on the array in situ.

FIGS. 7A and 7B illustrate another embodiment of a second-stage array 11000 that that may be filled without having the pouch manufactured and stored under partial vacuum. Second-stage array 11000 is similar to second-stage array 6000 illustrated in FIG. 6A. Second-stage array 11000, which is defined in part by weld line 11026, includes second-stage wells 11002, 11004, 11006, 11008, and 11010 that can each be provided with a unique second-stage primer pair and that can be filled with component for second-stage PCR (e.g., diluted product from first-stage PCR, polymerase, dNTPs, etc.) and be thermal cycled for second-stage analysis, as described in detail elsewhere herein. The second-stage wells are fillable from fill channel 11012, which is in fluid communication with fill holes 11014, 11016, 11028, 11020, and 11022 and fluidic vias 11052*a*-11052*e* that are associated with each second-stage well. Integrally formed in the fill channel and in fluid communication with each of the fill holes, vias, and second-stage wells is an illustrative vacuum way 11050. Vacuum way 11050 is in turn in fluid communication with port 11051 that may be placed on a portion of the pouch away from the array. In one embodiment, port 11051 may include a hole 11051*a* that provides fluid access to the vacuum way. Illustratively, hole 11051*a* may be formed in either layer 11030 or 11032. Vacuum way 11050 can illustratively be used to pull a partial vacuum on the second stage wells in situ (e.g., by a vacuum pump in the instrument during a pouch run) so that the pouch does not need to be manufactured or stored under vacuum. In one embodiment, vacuum channel 11050 may illustratively be connected to a remote vacuum hub on the pouch that can be connected to a vacuum source.

Referring now to FIG. 7B, a cross-section of the fill channel 11012 and the vacuum way 11050 is illustrated. In the illustrated embodiment, the fill channel 11012 is formed as an open space between two film layers 11030 and 11032 that are joined together (e.g., laser welded) on their edges at 11026. Illustratively, the vacuum way 11050 may be formed as a sub-channel in one of layers 11030 or 11032. In the illustrated embodiment, the vacuum way 11050 has an arch shape that is designed to hold channel 11012 open and connect the fill holes, vias, and second-stage wells to the vacuum source via vacuum way 11050 and port 11051. Without the vacuum channel 11050, channel 11012 may tend to collapse or "kiss" shut when a vacuum in pulled on the channel and prevent evacuation of the wells. In one embodiment, the vacuum channel 11050 may be formed as a recessed conduit in one of the layers with a heat forming fixture (e.g., an appropriately shaped hot 'debossing' wire). In other embodiments, the vacuum channel 11050 may be formed by laser etching, xurography, or the like. As illustrated in FIG. 7B, vacuum way 11050, which is an example of a heat formed channel, has an arch shape that supports the plastic and holds the channel open so that the vacuum can draw air out of the second-stage wells. While an arch shape is illustrated, it is understood that channels having other shapes may be used herein that are used to maintain the fill channel in an open position. Nonetheless, the vacuum way 11050 can be sealed by, for example, bonding layers 11030 and 11032 to one another by applying a heat seal over the vacuum way 11050, illustratively, near port 11051 and away from the array wells.

In one embodiment, a vacuum of at least 1-150 millibar (e.g., 2-10 millibar or, more preferably, 2-5 millibar) may be pulled on the second stage array (or portion of another reaction container configured for having a vacuum drawn thereon in situ) for 10-120 seconds in situ (e.g., in an instrument configured for drawing a vacuum on one or more portions of a reaction container and performing reactions un the reaction container, or immediately prior to inserting the reaction container into an instrument for running an analytical method). Following pulling a vacuum, the vacuum channel may be sealed (e.g., heat seated) and the vacuum may be released at port 11051, which leaves the wells of the array under a partial vacuum. Experiments on prototype arrays with vacuum channels similar to what is described above have shown that pulling a vacuum in situ can be as effective as manufacturing and storing the pouch under vacuum.

Some embodiments of the present disclosure can include an array assembly that comprises a plurality of wells arranged in an array, an integrally formed (e.g., in-molded) channel system in fluid communication with a plurality of wells, and an integrally formed (e.g., in-molded) vacuum port in fluid communication with the channel system. The channel system can also have an integrally formed fluid opening separate from the vacuum port. In some embodiments, a fluid reservoir or source with an openable seal (e.g., with a frangible seal, a peelable seal, or other seals as are known in the art) may be positioned adjacent to the array assembly. In some embodiments, a vacuum can be applied to the array assembly by drawing a vacuum at the vacuum port; the openable seal between the fluid source and the array assembly may typically be kept closed while evacuating the array assembly. By opening the seal separating the fluid source from the array assembly, a fluid sample can be drawn by the vacuum through the channel system and into the plurality of wells.

Figure 8A:
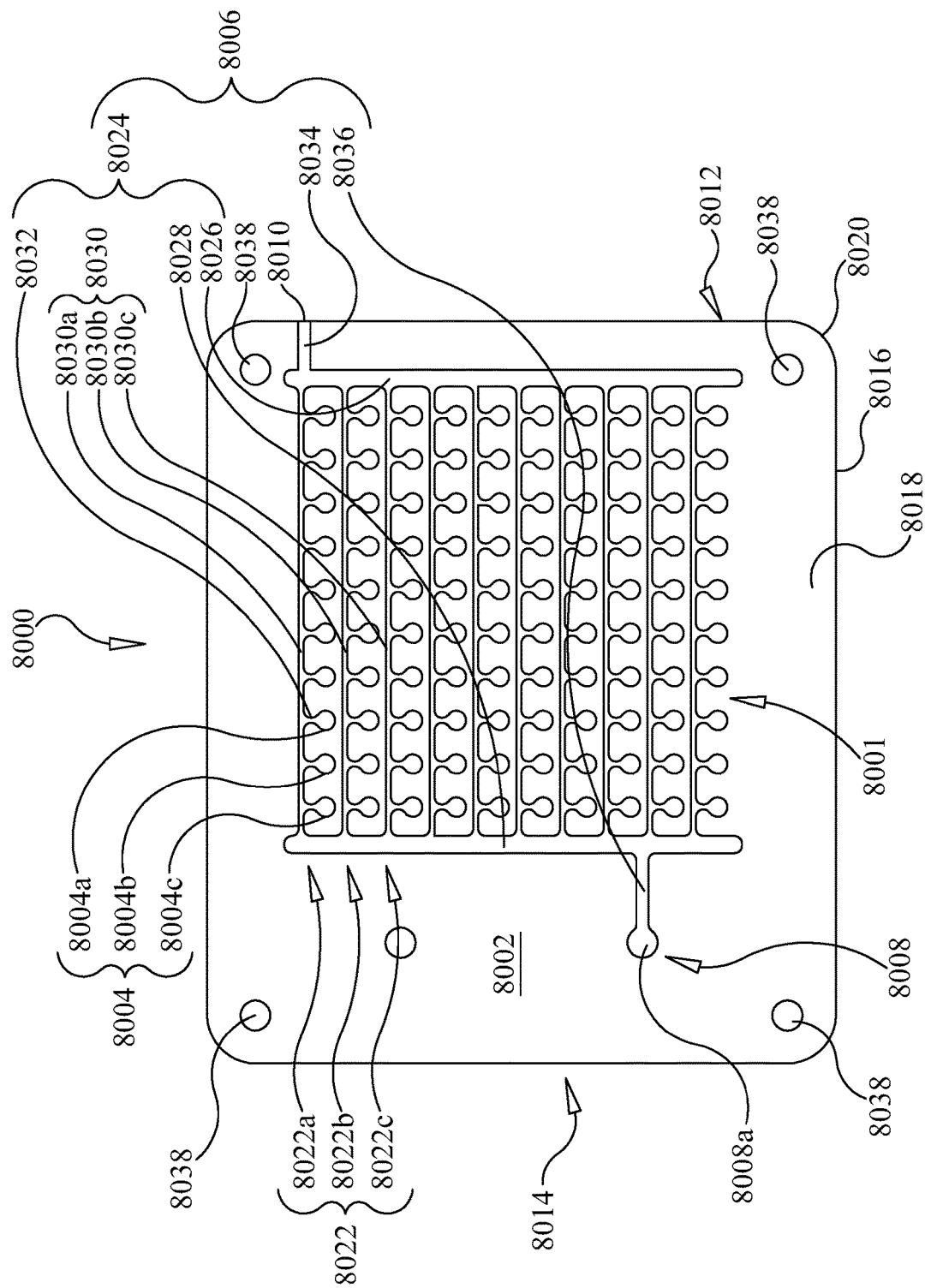
FIG. 8A is a perspective view of one illustrative embodiment of an array assembly comprising a card.

FIG. 8A depicts an illustrative array assembly 8000 according to an embodiment of the present disclosure that may be used as part of any pouch or card discussed herein or in other such embodiments. As depicted in FIG. 8A, array assembly 8000 comprises a card or card layer 8002 having a plurality of wells 8004 arranged in an array 8001. As illustrated, for example, in reference to FIGS. 8C and 8D, card 8002 may be disposed in a sealed reaction container between two or more film layers. Illustrative card 8002 comprises a first (lower) surface 8016, a second (upper) surface 8018 opposite first surface 8016, and a perimeter edge 8020 extending therebetween. Card 8002 can be any suitable size, including thickness, length, width, etc. For example, card 8002 may have a thickness of about 0.2-0.3 mm and the wells may be sized so that the card thickness and the well diameter yield wells of 0.20-0.5 µl, illustratively 0.3 µl. As depicted in FIG. 8A, illustrative card 8002 has a rectangular shape, with optionally rounded corners. In other embodiments, however, card 8002 can have any suitable shape. Wells 8004 may be arranged in rows, as shown in FIG. 8A, in circular or hexagonal arrangements, as in FIGS. 1 and 6A, or in other arrangements. It is understood that the term "array" includes any such arrangement of wells.

Wells 8004 can comprise, be formed of, or be defined by a hole or aperture extending through card 8002 (e.g., from first surface 8016 to second surface 8018). In alternative embodiments, the hole or opening can extend only part way through card 8002. Thus, in some embodiments, wells 8004 can comprise, be formed of, or be defined by a recess or indentation in card 8002 or second surface 8018 thereof. The recess or indentation forming wells 8004 can have any suitable depth within (or less than) the thickness of card 8002 (between first surface 8016 and second surface 8018). As depicted in FIG. 8A, wells 8004 has a round or cylindrical configuration. In alternative embodiments, however, wells 8004 can have other shapes or configurations, some of which are shown in FIGS. 12A-12D.

As discussed above, array 8001 can have any suitable configuration. As depicted in the illustrative example of FIG. 8A, array 8001 comprises a plurality of wells 8004 disposed in a plurality of rows 8022. Illustratively, wells 8004a, 8004b, and 8004c are in a first row 8022a of wells 8004. A second row 8022b of wells 8004 is adjacent to first row 8022a of wells 8004. A third row 8022c of wells 8004 is adjacent to second row 8022b, opposite first row 8022a. Additional rows 8022 of wells 8004 can be adjacent to, aligned (parallel) with, and/or disposed between or opposite first row 8022a, second row 8022b, and/or third row 8022c. Accordingly, illustrative rows 8022 of wells 8004 are arranged in a grid or grid-like configuration (e.g., with wells 8004 of each row 8022 aligned or substantially aligned with wells 8004 of another row 8022).

As depicted in FIG. 8A, array 8001 of wells 8004 comprises ten rows 8022 of ten wells 8004. In alternative embodiments, however, array 8001 can have any suitable number of rows 8022, such as, for example, greater than 100 rows, from 1 to 100 rows, 2 to 80 rows, 3 to 75 rows, 4 to 60 rows, 5 to 50 rows, 6 to 40 rows, 7 to 20 rows, 8 to 12 rows, or any suitable number of rows, or range of number of rows disposed therebetween. In some embodiments, array 8001 can have at least 1 row, 2 rows, 3 rows, 4 rows, 5 rows, 6 rows, 8 rows, 10 rows, 12 rows, 16 rows, 24 rows, 32 rows, 48 rows, 64 rows, or 96 rows.

In some embodiments, row(s) 8022 can have any suitable number of wells 8004, such as, for example, greater than 100 wells, from 1 to 100 wells, 2 to 80 wells, 3 to 75 wells, 4 to 60 wells, 5 to 50 wells, 6 to 40 wells, 7 to 20 wells, 8 to 12 wells, or any suitable number of wells, or range of number of wells disposed therebetween. In some embodiments, row(s) 8022 can have at least 1 well, 2 wells, 3 wells, 4 wells, 5 wells, 6 wells, 8 wells, 10 wells, 12 wells, 16 wells, 24 wells, 32 wells, 48 wells, 64 wells, or 96 wells. In at least one embodiment, array 8001 can have at least one row 8022 of a plurality of wells 8004, a plurality of rows 8022 of at least one well 8004, or a plurality of rows 8022 of a plurality of wells 8004.

Array assembly 8000 further comprises a channel system 8006 in fluid communication with the plurality of wells 8002, with a fluid entry opening 8010 in a first side 8012 of card 8002, and with a vacuum port 8008 in a second side 8014 of card 8002. Accordingly, as described above, fluid opening 8010 can be separate from vacuum port 8008. In the illustrated embodiment, vacuum port 8008 is disposed on an opposite side of wells 8004 from fluid opening 8010. It will be appreciated, however, that this orientation is illustrative only, and other configurations are possible. As depicted in FIGS. 8C-D, it is understood that array assembly 8000 may be incorporated into a pouch or science card, wherein fluid opening 8010 is in fluid communication with other reaction zones.

As depicted in FIG. 8A, vacuum port 8008 comprises a hole 8008*a* in card 8002. Hole 8008*a* extends through card 8002, from first surface 8016 to second surface 8018. Similar to wells 8004, in an alternative embodiment, hole 8008*a* can extend only part way through card 8002. Thus, in some embodiments, hole 8008*a* can comprise, be formed of, or be defined by a recess or indentation in card 8002 or second surface 8018 thereof. The recess or indentation forming hole 8008*a* can have any suitable depth within (or less than) the thickness of card 8002 (between first surface 8016 and second surface 8018). As depicted in FIG. 8A, hole 8008*a* has a round or cylindrical configuration. However, hole 8008*a* can alternatively have another shape or configuration. In an alternative embodiment, vacuum port 8008 can comprise an end or other portion of channel system 8006.

As depicted in FIG. 8A, channel system 8006 comprises a manifold channel assembly 8024 in fluid communication with fluid entry channel 8034. Manifold channel assembly 8024 comprises a first main channel 8026 that is fluidly connected to fluid entry channel 8034, a second main channel 8028 that is fluidly connected to vacuum port 8008, and a plurality of branch channels 8030 extending between first main channel 8026 and second main channel 8028. Each branch channel 8030 extends alongside one or more rows 8022 of wells 8004. Illustratively, a first branch channel 8030*a* extends alongside first row 8022*a*, a second branch channel 8030*b* extends alongside second row 8022*b*, a third branch channel 8030*c* extends alongside third row 8022*c*, and so forth. A plurality of connection channels 8032 extend from each branch channel 8030 to respective wells 8004 in each row 8022. Illustratively, each connection channel 8032 extends from one well 8004 in a particular row 8022 to a branch channel 8030 extending alongside that particular row 8022. Illustratively, each of the wells 8004 in a particular row 8022 is in fluid communication with the branch channel 8030 extending alongside that particular row 8022 by means of a respective connection channel 8032.

Figure 8B:
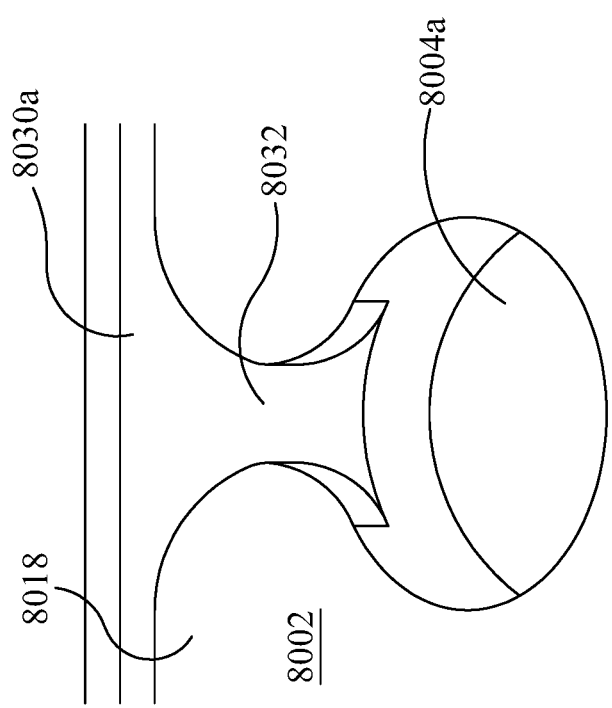
FIG. 8B is a detailed view of a portion of the array assembly of FIG. 8A.
Figure 8C:
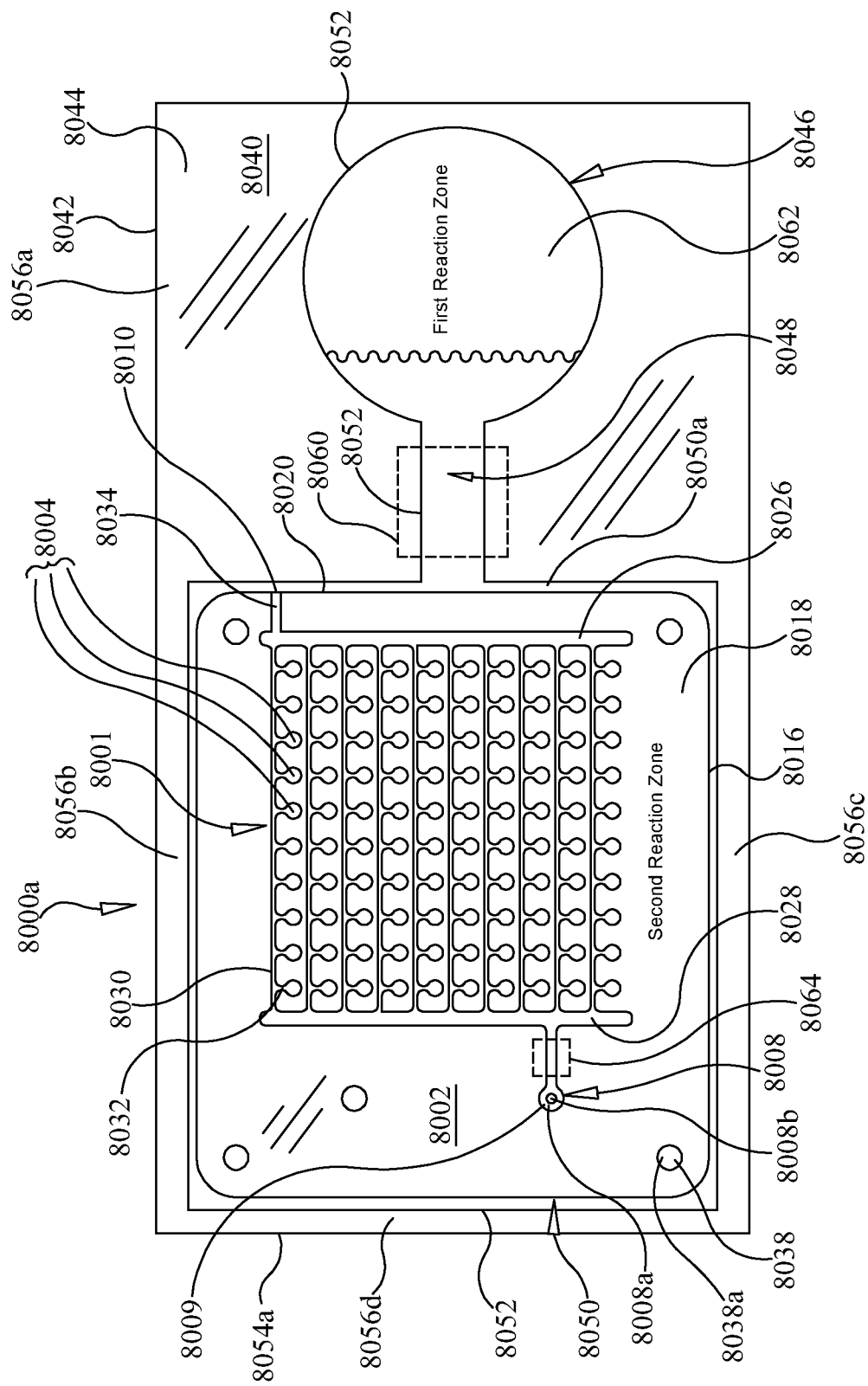
FIG. 8C is a top plan view of another illustrative embodiment of an array assembly comprising a card layer in a pouch.
Figure 8D:
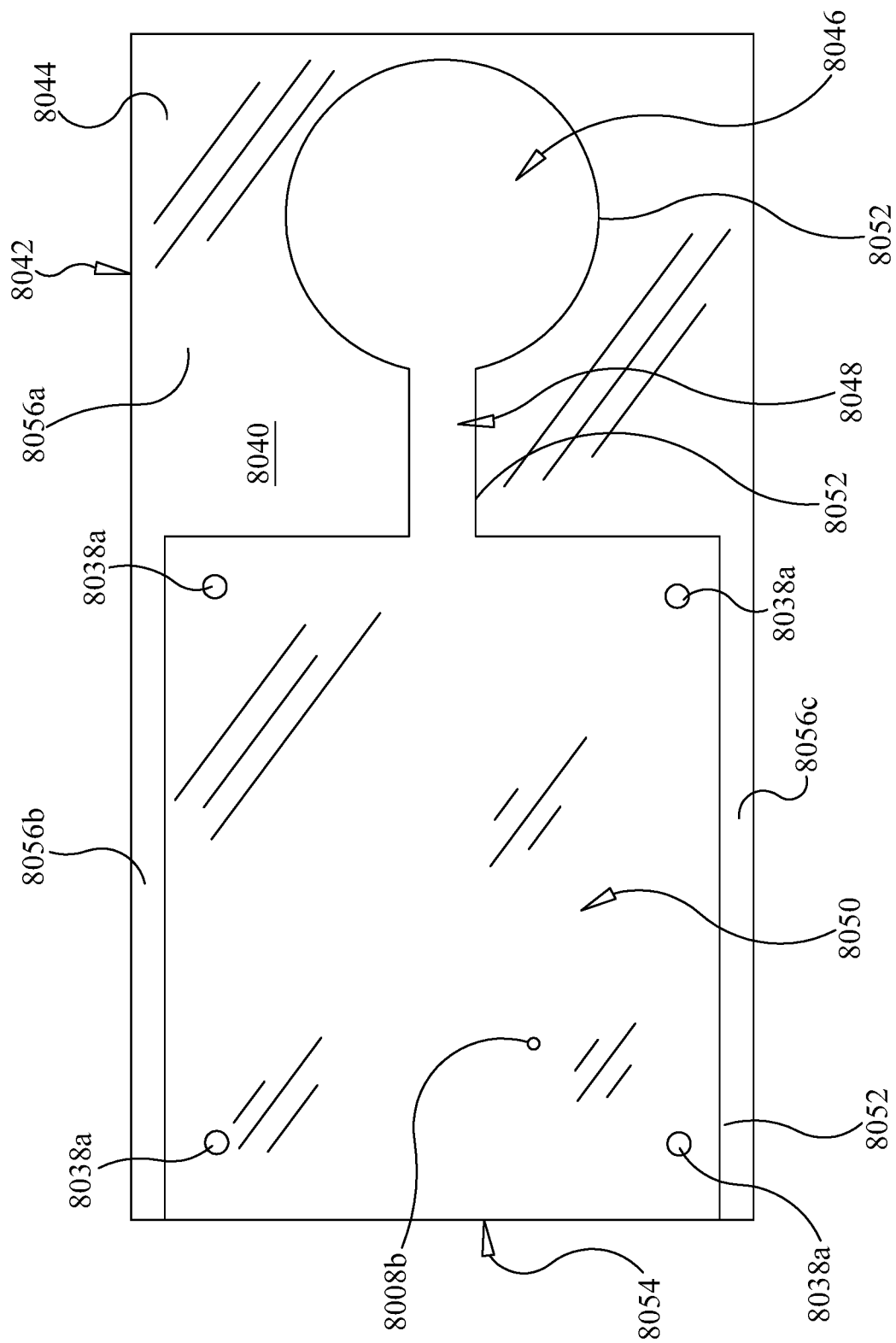
FIG. 8D is a top plan view of a pouch.

FIG. 8B is a detailed view of card 8002 at well 8004*a*, connection channel 8032, and branch channel 8030*a*. As illustrated in FIG. 8B, connection channel 8032 and branch channel 8030*a* (and, indeed, all of channel system 8006) can comprise, be formed of, or be defined by a recess or indentation in card 8002 or second surface 8018 thereof. The recess or indentation forming channel system 8006 or one or more components thereof can have any suitable depth within (or less than) the thickness of card 8002 (between first surface 8016 and second surface 8018). As depicted in FIG. 8A, channel system 8006 has a squared configuration. In alternative embodiments, however, channel system 8006 can have other shapes or configurations. In some embodiments, certain components of channel system 8006 can have a depth greater than or less than other components of channel system 8006. As depicted in FIG. 8A, however, all components of channel system 8006 have the same depth and wells 8004 have a greater depth.

Figure 12A:
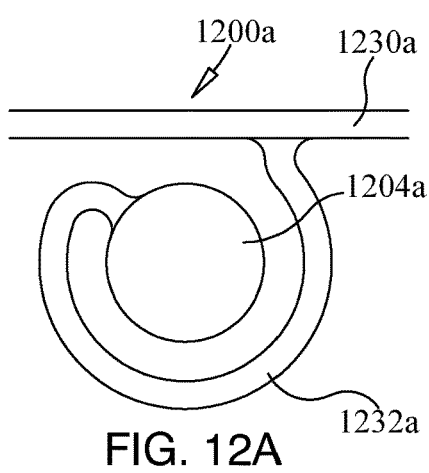
FIGS. 12A-12D show various array well and channel configurations.
Figure 12B:
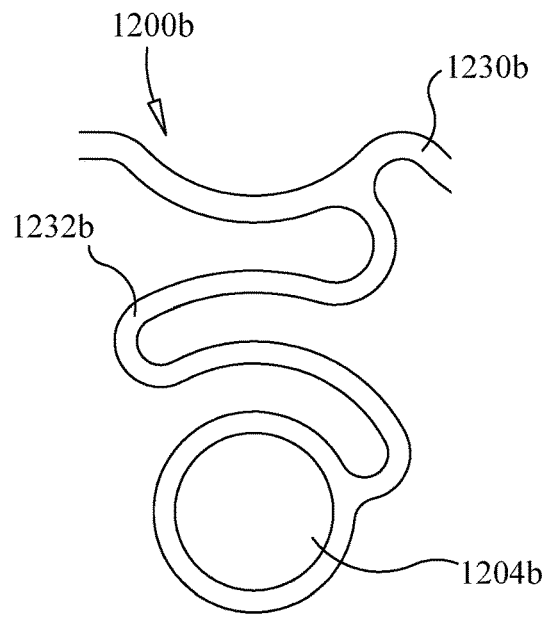
Figure 12C:
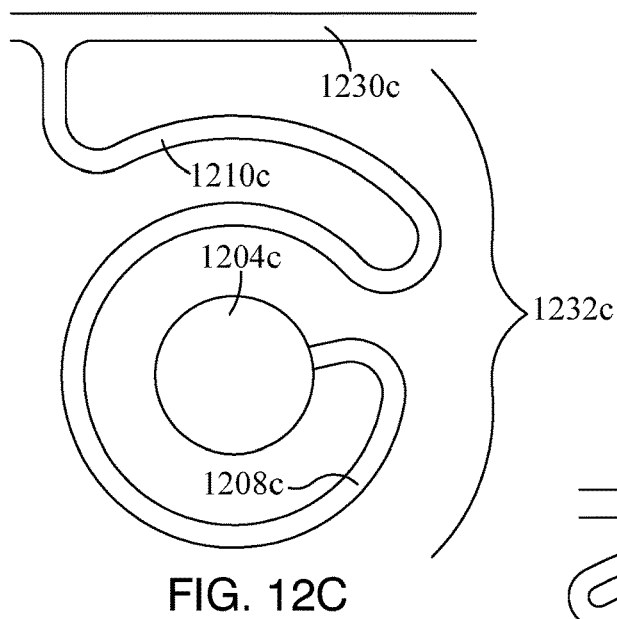
Figure 12D:
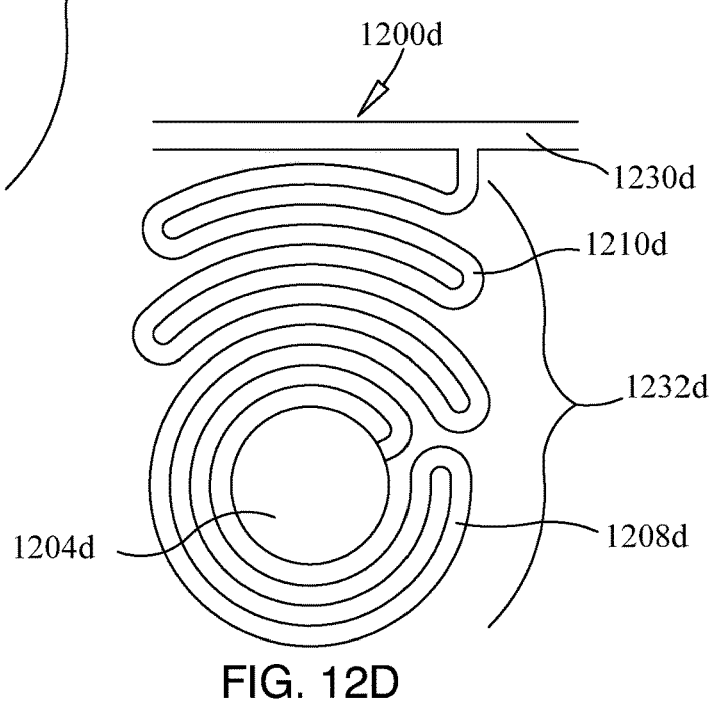

Referring now to FIGS. 12A-12D, examples of various well filling paths for wells in an array are shown. FIGS. 8A-8C showed one example of a "convoluted" array well filling path that includes wells 8004, array flow channels 8030, and straight well fill channels 8032 as the well filling path. FIGS. 12A-12D illustrate examples of well filling paths that are less direct than well fill channels 8032. Each example in FIGS. 12A-12D includes a well 1200*a*-1200*d* and an array flow channel 1230*a*-1230*d*. FIG. 12A illustrates an embodiment of a spiral channel 1232*a* leading into well 1204*a*. FIG. 12B illustrates a switchback channel 1232*b* leading into well 1204*b*. FIG. 12C illustrates a channel 1232*c* that includes a spiral portion 1208*c* and a switch back portion 1210*c* leading into well 1204*c*. FIG. 12D illustrates a channel 1232*d* with a spiral switchback portion 1208*d* and a parallel switchback portion 1210*d* leading into well 1204*d*. When placed in a pouch, the wells and the channels illustrated in FIGS. 8A-8C and 12A-12D would be sealed with at least one layer on the top and bottom. Thus, the only flow paths into the wells is through the flow channels and the well channels. While some paths are more "convoluted" than others, the combination of the flow channels and the well channels generally isolates the wells from one another and minimizes mixing (i.e., cross-talk) between wells as the wells are filled. The foregoing examples are merely illustrative examples of convoluted well filling paths and one will appreciate that other well filling paths may be used.

Referring again to FIG. 8A, illustrative channel system 8006 also includes a fluid access channel 8034 extending from fluid opening 8010 to first main channel 8026. As depicted in FIG. 8A, fluid opening 8010 can be disposed in perimeter edge 8020 and/or second upper surface 8018 of card 8002. Fluid access channel 8034 can be configured to introduce or permit a fluid into channel system 8006 or manifold channel assembly 8024 thereof. For instance, as described further herein, card 8002 can be sealed in a pouch or between two layers of film (see, e.g., FIGS. 8C and 8D). Accordingly, in some embodiments, access channel 8034 can be used to fluidly transfer a liquid sample from the pouch into array 8001 or wells 8004 thereof. In some embodiments, fluid access channel 8034 can be in fluid communication with a fluid source (see, e.g., FIGS. 8C and 8D). In at least one embodiment, the fluid source with which access channel 8034 is in fluid communication with a blister in a film pouch (see e.g., blister 566 of pouch 510 of FIG. 1). An optional fluid channel (see e.g., channel 565 of FIG. 1) can extend between access channel 8034 and the fluid source. Other suitable fluid sources as known in the art are also contemplated herein.

Channel system 8006 also includes a vacuum port channel 8036 extending from vacuum port 8008 to second main channel 8028. Accordingly, each well 8004 is in fluid communication with a connection channel 8032, which is in fluid communication with a branch channel 8030, which is in fluid communication with first main channel 8026 and second main channel 8028. First main channel 8026 is in fluid communication with fluid access channel 8034, which is in fluid communication with fluid opening 8010. Accordingly, each well 8004 is in fluid communication with fluid opening 8010 (by means of channel system 8006) from at least two directions (either (i) directly through first main channel 8026, its own branch channel 8030, and its own connection channel 8032, or (ii) indirectly through first main channel 8026, a connection channel 8032 from a different row, second main channel 8028, its own branch channel 8030, and its own connection channel 8032). This parallel arrangement with multiple connection channels extending between two or more main channels allows for pulling a vacuum on all wells and for filling all wells even if one of the channels becomes obstructed. Second main channel 8028 is in fluid communication with port channel 8036, which is in fluid communication with vacuum port 8008. Accordingly, each well 8004 is in fluid communication with vacuum port 8008 (by means of channel system 8006). It is understood that this arrangement is illustrative, and many alternative arrangements are possible.

Card 8002 can also have one or more optional alignment indicators 8038. As shown in FIG. 8A, optional alignment indicator(s) 8038 comprise an opening or a hole extending into or through one or more of surfaces of card layer 8002. Other optional alignment indicator(s) 8038 include a recess (or indentation) or a marking (e.g., printed pattern or image) disposed on one or more surfaces of card layer 8002.

In some embodiments, one or more of the features or components of card 8002 (e.g., wells 8004, parts of channel system 8006, port hole 8008a, alignment indicators 8038, etc.) can be formed during manufacture, illustratively during injection molding, of card 8002. Alternatively, one or more of the features or components of card 8002 can be formed by removing material of card 8002.

FIG. 8C depicts an illustrative embodiment of an array assembly 8000a. Array assembly 8000a comprises card (or card layer) 8002 disposed in a pouch 8040. Pouch 8040 can comprise or be formed of a first layer and a second layer. Illustrative card layer 8002 is disposed (e.g., sandwiched) between first film layer 8042 and second film layer 8044. In some embodiments, film layers 8042 and 8044 can be bonded to the top and bottom surfaces 8016 and 8018 of card layer 8002. Film layers 8042 and 8044 can also be selectively bonded to each other to create, for example, fluid channels and blisters between the film layers. Accordingly, some embodiments of the present disclosure relate to an array assembly 8000a comprising a card layer 8002 having the plurality of wells 8004 formed therein, the first film layer 8042 bonded to a first side or surface 8016 of card layer 8002, and/or a second film layer 8044 bonded to a second side or surface 8018 of card layer 8002. While film layers are used in this and other embodiments, it is understood that other materials may be used consistent with the application of array assembly 8000a.

As depicted in FIG. 8D, pouch 8040 can be pre-formed (e.g., prior to disposing card 8002 therein in some embodiments). Illustratively, (portions of) first film layer 8042 and second film layer 8044 can be bonded together, such as by thermoforming (e.g., laser welding or heat welding), by hot rolling (e.g., by partially bonding the first and second film layers 8042 and 8044 together by rolling the layers between hot rollers during manufacture), or by an adhesive (e.g., temperature sensitive adhesive, pressure sensitive adhesive, etc.). For instance, pouch 8040 includes a first bonded portion 8056a, a second bonded portion 8056b, a third bonded portion 8056c. Bonded portions 8056a, 8056b, and 8056c can at least partially bound or form a fluid reservoir (or blister) 8046, a fluid channel 8048 in fluid communication with blister 8046, and a pocket 8050 in fluid communication with fluid channel 8048. In some embodiments, while bonded portions 8056a, 8056b, and 8056c of pouch 8040, or first film layer 8042 and second film layer 8044 thereof, can be (permanently) bonded together (e.g. such as by the heat welding or pressure sensitive adhesive), blister 8046, fluid channel 8048, and pocket 8050 can be left unbonded, or openably (i.e., reversibly) bonded together. In some embodiments, the unbonded portions can be defined by one or more bond lines or weld lines 8052.

Illustratively, second film layer 8044 can be laid on top of first film layer 8042 to form a stack or layup. One or more portions of the overlaid film layers or stack can then be bonded together at bonded portions 8056a, 8056b, and 8056c, such as by thermoforming (e.g., heat welding) or by an adhesive (e.g., temperature sensitive adhesive, pressure sensitive adhesive, etc.). For example, one or more heated pressure plates or other selective bonding member bearing the pattern of bonded portions 8056a, 8056b, and 8056c can be used to form pouch 8040 from stack film layers 8042 and 8044 by applying heat and a force (e.g., pressure) to one or more sides of the layup.

Illustratively, as discussed above with reference to pouch 510, film layers 8042 and 8044 may be formed of plastic or other material that can be softened and/or (partially) melted such that the layers or surfaces thereof become bonded (e.g., thermoformed or heat-welded) together. For example, first and second film layers 8042 and 8044 can comprise or be formed of one or more materials with similar melting temperature(s) (Tm), glass transition temperature(s) (Tg), etc. Illustratively, first and second film layers 8042 and 8044 can comprise or be formed of one or more polymeric (e.g., plastic) or other materials, including combinations or blends thereof. Accordingly, a layup or stack of first film layer 8042 and second film layer 8044 can heated to at least the Tm or Tg of one or more of the materials (e.g., the material having the highest Tm or Tg), such that the layers or surfaces thereof become bonded (e.g., heat-welded) together (e.g., with application of a force (e.g., pressure) to the heated or melted layup.

In one or more alternative embodiments, an adhesive layer bearing the pattern of bonded portions 8056a, 8056b, and 8056c can be disposed between film layers 8042 and 8044 in the stack or layup. Illustratively, the adhesive layer can be or comprise a pressure sensitive adhesive (PSA). One or more pressure plates or other selective bonding member bearing the pattern of bonded portions 8056a, 8056b, and 8056c can be used to form pouch 8040 from stack film layers 8042 and 8044 by applying a force (e.g., pressure) to one or more sides of the layup. Alternatively, a temperature sensitive adhesive or other adhesive as known in the art can be used to form pouch 8040.

As further depicted in FIG. 8D, pocket 8050 can have an unbonded, open end or opening 8054 (e.g., between bond lines 8052 of bonded portions 8056b and 8056c, respectively) and one or more optional alignment indicators 8038a. Optional alignment indicator(s) 8038a can comprise an opening or hole through one or more of film layers 8042 and 8044. Alternatively, optional alignment indicator(s) 8038a can comprise a marking (e.g., printed pattern or image) disposed on one or more of film layers 8042 and 8044. Pouch 8040, or one or more of film layers 8042 and 8044 thereof, can include a piercing 8008b, in some embodiments.

Returning now to FIG. 8C, and with the continued reference to FIG. 8D, card layer 8002 can be inserted through opening 8054 into pouch 8050. Optional alignment indicator(s) 8038 of card layer 8002 can be aligned with optional alignment indicator(s) 8038a of first film layer 8042 and/or second film layer 8044, thereby indicating a proper alignment and/or position of card layer 8002 within pocket 8050.

Film layers 8042 and 8044 can be bound to inserted card layer 8002, such as by thermoforming or heat welding. Illustratively, one or more heated pressure plates or other bonding members can be used to bond film layers 8042 and 8044 to card layer 8002. The heated pressure plate(s) can have a substantially flat and/or uniform bonding surface in some embodiments. Alternatively, the heated pressure plate(s) can have a bonding surface bearing the pattern of card layer 8002 or components thereof.

It will also be appreciated that one or more adhesive layers bearing the pattern of card layer 8002 or components thereof (see FIG. 8A), can (also or alternatively) be disposed on one or more of surfaces 8016 and 8018, or corresponding surfaces of film layers 8042 and 8044. As illustrated in FIG. 5C, for example, a card layer (5094) can be bonded to a lower film layer (5098) by means of a first adhesive layer (5096), and to an upper film layer (5090) by means of a second adhesive layer (5092). Similarly, returning to FIG. 8C, first (lower) surface 8016 of card layer 8002 can be bonded to first film layer 8042 by means of a first adhesive layer (not shown). Likewise, second (upper) surface 8018 of card layer 8002 can be bonded to second film layer 8044 by means of a second adhesive layer (not shown). The first and/or second adhesive layers can be or comprise one or more pressure sensitive adhesives, temperature sensitive adhesives, or other adhesives, as known in the art and/or described herein.

A fourth bonded portion 8056d can then be formed in a manner similar to those described above, thereby sealing opening 8054 in a closed configuration, indicated at closed end 8054a. Thus, card layer 8002 can be (or become) bonded to pouch 8040 or film layers 8042 and 8044 thereof, and sealed within pocket 8050. In some embodiments, an unbonded pocket portion 8050a can be disposed at one or more sides of card layer 8002 within sealed pouch 8040. As depicted in FIG. 8C, for instance, unbonded pocket portion 8050a surrounds card layer 8002 inside sealed pouch 8040. Unbonded pocket portion 8050a can be defined by bond lines (e.g., weld lines) 8052 of bonded portions 8056a, 8056b, 8056c, and 8056d. Similarly, a fluid channel 8048 and reservoir (or blister) 8046 can be defined by bond lines 8052 of bonded portions 8056a.

In an alternative embodiment, array assembly 8000a can be formed with card layer 8002 disposed between unbonded sheets 8042 and 8044. Illustratively, a layup or stack of card layer 8002 disposed between first film layer 8042 and second film layer 8044 can be bonded as described above and/or with the pattern of pouch 8040 or bond lines 8052 thereof. For example, first and second film layers 8042 and 8044 and card layer 8002 can comprise or be formed of one or more (respective) materials with similar melting temperature(s) (Tm), glass transition temperature(s) (Tg), etc. Illustratively, first and second film layers 8042 and 8044 and card layer 8002 can comprise or be formed of one or more polymeric (e.g., plastic) or other materials, including combinations or blends thereof. In a preferred embodiment, first and second film layers 8042 and 8044 and card layer 8002 can comprise or be formed of polypropylene or a blend thereof. One will appreciate, however, that the layers can also be formed of other materials as known in the art.

The layup or stack of card layer 8002 disposed between first film layer 8042 and second film layer 8044 can heated to at least the Tm or Tg of one or more of the materials (e.g., the material having the highest Tm or Tg). A force (e.g., pressure) can also be applied to the layup, such that the layers or surfaces thereof become bonded (e.g., heat-welded) together. Alternatively, as described previously, one or more adhesive layers (e.g., bearing the pattern of card layer 8002 and/or bond lines 8052 of pouch 8040) can be disposed between card layer 8002 and one or more of first film layer 8042 and second film layer 8044, such that card layer 8002 becomes bonded to first film layer 8042 and/or second film layer 8044 by means of the adhesive layer(s).

As further illustrated in FIG. 8C, a fluid or liquid (sample) 8062 can be disposed in fluid reservoir (or blister) 8046. In the illustrated embodiment, the fluid 8062 can disposed (e.g., injected) into blister 8046 prior to insertion of card layer 8002 into pocket 8050. In other embodiments, such as those depicted in the corresponding drawings (see e.g., FIGS. 1 and 3), one or more additional fluid channels can be connected to and/or in fluid communication with a fluid reservoir (or blister). Accordingly, it will be appreciated that one or more additional fluid channels 8048 can extend from blister 8046, such that fluid 8062 can be introduced into blister 8046 after the formation of pouch 8040.

An openable seal can also be formed pouch 8040, such as in area 8060 of fluid channel 8048. As described previously, the openable seal can be or comprise a frangible or an openable seal (e.g., a peelable seal) formed by the electrostatic, tactile, or other attraction between film layers 8042 and 8044, rather than by bonding through thermoforming or adhesive. The openable seal can be configured to retain fluid 8062 within blister 8046 (e.g., such that fluid 8062 does not become inadvertently and/or prematurely disposed in pocket 8050).

Array assembly 8000a, or pouch 8040 thereof, can include at least one opening or piercing 8008b. Illustratively, piercing(s) 8008b can be formed in one or more of film layers 8042 and 8044 during manufacture of pouch 8040 or film layers 8042 and 8044 thereof. Alternatively, piercing(s) 8008b can be formed (in array assembly 8000a) during an illustrative analytical method. For instance, piercing(s) 8008b can be formed by a piercing element of analytical device (not shown) prior to a vacuum being applied at vacuum port 8008. Illustratively, piercing 8008b can be substantially aligned with hole 8008a of card layer 8002. In some embodiments, piercing 8008b and hole 8008a can form vacuum port 8008. In other words, vacuum port 8008 can comprise piercing 8008b and hole 8008a in some embodiments.

With reference to FIGS. 8A and 8B, by (openably) sealing channel system 8006 (e.g., at or near fluid opening 8010, such as at area 8060 in the adjacent fluid channel 8048, illustratively with a pressure seal or an openable seal (e.g., a frangible seal or a peelable seal) between the film layers 8042 and 8044 that form the fluid channel 8048), array assembly 8000, 8000a can be evacuated by applying a vacuum at vacuum port 8008 by means of a vacuum device—e.g., a piston pump (not shown). The seal at area 8060 allows the applied vacuum to evacuate port channel 8036, second main channel 8028, each branch channel 8030, first main channel 8026, fluid access channel 8034, each connection channel 8032, and each well 8004 of array 8001. In this context, channel system 8006 comprises or constitutes a vacuum channel. Illustratively, since vacuum is applied to the channel system prior to filling array assembly 8000, 8000a (e.g., with fluid sample 8062), the fluid sample (or first-stage amplicon in a two-step PCR system) is not introduced into the vacuum device, thereby minimizing or preventing contamination from connection with the vacuum device.

With array assembly 8000 evacuated and the applied vacuum maintained (e.g., such as by sealing off vacuum port 8008 at area 8064 of port channel 8036, illustratively by pressure and/or heat sealing), the seal at area 8060 can be opened, drawing fluid into array assembly 8000 (i.e., through fluid opening 8010, through first main channel 8026, through branch channels 8030, through connection channels 8032, and into array 8001 and wells 8004 thereof). By sealing port channel 8036 at area 8064, fluid is also drawn into second main channel 8028 and a portion of port channel 8036 (up to the seal). In this context, channel system 8006 comprises or constitutes an array fill channel. Accordingly, channel system 8006 comprises or constitutes an array fill channel (or channel assembly), as well as a vacuum channel (or channel assembly).

In the illustrated embodiment, each well 8004 can be isolated from all other wells 8004 by sealing branch channels 8030 between connection channels 8032. In at least one embodiment, a plurality of seals can extend across one or more (e.g., all) of the branch channels 8030 between one or more (e.g., all) of the connection channels 8032. Because each of the wells 8004 in a particular row 8022 communicates with an adjacent branch channel 8030 through a particular connection channel 8032, sealing across branch channels 8030 (e.g., perpendicular to the length of branch channels 8030 and rows 8022 of wells 8004) between connection channels 8032 substantially reduces or eliminates cross-talk between wells 8004.

By using (a manifold-type) channel system 8006 as both a vacuum channel and an array fill channel, card 8002 can be kept relatively small. It will be appreciated, however, that in some embodiments, array assembly 8000 can comprise a vacuum channel and a separate array fill channel. For instance, in an alternative embodiment, array assembly 8000 can comprise a dual manifold configuration, in which branch channels 8030 are not in fluid communication with both first main channel 8026 and second main channel 8028. Instead, a first set of branched (fill) channels 8030 can extend from first main channel 8026 and a second set of branched (vacuum) channels 8030 can extend from second main channel 8028. Respective connection channels 8032 can extend from each branch channel 8030 to respective wells 8004. A first connection channel 8032 can fluidically connect a particular well 8004 to an adjacent branched vacuum channel 8030 on a first side of the well 8004, well a second connection channel 8032 can fluidically connect the particular well 8004 to an adjacent branched fill channel 8030 on a second side of the well 8004.

As described above, vacuum port 8008 need not be disposed on an opposite side of wells 8004 from fluid opening 8010. For instance, vacuum port 8008 can be disposed on the same or adjacent side of wells 8004 as fluid opening 8010. Illustratively, vacuum port 8008 and fluid opening 8010 can be disposed on opposite ends of the same or adjacent side of wells 8004 as. Vacuum port 8008 can even be disposed adjacent to fluid opening 8010. For instance, in an alternative embodiment, channel system 8006, or manifold channel assembly 8024 thereof, can have only one main channel 8026. Illustratively, port channel 8036 can extend from main channel 8026, such that vacuum port 8008 or hole 8008a thereof can be in fluid communication with main channel 8026. In such a configuration, a fluid channel in fluid communication with access channel 8034 can still be openably sealed (e.g., adjacent to fluid opening 8010), and a vacuum cans still be applied through vacuum port 8008.

Figure 9A:
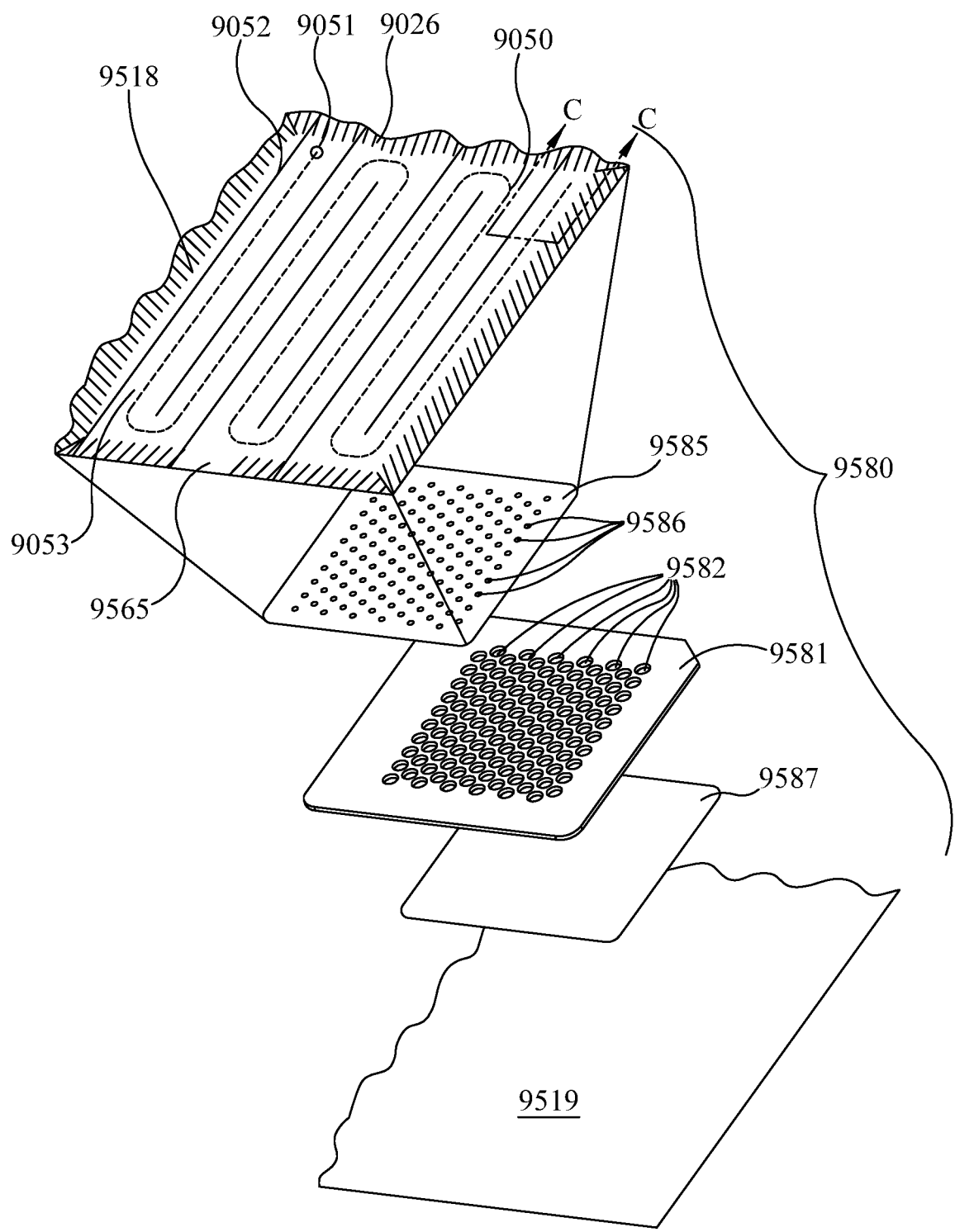
FIG. 9A is an exploded perspective view of an embodiment of a second-stage high density array having a vacuum channel.
Figure 9B:
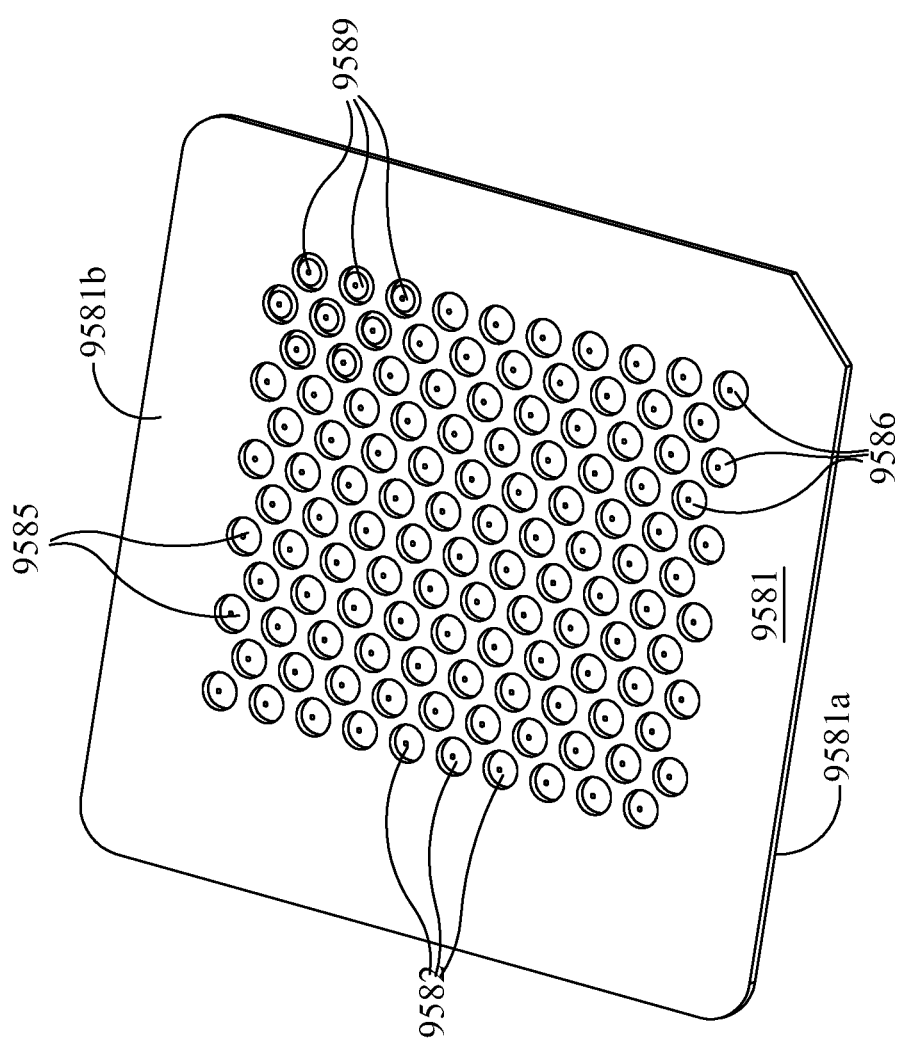
FIG. 9B is a bottom view of the second-stage high density array of FIG. 9A, shown during construction of the second-stage high density array.

FIGS. 9A and 9B show an illustrative embodiment of second-stage 9580 using a barrier layer. Sandwiched between first layer 9518 and second layer 9519 of pouch 9510 is high density array 9581, with wells 9582. As best seen in FIG. 9B, pierced layer 9585, with piercings 9586, is provided on one side of high density array 9581 to act as the physical barrier to minimize cross-talk between wells 9582 upon filling of array 9581, and a second layer 9587 is provided on the opposite side of high density array 9581 to form the bottom of wells 9582. In the illustrated embodiment, second-stage array 9580 is fabricated with pierced layer 9585 bonded to first layer 9518. In layer 9518, features are formed by, for example, bonding selected areas and impressing features into film layer 9518 to form a fluid flow channel 9053 and a concurrent vacuum channel 9050 to allow the pulling of a vacuum on the array in situ (i.e., at point of use) as an alternative to manufacturing and storing the array under vacuum. Illustratively, layer 9518 includes a fluid fill channel 9053 formed by bonding (e.g., by laser welding) layer 9518 to layer 9585. Fluid fill channel 9053, which is defined by laser weld lines 9052, is formed so as to be in fluid communication with each of the pierced holes 9586 in the layer 9585. Vacuum way 9050 is concurrent with and formed in fluid fill channel 9053 and is also in fluid communication with each of the pierced holes 9586 in the layer 9585. In one embodiment, vacuum way 9050 may be heat formed by shaping the film of film layer 9518 with a hot wire or the like to impress a channel into the film. Illustratively, pierced layer 9585 and first layer 9518 are bonded (e.g., welded) to one another around their edges at 9026. Pierced layer 9585 is bonded to high density array layer 9581, e.g., by and adhesive layer and/or heat sealing, and first layer 9518 is bonded (e.g., laser welded) to pierced layer 9585 at several weld lines 9052 parallel to and between columns of pierced layer holes 9586 to define the fill channel 9053. Fluid fill channel 9053, pierced layer 9585 and openings 9586, and array wells 9582 may be in fluid communication with an upstream fluid well via fluid channel opening 9565.

Figure 9C:
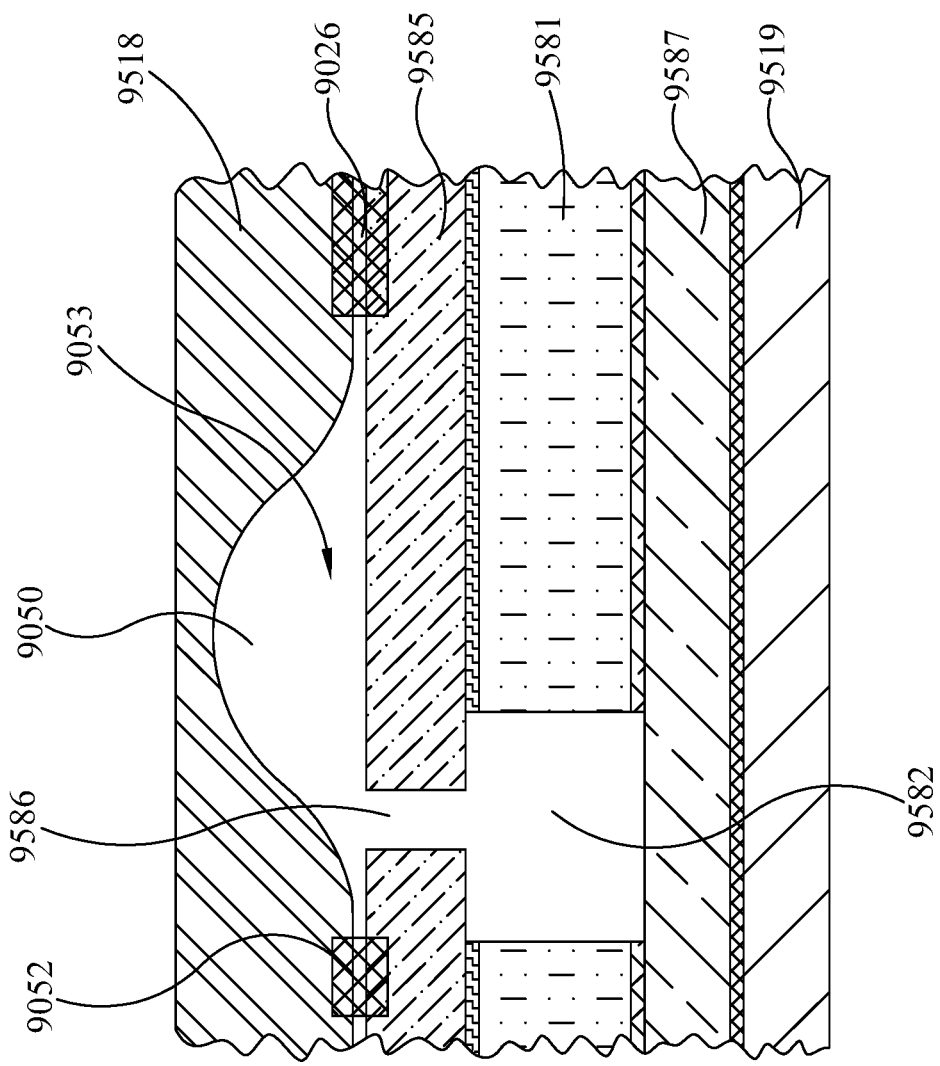
FIG. 9C is a cross-sectional view of a portion of FIG. 9A along the line C-C.

FIG. 9C illustrates a cross section along the line C-C of the layers of the array 9580. While FIG. 9A is shown in exploded view, FIG. 9C illustrates the relationship of the pouch film and array layers, the vacuum way 9050, and the fluid flow channel 9053. The "stack" of the second-stage amplification zone 9580 includes a first pouch film layer 9518 (i.e., a first outer layer of the pouch), a pierced layer 9585, an array 9581, a second layer 9587 (i.e., the array backing layer), and a second pouch film layer 9519 (i.e., a second outer pouch film layer). The cross-section of FIG. 9C illustrates one piercing 9586 and one well 9582 and how they relate to the vacuum way 9050, the fluid flow channel 9053, and the welds 9052 and 9026. While one piercing 9586 and one well 9582 are shown for ease and clarity, one can see from FIGS. 9A and 9C that the vacuum way 9050 and the fluid flow channel 9053 are fluidly connected to all of the piercings 9586 and wells 9582 of the second-stage amplification zone 9580.

In the illustrated embodiment, the fluid flow channel 9053 is formed as an open space between first layer 9518 and pierced layer 9585 that are joined together (e.g., laser welded) at welds 9052 and 9026 that define the fluid flow channel 9053. Illustratively, the vacuum way 9050 may be formed as a sub-channel in layer 9518. In the illustrated embodiment, the vacuum way 9050 has an arch shape that is designed to hold channel 9053 open and connect the channel 9053 to the piercings 9586 in the pierced layer 9585 and to the wells 9582, although other shapes are possible. Without the formed vacuum way 9050, with certain films or other materials, channel 9053 may tend to "kiss" shut when a vacuum in applied to the channel and prevent evacuation of the array. In one embodiment, the vacuum channel 9050 may be formed in layer 9518 with a heat forming fixture (e.g., an appropriately shaped hot 'debossing' wire). In other embodiments, the vacuum channel 9050 may be formed by laser etching, xurography, or the like.

Pierced layer 9585 and second layer 9587 are plastic films that have been sealed to high density array 9581, illustratively by heat sealing (e.g., a heat-activated seal), although it is understood that other methods of sealing may be employed. It is also understood that the material used for high density array 9581 and the material used for pierced layer 9585 and second layer 9587 should be compatible with each other, with the sealing method, and with the chemistry being used. When used for PCR, examples of compatible plastics that can used for high density array 9581 and can be heat-sealed are PE, PP, Monprene®, and other block copolymer elastomers. If fluorescent dyes are used in the detection chemistry, it may be desirable for high density array 9581 to be formed from black or other relatively fluorescently opaque materials, to minimize signal bleed from one well 9582 to its neighboring wells and for at least one of layers 9585 and 9587 to be relatively fluorescently transparent. For pierced layer 9585 and second layer 9587, laminates of a strong engineering plastic such as Mylar® or PET with heat-sealable plastic layers such as PE, PP and Dupont Surlyn® may be used. For adhesive-based systems, rigid engineering plastics such as PET or polycarbonate may be used to form high density array 9581 and films of PCR-compatible plastics are then used as pierced layer 9585 and second layer 9587. In one illustrative embodiment, high density array 9581 is formed of black PE, a composite polyethylene/PET laminate (or Xerox® PN 104702 hot laminating pouch material) is used for pierced layer 9585 and second layer 9587 which are heat sealed to high density array 9581, and composite polypropylene/PET is used for first and second layers 9518, 9519 of pouch 9510.

It is understood that piercings 9586 align with wells 9582. It is also understood that piercings 9586 are small enough that, absent some force, fluid does not readily flow through piercings 9586. Illustrative piercings may be 0.001-0.1 mm, more illustratively 0.005-0.02 mm, and more illustratively about 0.01 mm. In an illustrative embodiment, a vacuum is applied to second-stage amplification zone 9580 in situ by pulling a vacuum on wells 9582 through vacuum channel 9050 through vacuum port 9051 and then sealing (e.g., heat sealing) the vacuum channel 9050. Subsequently, when fluid is provided, the vacuum draws fluid through piercings 9586 into each well 9582. Once the wells 9582 are filled and pressure is equalized, a force is no longer present to force fluid into or out of the wells 9582. Illustratively, wells may be sealed after filling by applying a heat seal substantially perpendicular to the fill channel 9052. In another embodiment, a bladder adjacent second-stage amplification zone 9580 (not shown, but similar in position to bladders 880/882) may then be activated to press first layer 9518 against high density array 9581 and seal fluid into the wells 9582. While first layer 9518 of pouch 9510 is used to seal the wells 9582, it is understood that an optional sealing layer may be provided between pierced layer 9585 and first layer 9510.

In one illustrative example, second-stage amplification zone 9580 may be prepared as follows. High density array 9581 may be prepared by first punching, molding, or otherwise forming an array of wells 9582 in a plastic sheet (illustratively 0.1 to 1 mm thick). The wells may form any regular or irregular array that is desired, and may have a volume illustratively of 0.05 µl to 20 µl, and more illustratively of 0.1 µl to 4 µl. A backing layer (e.g., 9587) is then laminated to a first surface 9581a of high density array 9581, illustratively by heat or adhesive. As shown in FIG. 9B, second layer 9587 is applied to first surface 9581a. Reagents 9589, illustratively elements of the chemistry of the array that are unique, such as PCR primer pairs, are then spotted into the wells either manually by pipetting, or automatically (illustratively using x/y positionable spotters such as pin-spotters, dot-matrix printers, small-volume automatic pipettes, or micro-fluidic micro-contact spotters, for example spotters as taught in U.S. Patent Application No. 2017-0209844, herein incorporated by references). After the reagents 9589 have been dried in each well 9582, pierced layer 9585, which has been previously bonded to layer 9518, may be applied to the second surface 9581b of array 9581. Array 9581 may be bonded to layer 9519 of pouch 510 and sealed in place, illustratively by either heat sealing, using an adhesive, ultrasonically welding, mechanical closure, or other means of enclosing array 9581 inside pouch 510 within blister 580. It is understood that second-stage reaction zone 9580 is fluidly connected to a downstream fluid blister (e.g., a first stage reaction zone) via channel 9565, and that liquid can flow from channel 9565 into second-stage reaction zone 9580 and over piercings 9586 through channel 9565, which is in fluid communication with fluid flow channel 9053 and vacuum way 9050.

Second-stage reaction zone 9580 may be used in a manner similar to second-stage array 11000 of FIG. 7A or array assembly 8000a of FIG. 7A. Because a vacuum may be applied to array 9581, when liquid is moved from blister a downstream fluid reservoir to second-stage amplification zone 9580, the liquid sample is drawn through fluid flow channel 9053 and piercings 9586 and into wells 9582.

Because the array assembly is provided with a vacuum port in fluid communication with the plurality of wells, a vacuum can be applied (locally) to the array assembly (rather than (globally, during manufacture or assembly of an analytical device, such as a pouch in which the array assembly is disposed). Accordingly, an evacuation chamber is not required to apply a vacuum during manufacture, because the product need not be assembled under vacuum conditions. Instead, a piston pump (e.g., a syringe or syringe-type vacuum device) or another vacuum device can be used to apply a vacuum on-demand, at the point-of-use, and even during performance of other steps of an analytical method, rather than during assembly of an analytical device, such as a pouch in which the array assembly is disposed. Accordingly, an evacuation chamber is not required to apply a vacuum so that the product can be assembled under vacuum conditions. Instead, a piston pump or other vacuum device can be used to apply the vacuum.

In one illustrative manufacturing process, the volume of an evacuation chamber used during manufacture of the analytical device comprising the array assembly that is packages under vacuum would be many, many times larger than the volume of the wells and channel system of the array assembly. Evacuating larger volumes requires a larger pump and/or takes longer than a smaller volume. Larger pumps, such as a diaphragm vacuum or rotary vane pump, are generally worse at pulling a (hard) vacuum in a larger volume than is a piston pump at pulling a (hard) vacuum in a smaller volume. Moreover, larger pumps capable of pulling the level of vacuum pulled by a piston pump can be much more expensive to acquire, operate, and/or maintain than a piston pump. In addition, a single stroke of a piston pump can pull a (level of) vacuum that would take much longer for a larger, diaphragm or rotary vane pump. Accordingly, in a given amount of time, a piston pump can pull a more complete (e.g. closer to a total) vacuum than can a larger, diaphragm or rotary vane pump.

As described above, the vacuum can also be applied on-demand, such as at the point-of-use. Accordingly, the vacuum need not be held or maintained by the array assembly for an extended period of time. Instead, unlike existing systems where the analytical device is packaged under vacuum, such that the analytical device must hold or maintain the vacuum during storage, shipping, transfer to the analytical device, and preliminary steps in an analytical process, the on-demand vacuum can be applied to the wells moments before and/or maintained right up until releasing or using the vacuum to draw fluid into the wells (e.g., through the channel system) by opening the fluid seal. For instance, in a preferred embodiment, the vacuum need only be maintained by the by the array assembly for a few seconds (i.e., long enough to create a vacuum seal and open the fluid seal), before the liquid sample is drawn into the wells. In this way, as much as (nearly) the full level of the drawn vacuum can be used to draw a full, consistent amount of fluid into each of the wells upon opening the fluid seal to release the vacuum.

In addition, because the vacuum is not drawn through the liquid sample via the fluid opening, the level or strength of the vacuum is not limited to the partial pressure of the fluid sample. The negative pressure level of this stronger vacuum (e.g., illustratively between 2 mBar and 140 mBar) can thoroughly evacuate air from the array assembly so that residual air is minimized in the array assembly, which minimizes air bubbles that may be trapped by the drawn fluid in the channels and wells or the array assembly. Moreover, the array assembly can be configured (e.g., sized and structured) so that an evacuation chamber is not required to apply the vacuum. Instead, the combined volume of the wells and channel system can be sufficiently small to allow all or substantially all of the air to be evacuated with a single stroke of a piston pump. It will be appreciated, however, that other types of vacuum devices (e.g., rotary vane or diaphragm pumps) can be used in some embodiments.

Figure 11A:
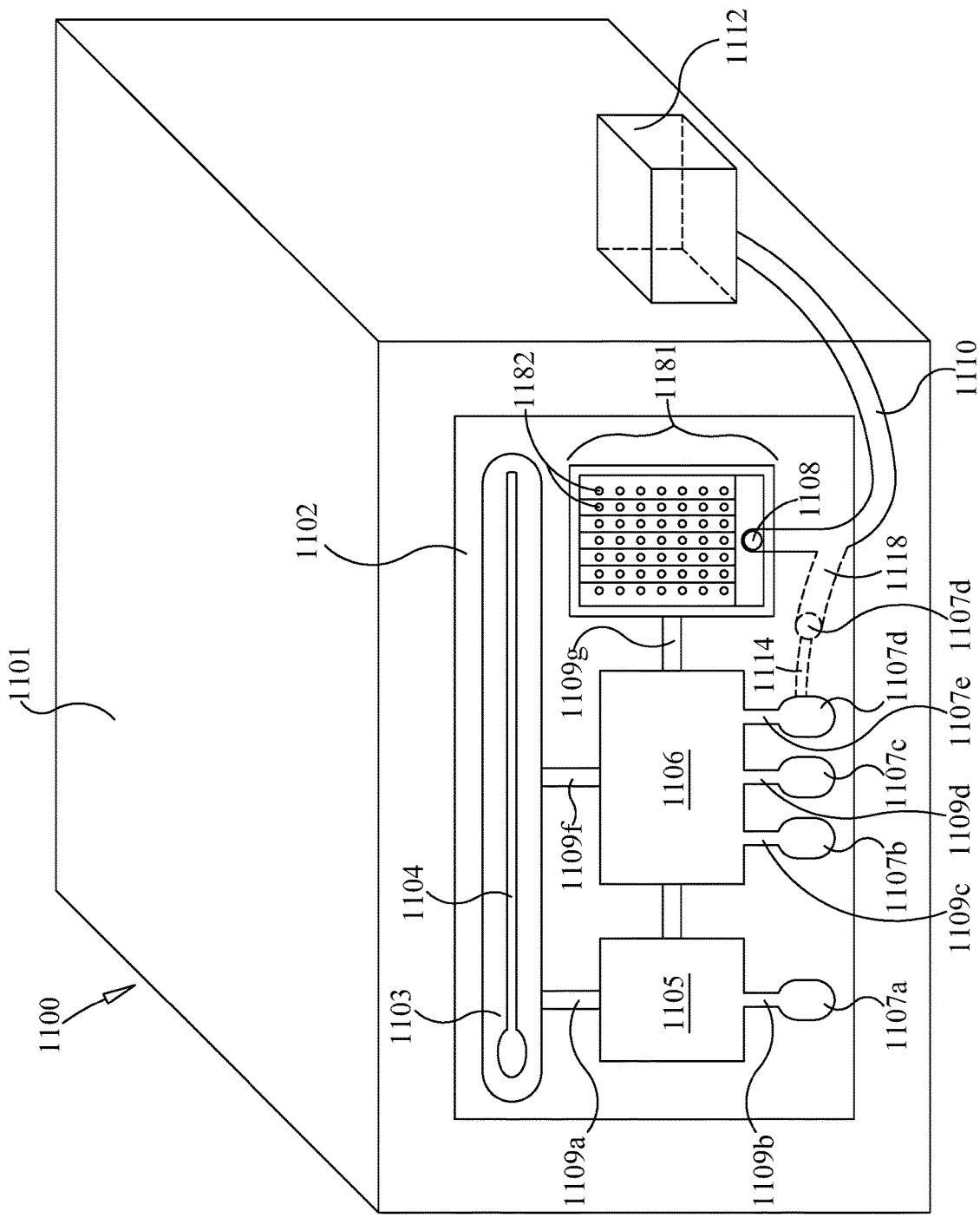
FIG. 11A schematically illustrates an instrument configured for drawing a vacuum on a portion of a reaction container during or after performing one or more steps of an analytical method.

FIG. 11A schematically illustrates a system 1100 that includes an instrument 1101 that can draw a vacuum in a reaction container in situ while performing one or more steps of an analytical method. An exemplary reaction container that is configured for in situ application of a vacuum to one or more parts (e.g., blisters, the second-stage array, reagent wells or blisters, etc.) of the reaction container is shown at 1102. While reaction container 1102 has a specific form and layout, one will appreciate that this is merely exemplary and that other reaction containers—e.g., pouch 8000a—may be adapted for in situ application of a vacuum.

Reaction container 1102 includes a sample blister 1103 that may be used for introducing a sample into the reaction container. In one embodiment, the sample may be introduced with a swab 1104. However, swab 1104 is merely illustrative. In other embodiments, a liquid sample may be introduced with, for example, a transfer pipet, or a dry sample (e.g., a soiled tissue) may be placed into the sample blister 1103. The reaction container 1102 further includes a lysis zone 1105 where cells and viruses in the sample can be lysed to free their nucleic acids for analysis and a reaction zone 1106 where various method steps can be performed such as, but not limited to, nucleic acid recovery and purification, first-stage multiplex PCR, and preparation of first-stage product for second-stage PCR. In one embodiment, the lysis zone 1105 and the reaction zone 1106 can be combined into one zone for lysis, purification of nucleic acids, first-stage PCR, etc. In another embodiment, the lysis zone 1105 and the reaction zone 1106 can be divided between a number of separate blisters dedicated to separate functions. Pouch 510 is an example of such a reaction container with a number of separate blisters dedicated to different functions.

Illustrative reaction container 1102 further includes a number of reagent blisters 1107a-1107d that can be used to provide reagents for assays run in the reaction container. The reagent blisters can contain dry reagents, liquid reagents, or a combination of both. While four reagent blisters are shown, one will appreciate that more or fewer may be included, depending on the assay to be performed in the reaction container. Likewise, the reagent blisters may be connected to the reaction blisters in a number of different configurations, depending on the assay to be performed in the reaction container. Reaction container 1102 further includes a number of channels 1109a-1109g used to connect the zones of the reaction container. In one embodiment, the channels 1109a-1109g may be openably sealed, as explained in detail elsewhere herein. Reaction container 1102 further includes an array 1181 that includes a number of wells 1182 that can be configured for individual assay reactions.

While instrument 1101 is shown only schematically, persons of ordinary skill will appreciate that instrument 1101 may be configured for performing a number of manipulations, heating steps, cooling steps, etc. on reaction container 1102 in the process of performing an analytical method. In one embodiment, instrument 1101 may include one or more heaters configured for controlling the temperature of one or more portions of reaction container 1102. For instance, such heaters may be configured for thermocycling one or more portions of reaction container 1102 for performing one or more PCR reactions. Similarly, such heaters may be configured for one or more isothermal processes in one or more portions of reaction container 1102. In one embodiment, instrument 1101 may include a lysis apparatus (e.g., a bead beater like element 804 of FIG. 2, a paddle bead beater, a sonicator, etc.) for performing cell lysis in one or more portions of reaction container 1102. In one embodiment, instrument 1101 may include a magnet for magnetic bead capture. In one embodiment, instrument 1101 may include actuators for moving fluids within one or more portions of the reaction container 1102. In one embodiment, instrument 1101 may include one or more seals (e.g., retractable seals and/or heat seals) for controlling the movement of fluids within one or more portions of the reaction container 1102. In one embodiment, instrument 1101 may light source(s) and image capture systems for optical (e.g., fluorescent) excitation and data collection from one or more portions of the reaction container 1102.

In addition, instrument 1101 may include a computer (either an internal or external computer, or both), an integrated display, a heat seal apparatus to apply heat seals to one or more portions of the reaction container 1102, and/or compression members (e.g., inflatable bladders) for compressing one or more portions of the reaction container 1102 against components of instrument 1101. For example, compression members may be used to improve thermal contact between one or more portions of the reaction container 1102 and one or more heaters. In one embodiment, instrument 1101 is configured for performing at least one PCR reaction in the reaction container 1102. Other components that may be included in instrument 1102 are shown in FIGS. 2-4 and are discussed in the accompanying text. However, one will appreciate that the form and arrangement of the components shown in FIGS. 2-4 may be different in instrument 1102, but the functions may be the same or similar.

In addition to the foregoing, the instrument 1101 and the reaction container 1102 may be configured for drawing a vacuum in one or more portions of reaction container 1102 either prior to or while performing an analytical method. As discussed in detail elsewhere herein, having one or more portions of reaction container 1102 under partial vacuum can facilitate filling one or more portions with a fluid. For example, filling the array wells 1182 may be greatly facilitated by having the array 1181 under partial vacuum.

In one embodiment, the reaction container 1102 includes a channel system similar to those illustrated, for example in FIGS. 7A, 8A, 8C, and 9A for applying a vacuum to one or more portions of the reaction container. In addition, instrument 1101 includes a system for drawing a vacuum in one or more portions of the reaction container 1102 while performing an analytical method. The vacuum system includes a vacuum line 1110 and a vacuum source 1112. Vacuum source 1112 may be essentially any vacuum source or vacuum generating device known in the art. Examples include, but are not limited to, piston pumps (e.g., a syringe pump), positive displacement pumps, momentum transfer pumps (also called molecular pumps), and entrapment pumps (also called molecular traps). In one embodiment, vacuum source 1112 may include an evacuated chamber that is connected to a vacuum pump.

In such a system, the partial vacuum in the evacuated chamber may be used to draw a vacuum on one or more portions of the reaction container 1102 and, in turn, a vacuum pump may be used to draw or maintain a vacuum in the evacuated chamber. In one embodiment, vacuum source 1112 and vacuum line 1110 may draw a vacuum on array 1181 at vacuum port 1108. In one embodiment, vacuum source 1112 may be fluidly coupled to at least one additional vacuum line for drawing a vacuum on at least one additional portion of the reaction container 1102. For example, FIG. 11A illustrates an extension 1118 on vacuum line 1110 that may be used for drawing a vacuum on at least one reagent blister via port 1116.

In one embodiment, the instrument 1101 may be used to apply a vacuum to one or more portions of the reaction container 1102 while performing an analytical method, or after the instrument has performed at least one step of an analytical method. For instance, the instrument 1101 may draw a vacuum in the reaction container 1102 while or after inserting the reaction container into the instrument, while or after hydrating a sample, while or after performing one or more method steps or reactions in a first reaction zone (e.g., the lysis zone 1105), while or after performing one or more method steps or reactions in a second reaction zone (e.g., reaction zone 1106), or in preparation for filling one or more portions of the reaction container 1102 with fluid. For instance, instrument 1101 may draw a vacuum in the array 1181 or in reagent blister 1107d (or another reagent blister) in preparation for filling them with fluid.

In one example, the one or more method steps or reactions in a first reaction zone may include, but are not limited to, sample lysis (e.g., by bead beating), isolation of lysis particles from the lysate, moving the lysate to another chamber in the reaction container, mixing silica magnetic beads with the lysate, or capturing the magnetic beads and moving them to another chamber in the reaction container.

In one example, the one or more method steps or reactions in a second reaction zone may include, but are not limited to, mixing silica magnetic beads with a lysate from the first reaction zone, moving the spent lysate (i.e., residual lysate after nucleic acid capture) to another chamber in the reaction container (e.g., to a waste chamber), performing at least one wash of the magnetic beads and moving the wash liquid to another chamber in the reaction container, elution of nucleic acids from the silica magnetic beads, performing a first PCR reaction (e.g., a singleplex or a multiplex PCR), or diluting a product of the first PCR reaction in preparation for performing a second PCR reaction in the wells of the array.

Figure 11B:
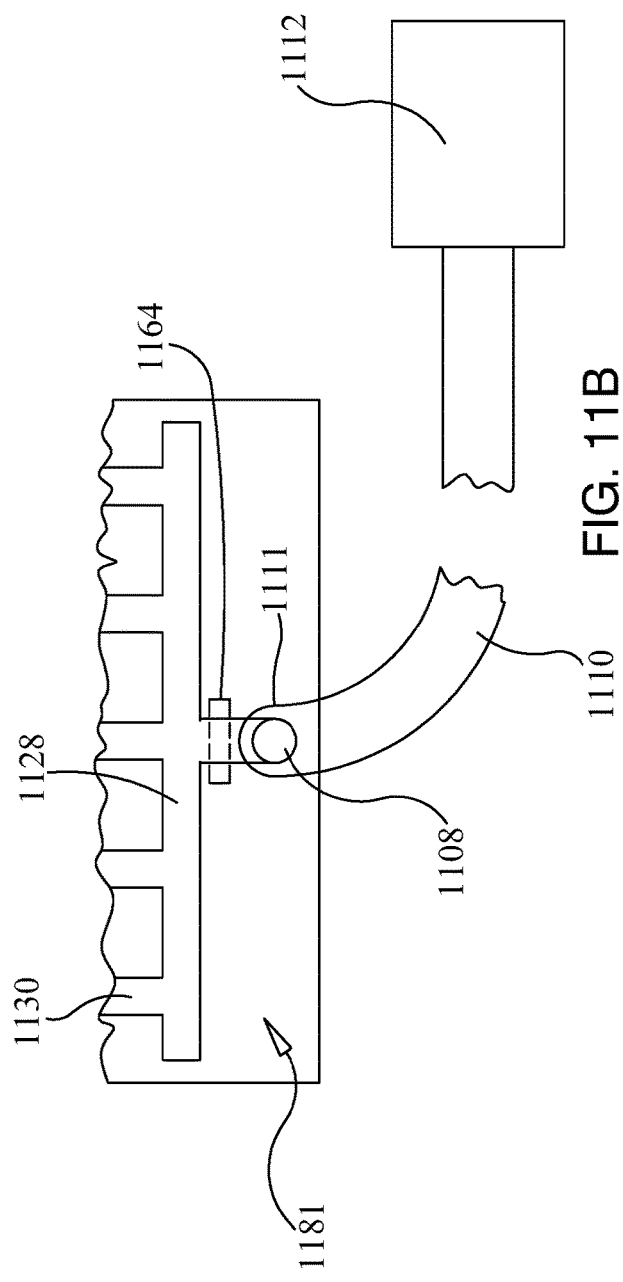
FIG. 11B illustrates the vacuum system and a portion of an array of the reaction container of FIG. 11A configured for in situ drawing of a vacuum.
Figure 11C:
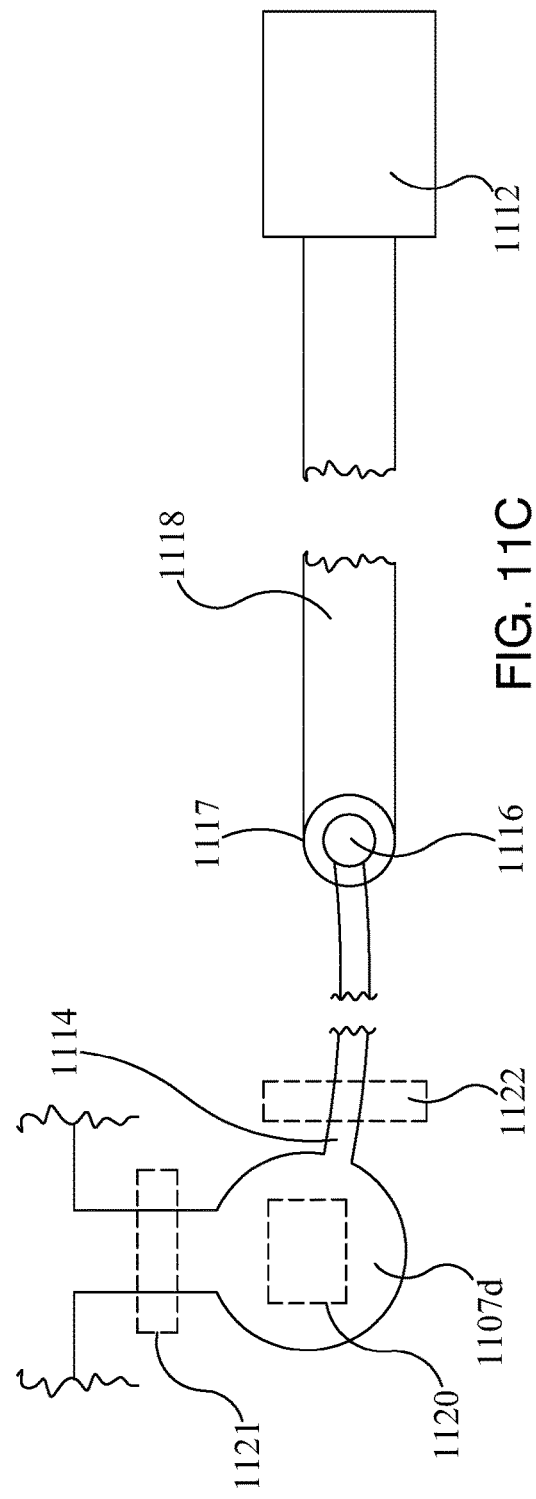
FIG. 11C illustrates the vacuum system and a reagent blister of the reaction container of FIG. 11A configured for in situ drawing of a vacuum.

FIGS. 11B and 11C illustrate systems for drawing of a vacuum on an array and a reagent blister in greater detail. FIG. 11B shows a vacuum manifold 1128 and 1130 for an array 1181. Details of an embodiment of a vacuum manifold and how it relates to the array, the array wells, etc. was shown in FIGS. 8A-8C and discussed in the accompanying text. In the illustrated embodiment, the vacuum line 1110 and vacuum source 1112 connect to the vacuum port 1108 via vacuum hub 1111. Vacuum hub 1111 may be a resilient member like a suction cup, a nipple, or the like known in the art. In one embodiment, vacuum hub 1111 may include a sharp member (e.g., a needle or the like) positioned to pierce a layer of film over vacuum port 1108. In another embodiment, vacuum port 1108 may include a flapper valve or other valve so that vacuum port may normally be sealed from the outside but the valve can open to allow air to escape when a vacuum is drawn on vacuum port 1108. After a vacuum is drawn on the array 1181, a seal (e.g., a heat seal) may be applied in the region of 1164 to seal channels 1128 and 1130 from outside air and to preserve the vacuum in the array after vacuum hub 1111 is removed.

FIG. 11C shows an illustrative blister 1107d that may be configured for having a vacuum drawn in situ. And while one reagent blister 1107d is shown, one will appreciate that multiple reagent blisters may be linked to one vacuum system, or a reaction container like 1102 may include two or more reagent blisters that may be configured for having an in situ applied vacuum. In the illustrated embodiment, the vacuum line 1118 and vacuum source 1112 connect to reagent blister 1107d via vacuum port 1116 and reaction container vacuum line 1114 via vacuum hub 1117. As with vacuum hub 1111, vacuum hub 1117 may be a resilient member like a suction cup, a nipple, or the like known in the art. In one embodiment, vacuum hub 1117 may include a sharp member (e.g., a needle or the like) positioned to pierce a layer of film over vacuum port 1116. In another embodiment, vacuum port 1116 may include a valve so that vacuum port may normally be sealed from the outside but the valve can open to allow air to escape when a vacuum is drawn on vacuum port 1108. Reaction container vacuum line 1114 may be formed as described elsewhere herein to keep the line open when a vacuum is applied. For instance, reaction container vacuum line 1114 may include an embossed arch formed in the film used to fabricate reaction container 1102, the reaction container vacuum line 1114 may be formed in a card material. As discussed elsewhere herein, an openable seal 1121 in channel 1109e may prevent the vacuum applied to blister 1107d from being applied to other regions of the reaction container 1102. After a vacuum is drawn on reagent blister 1107d, a seal (e.g., a heat seal or a cap) may be applied in the region of 1122 to preserve the vacuum in reagent blister 1107d after vacuum hub 1117 is removed.

In one embodiment, reagent blister 1107d may include a dried chemistry 1120 that may need to be rehydrated for use in an assay. It may be advantageous to apply a partial vacuum to reagent blister 1107*d* in order to, for example, allow rehydration fluid to flow into reagent blister 1107*d* without air blocking fluid flow and so that bubbles are not subsequently introduced into reaction chambers (e.g., reaction chamber 1106). The dried chemistry 1120 may be air dried or freeze dried and may include reaction components (e.g., enzymes), buffers, stabilizing agents, and the like. The dried chemistry 1120 may be in the form of a powder, a dried reagent pill, a reagent spotted onto a filter paper, or other forms known in the art.

It is understood that in various embodiments of arrays described herein, reaction components may be spotted in the wells. For example, primers may be spotted in each well for priming nucleic acid amplification reactions. Each well may have a different pair of primers, various wells may include replicates of primers found in other wells, or any combination thereof. Additional materials may be spotted, including one or more of nucleotide tri-phosphates (NTPs), polymerase, magnesium, or other components. When such components are spotted and dried during manufacturing, the components often dry around the edges of the well, leaving a relatively small surface area for rehydration. With fast PCR embodiments, see, e.g. PCT/US2017/18748, herein incorporated by reference, the time needed for such rehydration may extend through a number of PCR cycles, which may require additional cycling time.

Figure 10A:
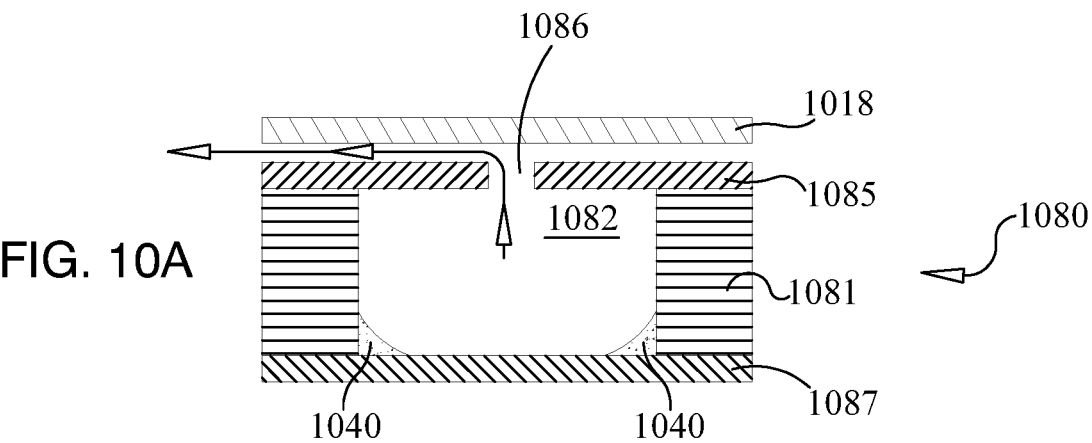
FIGS. 10A-10E illustrate a method for rehydrating the contents and initiating a reaction in an illustrative well of a second-stage array.
Figure 10B:
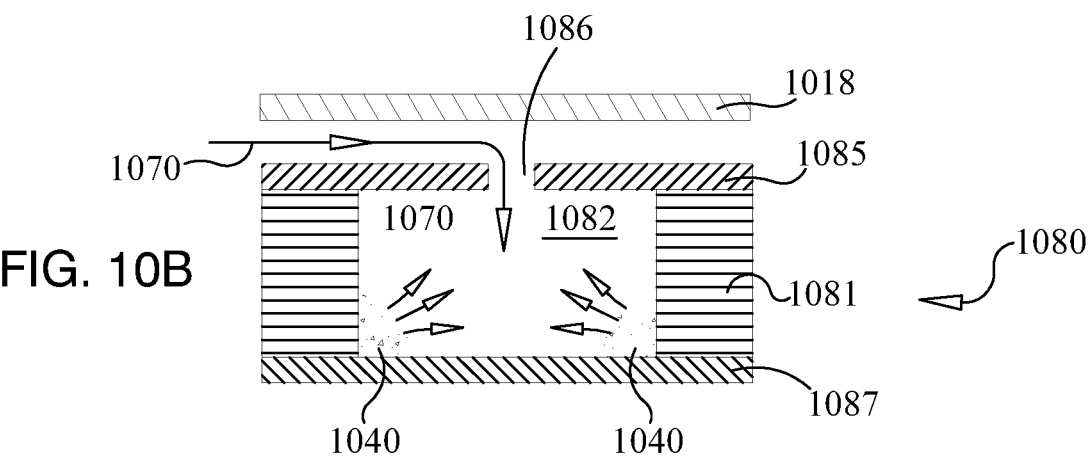
Figure 10C:
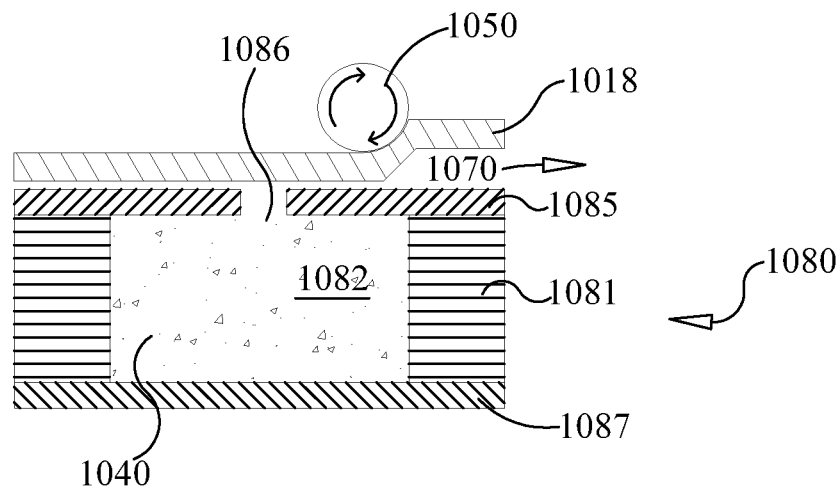
Figure 10D:
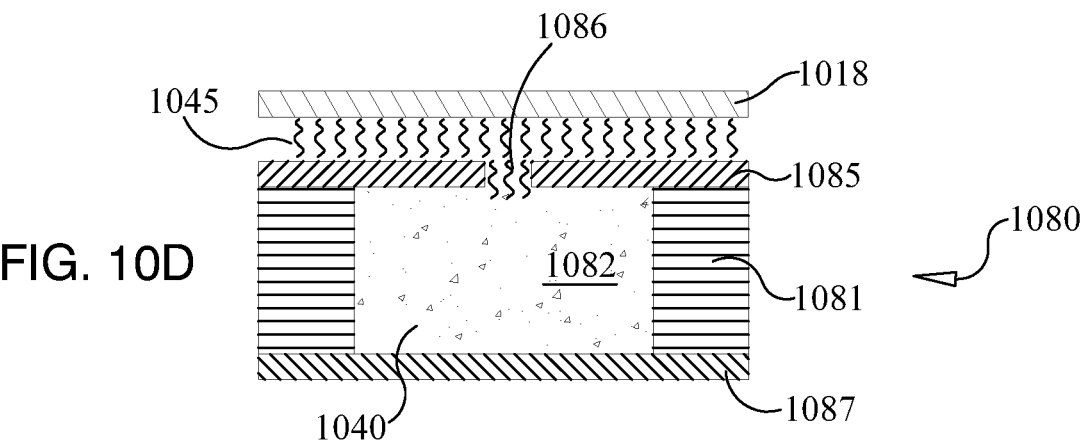
Figure 10E:
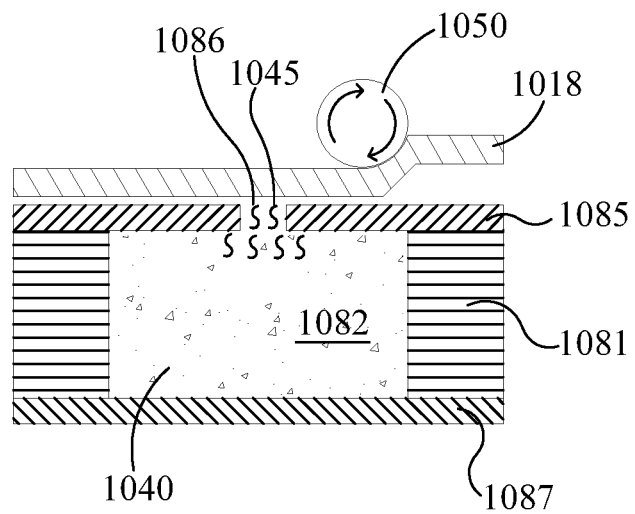
Figure 10F:
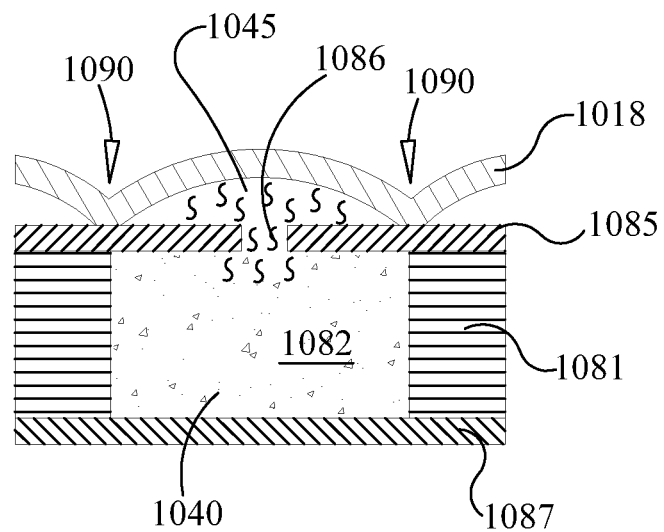
FIG. 10F illustrates an alternative method of initiating a reaction in the method illustrated in FIGS. 10A-10E.

Turning now to FIGS. 10A-F, one way to decrease the time spent for rehydration and dissolution during second-stage PCR thermal cycling is to flood the array with a hydration fluid prior to the time in the reaction process when the array will be used, illustratively during sample preparation or during first-stage PCR. FIGS. 10A-10E illustrate an example of a method for rehydrating the contents and initiating a reaction in an illustrative well of a second-stage array. FIG. 10F illustrates an alternative method of initiating a reaction in the method illustrated in FIGS. 10A-10E. While FIGS. 10A-F show one well 1082 of an array 1080, it is understood that a plurality of wells may be present, illustratively in arrangements such as in array 580, array 5081, and array 8000, as well as other array configurations. Illustrative well 1082 is formed in array layer 1081, and is bounded by pierced layer 1085 and second layer 1087. It is understood that layer 1018 may be an outer layer of a pouch, similar to layer 518, or layer 1018 may be an extra flexible layer provided for rehydration methods. Array 1080 may be used in various embodiments described herein or in other sample processing systems.

Array 1080 may be spotted with various components 1040 for sample processing, illustratively components for PCR. Illustrative ways of spotting array 1080 are described in U.S. Pat. Pub. No. 2015/0283531, herein incorporated by reference, but it is understood that other ways of spotting array 1080 are within the scope of this disclosure. Subsequent to spotting, array 1080 may be dried. As illustrated in FIG. 10A, the components 1040 often dry into the corners of well 1082. Optionally, array 1080 may be evacuated at point of use, as shown by the arrow in FIG. 10A and as described in detail elsewhere herein. Likewise, array 1080 may be evacuated at the time of manufacture and then stored under vacuum until time of use.

In FIG. 10B, hydration fluid 1070, illustratively water or buffer, is introduced to well 1082 through opening 1086. It is understood that opening 1086 may be a piercing, such as piercing 586 described elsewhere herein, where opening 1086 is small enough that, absent some force, fluid does not readily flow through opening 1082. In some embodiments, however, it may be desirable for opening 1086 to be larger, or it may be desirable to use other barrier layers. After filling with hydration fluid 1070, excess hydration fluid may be removed from the array, illustratively by rolling the fluid toward a waste receptacle (not shown) using roller 1050, as shown by FIG. 10C, or by placing pressure on the array, for example by a bladder located in an instrument adjacent array 1080. Since the materials in each array well are in need of rehydration, if excess hydration fluid 1070 is removed immediately, the amount of cross-contamination between wells will be minimized, as the excess hydration fluid is removed as the reaction components 1040 begin to rehydrate into the hydration fluid 1070. Optionally, pressure may be placed on layer 1087 as excess hydration fluid 1070 is moved to the waste receptacle, which pressure reduces the volume of well 1082, thereby causing well 1082 to be under-filled.

In FIG. 10D, subsequent to first-stage PCR, the first-stage reaction mixture 1045 may be moved into array 1080, illustratively by pressure. Because each of the wells are flexible and are already will be filled, but illustratively not over-filled due to the removal of excess hydration fluid, each well can accept a small amount of reaction material such as first-stage PCR reaction mixture 1045. Because only a small amount of first-stage PCR reaction mixture 1045 is introduced to each well, a dilution step of the first-stage PCR reaction mixture prior to introduction of the first-stage PCR reaction mixture may be omitted. If well 1082 is under-filled as discussed above, the amount first-stage PCR reaction mixture 1045 that may be introduced into each well may be somewhat greater, and, accordingly, the amount of dilution will be somewhat reduced. The amount of pressure placed on layer 1087 during removal of excess hydration fluid 1070 may be adjusted to provide an appropriate amount of dilution.

As shown in FIG. 10E, roller 1050 or other pressure may be used again to remove excess first-stage PCR reaction mixture 1045. In this illustrative embodiment, only a small amount of first-stage PCR reaction mixture 1045 is pushed through opening 1086. FIG. 10F shows an alternative embodiment, where instead of forcing excess first-stage reaction mixture 1045 out of array 1080, layer 1018 is sealed to pierced layer 1085, illustratively by pressure or heat sealing at arrows 1090. In this embodiment, a bolus of first-stage PCR reaction mixture 1045 becomes sealed outside opening 1086, and first-stage PCR reaction mixture 1045 and components 1040 may continue to mix during subsequent thermal cycling. This embodiment may result in less dilution than the embodiment shown in FIG. 10E.

Because this pre-rehydration of the array 1080 may include relevant reactants, it may be desirable to omit one of the reactants from the array until the first-stage reaction mixture is provided to the array so that the reaction mixture is incomplete and the reaction in the array cannot begin until the first-stage reaction mixture is provided. For example, if the second-stage array 1080 is used for PCR, magnesium may be omitted from both the dried array components and the hydration fluid, thus preventing primer dimers from forming during rehydration. In such a method, high concentration of magnesium may be added to the first-stage reaction mixture prior to providing the first-stage reaction mixture to the array, and dilution of this mixture when the small amount of the first-stage reaction mixture is introduced into each well provides the appropriate concentration of magnesium to the array to allow PCR to proceed. It is understood that magnesium is an illustrative component, and that other components may be used to control start of amplification. Also, it is understood that a complete mixture may be provided to each well, and that the start of the reaction may be controlled by controlling temperature of the reactions, illustratively by cooling using a heater such as heater 888.

Accordingly, embodiments of the present disclosure provide numerous advantages over existing systems.

CONCLUSION

While the foregoing detailed description makes reference to specific exemplary embodiments, the present disclosure may be embodied in other specific forms without departing from its spirit or essential characteristics. Accordingly, the described embodiments are to be considered in all respects only as illustrative and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the invention as defined by the appended claims.

The limitations recited in the claims are to be interpreted broadly based on the language employed in the claims and not limited to specific examples described in the foregoing detailed description, which examples are to be construed as non-exclusive and non-exhaustive. All changes which come within the meaning and range of equivalency of the claims are to be embraced within their scope.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment. In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein.

We claim:

1. A method of moving a fluid within a sample container, the method comprising:
   (a) providing the sample container comprising
      (i) a first reaction zone comprising a fluid reservoir having a fluid disposed therein,
      (ii) a second reaction zone, and
      (iii) a fluid channel extending between the first reaction zone and the second reaction zone, the fluid channel comprising an openable seal disposed between the first reaction zone and the second reaction zone,
      the second reaction zone comprising the array assembly, the array assembly comprising
         a plurality of wells configured in an array,
         a vacuum port and a vacuum channel fluidly connected to the vacuum port, and
         a plurality of channels such that each well in the array is fluidly connected to the fluid channel and to the vacuum port and vacuum channel;
   (b) with the openable seal in a closed state, and with the vacuum port and vacuum channel opened, drawing, through the vacuum port and vacuum channel, a vacuum on the array assembly such that air is evacuated from the plurality of wells and the plurality of channels;
   (c) after drawing the vacuum on the array assembly, sealing the vacuum port and/or vacuum channel such that the plurality of wells and the plurality of channels are maintained under the vacuum, thereby forming an evacuated array; and
   (d) after sealing the vacuum port and/or vacuum channel, opening the openable seal such that the fluid is drawn into the plurality of wells via the plurality of channels.

2. The method of claim 1, further comprising mixing the reaction mixture with one or more reagents disposed in each of the plurality of wells to form a second mixture.

3. The method of claim 2, wherein the second mixture is a PCR mixture.

4. The method of claim 3, further comprising thermocycling the second reaction mixture.

5. The method of claim 4, further comprising detecting an amplification product in at least one of the plurality of wells.

6. The method of claim 2, wherein the sample comprises a microorganism and the one or more reagents comprises an antibiotic.

7. The method of claim 6, wherein the antibiotic is present in a first of the plurality of wells at a first concentration and is present in a second of the plurality of wells at a second concentration, wherein the second concentration is lower than the first concentration.

8. The method of claim 1, wherein step (c) provides a vacuum in the plurality of wells of between about 2 millibar and about 150 millibar.

\* \* \* \* \*